United States Patent [19]
Dellaria et al.

[11] Patent Number: 5,514,702
[45] Date of Patent: May 7, 1996

[54] ARYLAMIDOALKYL-N-HYDROXYUREA COMPOUNDS HAVING LIPOXYGENASE INHIBITORY ACTIVITY

[75] Inventors: Joseph F. Dellaria, Lindenhurst; Dee W. Brooks, Libertyville; Jimmie L. Moore, Gurnee; Kevin J. Sallin, Peoria, all of Ill.

[73] Assignee: Abbott Laboratories, Abbott Park, Ill.

[21] Appl. No.: 178,237

[22] PCT Filed: Jul. 7, 1992

[86] PCT No.: PCT/US92/05715

§ 371 Date: Jan. 10, 1994

§ 102(e) Date: Jan. 10, 1994

[87] PCT Pub. No.: WO93/02037

PCT Pub. Date: Feb. 4, 1993

Related U.S. Application Data

[63] Continuation-in-part of Ser. No. 732,520, Jul. 19, 1991, Pat. No. 5,214,204.

[51] Int. Cl.⁶ .......... A61K 31/34; A61K 31/38; C07D 333/32; C07D 333/34
[52] U.S. Cl. .......... 514/438; 514/471; 549/65; 549/441
[58] Field of Search .......... 549/65, 441; 514/438, 514/471

[56] References Cited

U.S. PATENT DOCUMENTS

| | | | |
|---|---|---|---|
| 4,407,822 | 10/1983 | Lafon | 514/575 |
| 4,897,422 | 11/1990 | Summers | 514/575 |

*Primary Examiner*—Alan L. Rotman
*Attorney, Agent, or Firm*—Jerry F. Janssen

[57] ABSTRACT

The present invention provides certain (substituted carbocyclic aryl)amidoalkyl- and (substituted heterocyclic aryl)amidoalkyl-N-Hydroxy urea compounds which inhibit lipoxygenase enzyme activity and are thus useful in the treatment of allergic and inflammatory disease states.

7 Claims, No Drawings

ARYLAMIDOALKYL-N-HYDROXYUREA COMPOUNDS HAVING LIPOXYGENASE INHIBITORY ACTIVITY

This application is a continuation-in-part of application Ser. No. 07/732,520 filed Jul. 19, 1991, now U.S. Pat. No. 5,214,204.

TECHNICAL FIELD

This invention relates to compounds having activity to inhibit lipoxygenase enzymes, to pharmaceutical compositions comprising these compounds, and to a medical method of treatment More particularly, this invention concerns certain substituted arylamidoalkyl-N-hydroxyurea compounds which inhibit leukotriene biosynthesis, to pharmaceutical compositions comprising these compounds, and to a method of inhibiting lipoxygenase activity and leukotriene biosynthesis.

BACKGROUND OF THE INVENTION

5-Lipoxygenase is the first dedicated enzyme in the pathway leading to the biosynthesis of leukotrienes. This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis,cis-1,4-pentadiene structures, converting them to 1-hydroperoxy-trans,cis- 2,4-pentadienes. Arachidonic acid, the 5-lipoxygenase substrate which leads to leukotriene products, is found in very low concentrations in mammalian cells and must first be hydrolyzed from membrane phospholipids through the actions of phospholipases in response to extracellular stimuli. The initial product of 5-lipoxygenase action on arachidonate is 5-HPETE which can be reduced to 5-HETE or converted to $LTA_4$. This reactive leukotriene intermediate is enzymatically hydrated to $LTB_4$ or conjugated to the tripeptide glutathione to produce $LTC_4$. $LTA_4$ can also be hydrolyzed nonenzymatically to form two isomers of $LTB_4$. Successive proteolytic cleavage steps convert $LTC_4$ to $LTD_4$ and $LTE_4$. Other products resulting from further oxygenation steps have also been described in the literature. Products of the 5-lipoxygenase cascade are extremely potent substances which produce a wide variety of biological effects, often in the nanomolar to picomolar concentration range.

The remarkable potencies and diversity of actions of products of the 5-lipoxygenase pathway have led to the suggestion that they play important roles in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

The enzyme 5-lipoxygenase catalyzes the fast step leading to the biosynthesis of all the leukotrienes and therefore inhibition of this enzyme provides an approach to limit the effects of all the products of this pathway. Compounds which inhibit 5-lipoxygenase are thus useful in the treatment of disease states such as those listed above in which the leukotrienes play an important role.

SUMMARY OF THE INVENTION

In its principal embodiment, the present invention provides certain substituted amidoalkyl-N-hydroxyurea and aminoalkylurea compounds which inhibit lipoxygenase enzyme activity. The compounds are useful in the treatment of allergic and inflammatory disease states in which leukotrienes play a role including asthma, allergic rhinitis, rheumatoid arthritis and gout, psoriasis, adult respiratory distress syndrome, inflammatory bowel disease, endotoxin shock syndrome, ischememia induced myocardial injury, atherosclerosis and central nervous system pathology resulting from the formation of leukotrienes following stroke or subarachnoid hemorrhage.

The compounds of the present invention are of the formula

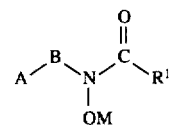

or a pharmaceutically acceptable salt thereof wherein $R^1$ is selected from the group consisting of hydrogen, alkyl of from one to six carbon atoms, alkenyl of from two to six carbon atoms, cycloalkyl of from three to six carbon atoms, and $NR^2R^3$ where $R^2$ and $R^3$ are independently hydrogen or alkyl of from one to six carbon atoms.

The group A is selected from the group consisting of

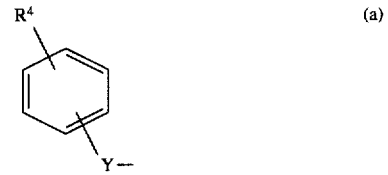 (a)

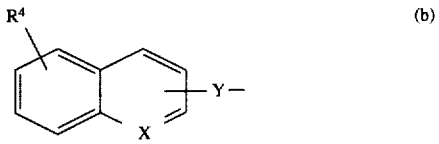 (b)

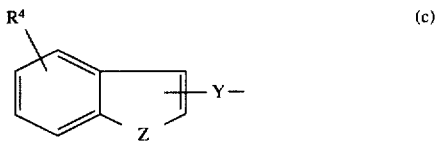 (c)

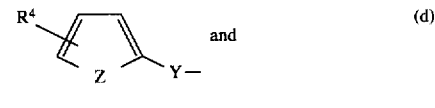 (d)

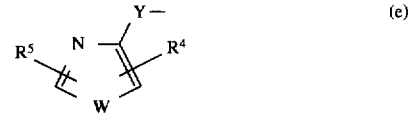 (e)

wherein $R^4$ is selected from (a) hydrogen, (b) one, two, or three halogen atoms, (c) amino, (d) alkyl of from one to six carbon atoms, (e) alkoxy of from one to twelve carbon atoms, (f) alkenyloxy in which the alkenyl portion is of from one to twelve carbon atoms, (g) phenoxy, optionally substituted with one, two, or three halogen atoms, alkyl of from one to six carbon atoms, haloalkyl of from one to six carbon atoms, alkoxy of from one to six carbon atoms, phenylalkoxy in which the alkoxy portion is of from one to six carbon atoms, (h) thiophenoxy, optionally substituted with one, two, or three halogen atoms, alkyl of from one to six carbon atoms, haloalkyl of from one to six carbon atoms, alkoxy of from one to six carbon atoms, (i) benzoyl, (j) pyridyloxy, (k) phenylsulfonyl optionally substiuted with halogen, and (l) phenylamino optionally substituted with halogen.

The group $R^5$ is hydrogen or phenyl optionally substituted with halogen or alkyl of from one to six carbon atoms; W is —$CH_2$—, —O—, or —S—; X is —CH— or N; Y is a valence bond or is selected from alkylene of from one to six carbon atoms, alkenylene of from two to six carbon atoms, and oxyalkylene of from one to six carbon atoms; and Z is oxygen, $NR^6$, or sulfur, where $R^6$ is alkyl of from one to six carbon atoms or substituted or unsubstituted carbocyclic aryl.

The group B is selected from the group consisting of

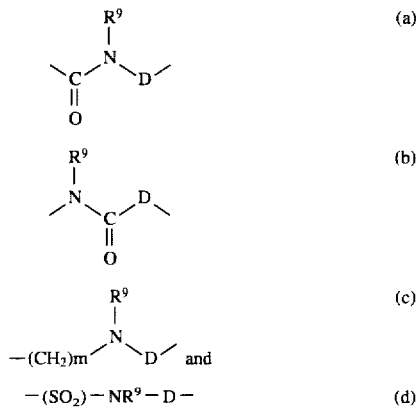

wherein $R^9$ is selected from hydrogen, alkyl of from one to six carbon atoms, benzyl, or thienylmethylene, and D is straight or branched chain alkylene of from one to six carbon atoms; and m is 0 or 1.

The group M is hydrogen, a pharmaceutically acceptable cation, or a pharmaceutically acceptable prodrug leaving group.

In another aspect, the present invention provides pharmaceutical compositions comprising a lipoxygenase inhibiting effective amount of a compound as defined above in combination with a pharmaceutically acceptable carrier.

In yet another aspect, the present invention provides a method of inhibiting lipoxygenase enzyme activity in a host mammal in need of such treatment comprising administering a lipoxygenase inhibiting effective amount of a compound as defined above.

DETAILED DESCRIPTION OF THE INVENTION

Definitions of Terms

As used throughout this specification and the appended claims, the term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl-2-buten-1-yl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "alkenylene" denotes a divalent group derived from a straight or branched chain hydrocaron containing at least one carbon-carbon double bond. Examples of alkenylene include —CH=CH—, —$CH_2$CH=CH—, —C($CH_3$)=CH—, —$CH_2$CH=CH$CH_2$—, and the like.

The term "alkenyloxy" refers to an alkenyl group, as defined above, attached though an oxygen atom to the parent molecular moiety.

The terms "alkoxy" and "alkoxyl" denote an alkyl group, as defined above, attached to the parent molecular moiety through an oxygen atom. Representative alkoxy groups include methoxyl, ethoxyl, propoxyl, butoxyl, and the like.

The term "cycloalkyl" denotes a monovalent group derived from a monocyclic or bicyclic saturated carbocyclic ting compound by the removal of a single hydrogen atom. Examples include cyclopropyl, cyclobutyl, cycopentyl, cyclohexyl, bicyclo[2 2.1]heptanyl, and bicyclo[2.2.2]octanyl.

The term "haloalkyl" denotes an alkyl group, as defined above, having one, two, or three halogen atoms attached thereto and is exemplified by such groups as chloromethyl, bromoethyl, trifluoromethyl, and the like.

The term "phenylalkoxy" refers to a phenyl group attached to the parent molecular moiety through an alkoxy group, as defined above.

The term "prodrug leaving group" denotes a group which is cleaved in vivo to yield the parent molecule of the structural formulae indicated above wherin M is hydrogen. Examples of metabolically cleavable groups include —COR, —COOR, —CONRR and —$CH_2$OR radicals where R is selected independently at each occurrence from alkyl, trialkylsilyl, carbocyclic aryl or carbocyclic aryl substituted with one or more of $C_1$-$C_4$ alkyl, halogen, hydroxy or $C_1$-$C_4$ alkoxy. Specific examples of representative metabolically cleavable groups include acetyl, methoxycarbonyl, benzoyl, methoxymethyl and trimethylsilyl groups.

Preferred Embodiments

Preferred compounds of the present invention are those having the structure

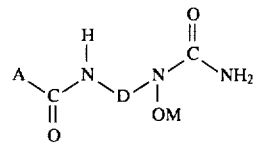

where the values of A, D, and M are as deemed above. Particular compounds falling within the scope of the present invention include, but are not limited to:

N-hydroxy-N-[(((3-phenoxyphenyl)amino)carbonyl)methyl]urea;

N-hydroxy-N-[2-((3-phenoxyphenylbenzoyl)amino)ethyl] urea;

N-hydroxy-N-[(((3-phenylmethoxyphenyl)amino)carbonyl)methyl]urea;

N-hydroxy-N-[((N-methyl-(3-phenoxyphenyl)amino)carbonyl)methyl]urea;

N-hydroxy-N-[(((N-methyl-(3-phenoxyphenyl)amino)carbonyl)methyl]urea;

N-hydroxy-N'methyl-N-[((N-methyl-(3-phenoxyphenyl)amino)carbonyl)methyl]urea;
N-hydroxy-N-[((N-phenylmethyl-(4-bromophenyl)amino)carbonyl)methyl]urea;
N-hydroxy-N-[((N-thien-2-ylmethyl-(4-bromophenyl)amino)carbonyl)methyl]urea;
N-hydroxy-N-[((N-thien-2-ylmethyl-(4-bromophenyl)amino)carbonyl)methyl]urea;
N-hydroxy-N-[((N-methyl-(3-phenylmethoxyphenyl)amino)carbonyl)methyl]urea;
N-hydroxy-N-[(((4-phenoxyphenyl)amino)carbonyl)methyl]urea;
N-hydroxy-N-[(((trans-4-(4-bromophenyl)but-3-en-2-yl)amino)carbonyl)methyl]urea;
N-hydroxy-N-[(((trans-4-(3-phenoxyphenyl)but-3-en-2-yl)amino)carbonyl)methyl]urea;
N-hydroxy-N-[(((cis-4-(4-bromophenyl)but-3-en-2-yl)amino)carbonyl)methyl]urea;
N-hydroxy-N-[2-(((4-bromophenylacetyl)-N-methyl)amino)ethyl]urea;
N-hydroxy-N-[(N-methyl-(3-phenoxyphenylbenzoyl)amino)ethyl]urea;
N-hydroxy-N-[2-((3-methoxyphenylbenzoyl)amino)ethyl]urea;
N-hydroxy-N-[2-((4-methoxyphenylbenzoyl)amino)ethyl]urea;
N-hydroxy-N-[2-((4-butoxyphenylbenzoyl)amino)ethyl]urea;
N-hydroxy-N-[((3-butoxyphenylbenzoyl)amino)ethyl]urea;
N-hydroxy-N-[2-((4-chlorobenzoyl)amino)ethyl]urea;
N-hydroxy-N-[3-(((3-phenoxybenzoyl)amino)propyl]urea;
N-hydroxy-N-[4-((3-phenoxybenzoyl)amino)butyl]urea;
N-hydroxy-N'-methyl-N-[3-((3-phenoxybenzoyl)amino)propyl]urea;
N-hydroxy-N'-methyl-N-[2-((3-phenoxybenzoyl)amino)ethyl]urea;
N-hydroxy-N-[2-((3 -(3-trifluoromethylphenoxy)benzoyl)amino)ethyl]urea;
N-hydroxy-N-[2-((3-(4-chlorophenoxy)benzoyl)amino)ethyl]urea;
N-hydroxy-N'-methyl-N-[2-((3-(4-chlorophenoxy)benzoyl)amino)ethyl]urea;
N-hydroxy-N-[2-((3-(4-methoxyphenoxy)benzoyl)amino)ethyl]urea;
N-hydroxy-N-[2-((3-(3,4-dichlorophenoxy)benzoyl)amino)ethyl]urea;
N-hydroxy-N-[2-((3-(3,5-dichlorophenoxy)benzoyl)amino)ethyl]urea;
N-hydroxy-N-[2-((3-(4-tert-butylphenoxy)benzoyl)amino)ethyl]urea;
(R)-N-hydroxy-N-[2-((3-phenoxybenzoyl)amino)propyl]urea;
N-hydroxy-N-[3-((3-phenoxybenzoyl)amino)prop-2-yl]urea;
N-hydroxy-N-[2-((4-phenylbenzoyl)amino)ethyl]urea;
N-hydroxy-N-[2-((3-phenylmethyloxybenzoyl)amino)ethyl]urea;
N-hydroxy-N-[2-((5-phenoxyfuran-2-oyl)amino)ethyl]urea;
N-hydroxy-N-[2-(N-methyl-((3-(4-chlorophenoxy)phenyl)methyl)amino)ethyl]urea;
N-hydroxy-N-[2-(N-methyl-((3-(4-methoxyphenoxy)phenyl)ethyl)amino)ethyl]urea;
N-hydroxy-N-[2-(N-methyl((3-(3,4-dichlorophenoxy)phenyl)methyl)amino)ethyl]urea;
N-hydroxy-N-[2-(N-methyl-((3-(3,5-dichlorophenoxy)phenyl)methyl)amino)ethyl]urea;
N-hydroxy-N-[2-(((((4-methoxy-3-phenylmethoxy)phenyl)methyl)-N-methyl)amino)ethyl]urea;

(S)-N-hydroxy-N-[2-((tert-butoxycarbonyl)amino)propyl]urea;
(R)-N-hydroxy-N-[2-((tert-butoxycarbonyl)amino)propyl]urea;
N-hydroxy-N-[2-((tert-butoxycarbonyl)amino)ethyl]urea;
N-hydroxy-N-[(((3-(4-chlorophenoxy)phenyl)prop-2-enyl)amino)carbonyl)methyl]urea;
N-hydroxy-N-[2-((3-(1-methylethoxy)benzoyl)amino)ethyl]urea;
N-hydroxy-N-[2-((3-(2-methyl-prop-2-enyloxy)benzoyl)amino)ethyl]urea;
N-hydroxy-N-[2-((naphth-2-ylsulfonyl)amino)ethyl]urea;
N-hydroxy-N-[2-(((1 -(4-chlorophenylmethyl)pyrrol-2-yl)carbonyl)amino)ethyl]urea;
N-hydroxy-N-[2-(((3-(4-chlorophenoxy)benzoyl)-N-methyl)amino)propyl]urea;
N-hydroxy-N-[2-((2-phenoxybenzoyl)amino)ethyl]urea;
N-hydroxy-N-[2-((4-phenoxybenzoyl)amino)ethyl]urea;
N-hydroxy-N-[2-(3-((4-bromophenoxy)benzoyl)amino)ethyl]urea;
N-hydroxy-N-[2-(3-((4-fluorophenoxy)benzoyl)amino)ethyl]urea;
N-hydroxy-N-[2-((3-(pyrid-2-yloxy)benzoyl)amino)ethyl]urea;
N-hydroxy-N-[2-((3-phenoxyphenylacetyl)amino)ethyl]urea;
N-hydroxy-N-[2-((4-n-hexyloxybenzoyl)amino)ethyl]urea;
N-hydroxy-N-[2-((5-(4-chlorophenoxy)furan-2-oyl)amino)ethyl]urea;
N-hydroxy-N-[2-((4-(4-chlorothiophenoxy)thien-3-oyl)amino)ethyl]urea;
(S)-N-hydroxy-N-[2-((5-(4-chlorophenoxy)fur-2-oyl)amino)propyl]urea;
N-hydroxy-N-[2-((5-(4-chlorophenoxy)fur-2-oyl)amino)ethyl]urea;
N-hydroxy-N-[2-((3-(4-chlorophenylsulfonyl)benzoyl)amino)ethyl]urea;
N-hydroxy-N-[((benzo[b]furan-2-oyl)amino)ethyl]urea;
N-hydroxy-N-[((4-chlorobenzo[b]thien-2-oyl)amino)ethyl]urea;
N-hydroxy-N-[2-((3-benzoylbenzoyl)amino)ethyl]urea;
N-hydroxy-N-[2-((4-(1 -phenylethyloxy)benzoyl)amino)ethyl]urea;
N-hydroxy-N-[2-((3-(1-phenylethyloxy)benzoyl)amino)ethyl]urea;
N-hydroxy-N-[2-(((4-(1-phenylethyl)phenyl)propion-2-yl)amino)ethyl]urea;
N-hydroxy-N-[2-(((3-(1-phenylethyl)phenyl)propion-2-yl)amino)ethyl]urea;
N-hydroxy-N-[2-(((2-(1-phenylethyl)phenyl)propion-2-yl)amino)ethyl]urea;
N-hydroxy-N-[2-((3-phenoxyphenoxyacetyl)amino)ethyl]urea;
N-hydroxy-N-[2-((4-phenoxyphenoxyacetyl)amino)ethyl]urea;
N-hydroxy-N-[2-((2-phenoxyphenoxyacetyl)amino)ethyl]urea;
N-hydroxy-N'-methyl-N-[2-((quinolin-2-oyl)amino)ethyl]urea;
N-hydroxy-N-[2-((quinolin-2-oyl)amino)ethyl]urea;
N-hydroxy-N-[2-(((3-(6-methoxynaphth-2-yl)prop-2-en-2-yl)carbonyl)amino)ethyl]urea;
N-hydroxy-N-[2-((3-phenylpropionyl)amino)ethyl]urea;
N-hydroxy-N-[2-((3-(4-n-butoxyphenyl)prop-2-enoyl)amino)ethyl]urea;
N-hydroxy-N-[2-((3-(3-n-butoxyphenyl)prop-2-enoyl)amino)ethyl]urea;

N-hydroxy-N-[2-((3-(2-n-butoxyphenyl)prop-2-enoyl)amino)ethyl]urea;

N-hydroxy-N-[2-((2-(6-methoxynaphth-2-yl)propionyl)amino)ethyl]urea;

N-hydroxy-N-[2-((2-(4-(2-methylpropyl)phenyl)propionyl)amino)ethyl]urea;

N-hydroxy-N-[2-((2-(2,6-dichlorophenylamino)phenylacetyl)amino)ethyl]urea;

N-hydroxy-N-[2-((2-phenylthiazol-4-oyl)amino)ethyl]urea;

(d,l)-N-hydroxy-N-[3-((tert-butyoxycarbonyl)amino)prop-2-yl]urea;

N-hydroxy-N-[3-((5-(4-fluorophenoxy)furan-2-oyl)amino)prop-2-yl]urea;

N-hydroxy-N-[2-((2-(1-phenylethyloxy)benzoyl)amino)ethyl]urea;

N-hydroxy-N-[4-((5-(4-fluorophenoxy)furan-2-oyl)amino)but-2-yl]urea;

N-hydroxy-N-[2-((2-phenoxybenzoyl)amino)ethyl]urea;

N-hydroxy-N-2-[(3-(4-bromophenyl)propenoyl)amino]ethyl urea;

N-hydroxy-N-2-[(3-phenylpropenoyl)amino]ethyl urea;

(R)-N-hydroxy-N-[2-(3-(4-bromophenyl)propenoyl)amino] propyl urea;

(d,l)-N-hydroxy-N-[3-(3-(4-bromophenyl)propenoyl)amino]prop-2-yl urea;

N-hydroxy-N-[2-(3-(4-bromophenyl)propanoyl)amino] ethyl urea;

N-hydroxy-N-2-[(3-(3-(4-chlorophenoxy)phenyl)propynoyl)amino]ethyl urea;

N-hydroxy-N-2-[N"-benzyloxycarbonyl-((3-phenoxyphenyl)methyl)amino]ethyl urea;

N-hydroxy-N-2-[(3-phenoxyphenyl)methyl)amino]ethyl urea;

N-hydroxy-N-2-[(3-(3-(4-chlorophenoxy)phenyl)-trans-propenoyl)amino]ethyl urea;

N-hydroxy-N-2-[(3-(3-butyloxyphenyl)-trans-propenoyl)amino]ethyl urea;

N-hydroxy-N-2-[(3-(4-chlorophenoxy)phenyl)-3-methyl-transpropenoyl)amino] ethyl urea;

N-hydroxy-N-2-[(3-(4-bromophenyl)-2-methyl-trans-propenoyl)amino]ethyl urea;

N-hydroxy-N-2-[(3-(4-chlorophenoxy)phenyl)-2-methyl-transpropenoyl)amino] ethyl urea;

N-hydroxy-N-2-[(2-(3-(4-ethyloxyphenoxy)phenyl)-trans-cyclopropyl)carbonyl amino]ethyl urea;

(S)-N-hydroxy-N-[2-((2-(3-phenoxyphenyloxy)acetyl)amino)propyl]urea;

N-hydroxy-N-[2-((2-(3-phenoxyphenyloxy)propionyl)amino)ethyl]urea;

(d,l)-N-hydroxy-N-[3-(2-(3-(4-chlorophenoxy)phenyl)acetylamino)prop-2-yl]urea;

N-hydroxy-N-[3-(3-(4-chlorophenoxy)phenyl)propionyl)amino]prop-2-yl urea; and

N-hydroxy-N-5-[(3-phenoxybenzoyl)amino]-pent-3-yn-2-yl urea.

Preferred compounds of the present invention are

N-hydroxy-N-[2-((5-(4-chlorophenoxy)fur-2-oyl)amino)ethyl]urea;

(R)-N-Hydroxy-N-[2-((5-(4-chlorophenoxy)fur-2-oyl)amino)propyl]urea;

(S)-N-hydroxy-N-[2-((5-(4-chlorophenoxy)fur-2-oyl)amino)propyl]urea;

(R)-N-hydroxy-N-[3-((5-(4-fluorophenoxy)furan-2-oyl)amino)prop-2-yl]urea (S)-N-hydroxy-N-[3-((5-(4-fluorophenoxy)furan-2-oyl)amino)prop-2-yl]urea (R)-N-hydroxy-N-[3-((5-(4-fluorothiophenoxy)furan-2-oyl)amino)prop-2-yl]urea;

(S)-N-hydroxy-N-[3-((5-(4-fluorothiophenoxy)furan-2-oyl)amino)prop-2-yl]urea;

N-hydroxy-N-[2-((5-(4-methyl phenoxy)furan-2 -oyl)amino)ethyl]urea;

N-hydroxy-N-[2-((3-(4-chlorophenoxy)benzoyl)amino)ethyl]urea;

N-hydroxy-N-[(((3-phenoxyphenyl)amino)carbonyl)methyl]urea;

N-hydroxy-N-[2-((3-phenoxyphenylbenzoyl)amino)ethyl] urea;

N-hydroxy-N-[2-((4-butoxyphenylbenzoyl)amino)ethyl] urea; and

N-hydroxy-N-[2-((5-(4-chlorophenoxy)furan-2-oyl)amino)ethyl]urea;

with the compound N-hydroxy-N-[3-((5-(4-fluorophenoxy)furan-2-oyl)amino)prop- 2-yl]urea and its individual enantiomers and mixtures thereof being most preferred.

Certain compounds of this invention exist in stereoisomeric forms by virtue of the presence of one or more chiral centers. The present invention contemplates all such stereoisomers, including R- and S-enantiomers, diastereomers, and mixtures thereof as falling within the scope of the invention. If a particular enantiomer is desired, it may be prepared by chiral synthesis or by derivatization with a chiral auxiliary where the resulting diastereomeric mixture is separated and the auxiliary group cleaved to provide the pure desired enantiomers. Alternatively, where the molecule contains a basic functional group such as amino or an acidic functional group such as carboxyl diastereomeric salts are formed with an appropriate optically active acid or base, followed by resolution of the diastereomers thus formed by fractional crystallization or chromatographic means well known in the an and subsequent recovery of the pure enantiomers.

Certain compounds of the present invention may contain a basic functional group such as amino, alkylamino, or dialkylamino and are thus capable of forming salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, laurylsulphonate salts and the like. (See, for example S. M. Berge, et al., "Pharmaceutical Salts," *J. Pharm. Sci.*, 66:1–19 (1977) which is incorporated herein by reference.)

In other cases, the compounds may contain one or more acidic functional groups such as carboxyl and the like and are capable of forming salts with pharmaceutically acceptable bases. The term "pharmaceutically acceptable salts" in these instances refers to the relatively non-toxic, inorganic and organic base addition salts of compounds of the present invention. These salts can be likewise prepared in situ during the final isolation and purification of the compounds or by separately reacting the purified compound in its free acid form with a suitable base such as the hydroxide, carbonate or bicarbonate of a pharmaceutically acceptable metal cation or with ammonia, or an organic primary, secondary, or tertiary amine. Representative alkali or alkaline earth salts include the lithium, sodium, potassium, calcium, magnesium and aluminum salts and the like. Representative organic amines useful for the formation of base addition salts include ethylamine, diethylamine, ethylenediamine, ethanolamine, diethanolamine, piperazine, and the like. (See, for example S. M. Berge, et al., "Pharmaceutical Salts," *J. Pharm. Sci.*, 66:1–19 (1977) which is incorporated herein by reference.)

Lipoxygenase Inhibition Determination

Assays to determine 5-lipoxygenase inhibitory activity of representative compounds of the present invention were performed in 200 mL incubations containing the 20,000×g supernatant from 1.5 million homogenized HWBL-1 cells and various concentrations of the test compound. Reactions were initiated by addition of radiolabeled arachidonic acid and terminated by acidification and ether extraction. Reaction products were separated from nonconverted substrate by thin layer chromatography and measured by liquid scintillation spectroscopy. All incubations are performed in triplicate. Inhibition of 5-lipoxygenase activity was calculated as the ratio of the amount of product formed in the presence and absence of inhibitor. $IC_{50}$ values (concentration of compound producing 50% enzyme inhibition) were calculated by linear regression analysis of percentage inhibition versus log inhibitor concentration plots. (Dyer, R. D.; Haviv, F.; Hanel, A. M.; Bornemier, D. A.; Carter, G. W. Fed. Proc., *Fed. Am. Soc. Exp. Biol.* 1984, 43, 1462A). Results for compounds of the foregoing examples are indicated in Table 1.

TABLE 1

In Vitro Inhibitory Potencies of Compounds of this Invention Against 5-Lipoxygenase from HWBL-1 20,000xg Supernatant

| Example | $IC_{50}$ ($10^{-6}$ M) |
|---|---|
| 1 | 0.48 |
| 2 | 0.23 |
| 3 | 0.87 |
| 4 | 5.8 |
| 5, step 2 | 6.3 |
| 5, step 3 | 7.3 |
| 9 | 2.8 |
| 10 | 3.5 |
| 11 | 6.6 |
| 12 | 0.73 |
| 13 | 0.83 |
| 14 | 1.8 |
| 15 | 0.64 |
| 16 | 1.9 |
| 17 | 5.0 |
| 18 | 0.25 |
| 19 | 0.26 |
| 20 | 4.5 |
| 21 | 0.07 |
| 22 | 0.33 |
| 24 | 0.29 |
| 25 | 0.43 |
| 26 | 0.16 |
| 27 | 0.76 |
| 28 | 0.23 |
| 29 | 0.30 |
| 30 | 0.34 |
| 31 | 0.47 |
| 32 | 0.21 |
| 33 | 0.61 |
| 34 | 0.38 |
| 35 | 0.22 |
| 36 | 0.13 |
| 37 | 0.10 |
| 38 | 0.20 |
| 39 | 0.31 |
| 40 | 0.15 |

TABLE 1-continued

In Vitro Inhibitory Potencies of Compounds of this Invention Against 5-Lipoxygenase from HWBL-1 20,000xg Supernatant

| Example | $IC_{50}$ ($10^{-6}$ M) |
|---|---|
| 41 | 1.6 |
| 46 | 0.29 |
| 47 | 0.23 |
| 48 | 1.1 |
| 49 | 0.29 |
| 50 | 5.8 |
| 51 | 0.24 |
| 52 | 0.16 |
| 53 | 0.44 |
| 54 | 0.15 |
| 55 | 1.0 |
| 56 | 0.22 |
| 57 | 0.29 |
| 58 | 0.11 |
| 59 | 0.10 |
| 60 | 0.28 |
| 61 | 0.16 |
| 62 | 0.91 |
| 63 | 1.0 |
| 64 | 2.1 |
| 65 | 0.22 |
| 66 | 0.25 |
| 67 | 0.35 |
| 69 | 0.39 |
| 72 | 0.11 |
| 75 | 0.1 |
| 76 | 1.0 |
| 77 | 0.39 |
| 82 | 5.0 |
| 83 | 0.44 |
| 84 | 0.93 |
| 85 | 0.29 |
| 87 | 0.37 |
| 88 | 0.28 |

Inhibition of Leukotriene Biosynthesis

Inhibition of the biosynthesis of leuktrienes in vivo after oral administration of compound was determined using a rat peritoneal anaphylaxis model in a similar manner as that described by Young and coworkers (Young, P. R.; Dyer, R. D.; Carter, G. W. Fed. Proc., Fed. Am. Soc. Exp. Biol. 1985, 44, 1185). In this model rats were injected intraperitoneally (ip) with rabbit antibody to bovine serum albumin (BSA) and three hours later injected ip with BSA to induce an antgen-antibody response. Rats were sacrificed 15 minutes after this challenge and the peritoneal fluids were collected and analyzed for leukotriene levels. Test compounds were administered by gavage one hour prior to the antigen challenge. Percent inhibition values were determined by comparing the treatment group to the mean of the control group. From the results of this assay it is demonstrated that compounds of this invention are orally effective in preventing the in vivo biosynthesis of leukotrienes. The results are presented in Table 2.

TABLE 2

| | % Inhibition of Leukotrienes | | |
|---|---|---|---|
| Example | Oral Dose at 30 μmol/kg | Oral Dose at 50 μmol/kg | Oral Dose at 100 μmol/kg |
| 2 | — | — | 84 |
| 19 | — | — | 63 |
| 21 | — | — | 95 |
| 26 | — | — | 99 |
| 32 | — | — | 90 |

TABLE 2-continued

| | % Inhibition of Leukotrienes | | |
| --- | --- | --- | --- |
| Example | Oral Dose at 30 μmol/kg | Oral Dose at 50 μmol/kg | Oral Dose at 100 μmol/kg |
| 35 | — | — | 15 |
| 37 | — | — | 80 |
| 38 | — | — | 86 |
| 40 | — | — | 76 |
| 55 | — | — | 83 |
| 56 | — | — | 85 |
| 60 | — | — | 84 |
| 87 | — | — | 60 |
| 23 | 57 | — | — |
| 36 | 78 | — | — |
| 51 | 47 | — | — |
| 52 | 19 | — | — |
| 53 | 33 | — | — |
| 54 | 11 | — | — |
| 63 | 52 | — | — |
| 64 | 92 | — | — |
| 73 | 53 | — | — |
| 88 | 84 | — | — |
| 58 | — | 81 | — |
| 61 | — | 60 | — |

Preparation of Compounds of this Invention

The compounds of this invention can be prepared from the appropriate starting substituted aryl amines or acids as is illustrated in Schemes I–III. The synthesis of the aniline-derived amide-linked N-hydroxy ureas of this invention begins with the acylation of the desired aryl amine (I) with bromoacetyl bromide. The resulting α-halo amide was then treated with anhydrous sodium acetate in refluxing absolute ethanol to provide the α-acetoxy amide which was convened to the corresponding alcohol (II) with aqueous sodium hydroxide at ambient temperature. The alcohol was convened to the diprotected N-hydroxyl amine (III) utilizing a modified Mitsunobu procedure (Maurer, P. J.; Miller, M. J. *J. Am. Chem. Soc.*, 1982, 104, 3096) with N,O-bis-t-butyloxycarbonyl hydroxylamine (Carpino, L. A.; et. al. *J. Am. Chem. Soc.*, 1959, 81, 955). Deprotection provides the hydroxylamine intermediate which is convened to the desired N-hydroxy urea by treatment with trimthylsilyl isocyanate in an anhydrous, aprotic solvent.

The aryl acid (V) derived amide-linked N-hydroxy ureas are prepared according to the sequence described in Scheme II. Conversion of the starting acid to the corresponding β-hydroxy amide (VI) was achieved through acylation of the corresponding acid chloride with ethanol amine. The hydroxyamide was converted via a modified Mitsunobu process to obtain the diprotected N-hydroxyl amine (VII) which was deprotected and converted to the desired aryl acid derived amide-linked N-hydroxy urea (VIII) as described in Scheme I.

SCHEME I

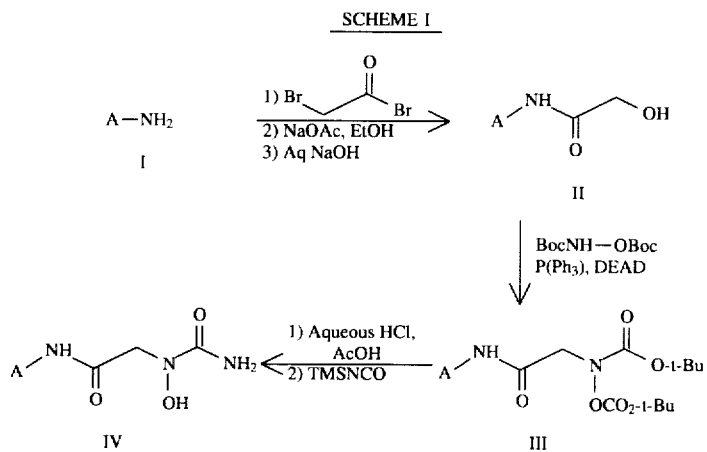

SCHEME II

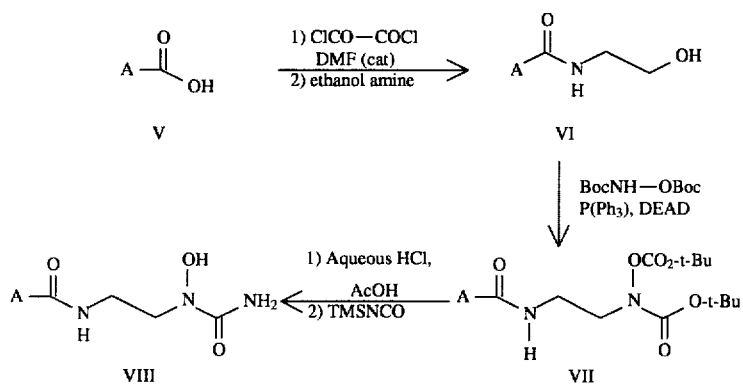

Alternately, compounds of this invention can be prepared by the general method outlined in Scheme III. A BOC-protected aminoalcohol (IX) is converted to the corresponding N-hydroxyurea (XII) by oxidizing to the aldehyde, oxime formation, reduction to the hydroxylamine, and treatment with TMSNCO. The N-hydroxyurea is then selectively O-acylated to give (XIII) which is deprotected under acidic conditions (TFA) and neutralized to permit the O- to N-rearrangement providing the desired hydroxyurea products (XIV).

and the appropriate aminoalcohol (X). The resulting aryl aminoalcohol (XVI) was then transformed into the desired amino-linked N-hydroxy urea (XVIII) following the previously described modified mitsunobu, deprotection, and isocyanate treatment as described in Scheme I.

SCHEME III

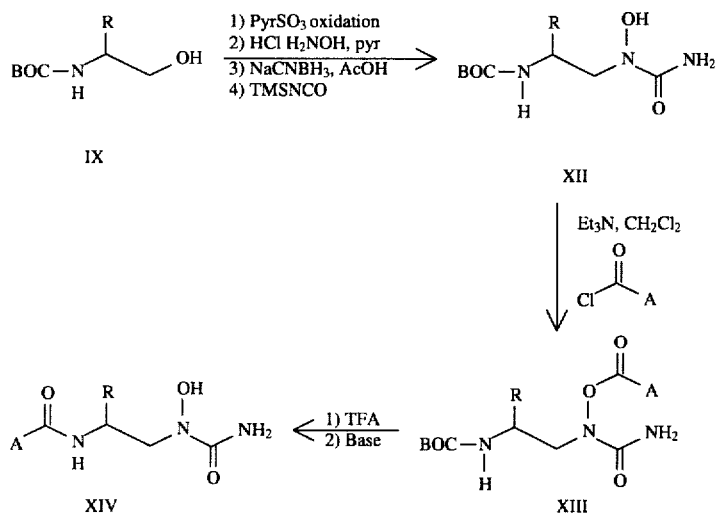

Synthesis of amine linked N-hydroxy ureas is outlined in Scheme IV. The sequence was initiated by carrying out a reductive amination between the desired aryl aldehyde (XV)

SCHEME IV

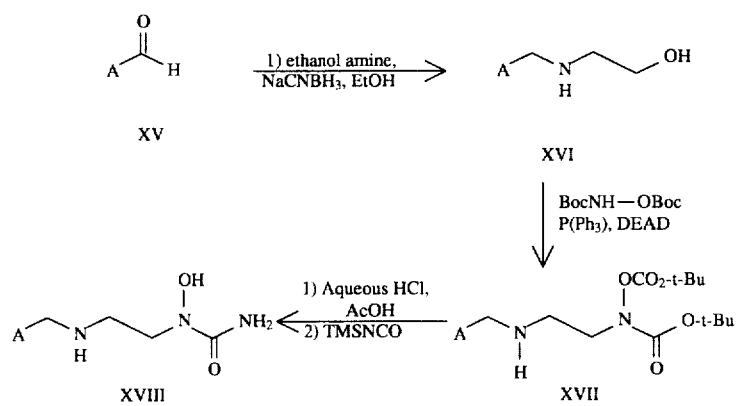

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carders, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in rum, may depend upon crystal size and crystalline form. Alteratively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the an to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

EXAMPLE 1

Preparation of
N-Hydroxy-N-[(((3-phenoxyphenyl)amino)carbonyl)-methyl]urea

A solution of m-phenoxyaniline (6.12 g, 32.4 mmol) and triethylamine (3.7 mL, 42.1 mmol) in anhydrous ether (100 mL) was cooled to −23° C. under a nitrogen atmosphere. To this solution was added bromoacetyl bromide (6.8 mL, 48.6 mmol) in anhydrous ether (30 mL). The reaction was stirred for 1 h at −23° C. and diluted with ethyl acetate (500 mL). The resulting solution was washed sequentially (1×, 10% aqueous HCl; 1× saturated $NaHCO_3$; 1× brine), dried ($Na_2SO_4$), filtered, and concentrated in vacuo to provide the α-bromoamide (10.05 g, 101%) as a red-brown solid which was best utilized without further purification.

The α-bromoamide (5.39 g, 17.6 mmol) was heated at reflux in 95% ethanol with sodium acetate (4.33 g, 52.8 mmol) and checked for completion via thin layer chromatography. The reaction mixture was cooled and treated with aqueous sodium hydroxide (1.06 g, 26.4 mmol). The volatiles were removed in vacuo anti the resulting slurry was diluted with brine (500 mL) and extracted (2×, EtOAc). The combined organic extracts were washed (1×, brine), dried ($Na_2SO_4$), filtered, and concentrated in vacuo to provide the α-hydroxy amide as a thick, dark brown, oil. Chromatographic purification (100 g silica gel, 20% $EtOAc:CHCl_3$) provided a light brown solid(3.46 g, 81%) which was recrystallized from EtOAc:Hexanes to provide an analytical sample. m.p. 152.5°–154° C.

The resulting hydroxy amide (0.50 g, 2.06 mmol), triphenylphosphine (0.70 g, 2.67 mmol), and N,O-bis-t-butyloxycarbonyl hydroxylamine (0.56 g, 2.47 mmol) were dissolved in anhydrous tetrahydrofuran (THF) (5 mL) and cooled to 0° C. To this solution was added diethylazodicarboxylate (DEAD)(0.42 mL, 2.67 mmol) in anhydrous THF (3 mL). The reaction was stirred at 0° C. for 1 h and the volatiles removed in vacuo. Chromatographic purification (100 g silica gel, 25% EtOAc:Hex) provided the bis-protected α-N-hydroxylamino amide (0.503 g, 53%) as a colorless foam.

The deprotection was carried out by dissolving the hydroxylamino amide 0.463 g, 1.01 mmol) in glacial acetic acid (4 mL) and adding 6N aqueous hydrochloric acid (1.7 mL, 10.1 mmol) and stirring for one hour at ambient temperature. The pH of the reaction was adjusted to −10 by first adding 15% aqueous sodium hydroxide to pH=7, then adding saturated sodium carbonate until the desired pH was achieved. The resulting cloudy aqueous solution was extracted (2×, EtOAc). The combined organic extracts were washed (1×, brine), dried ($Na_2SO_4$), filtered, and concentrated in vacuo to provide the deprotected hydroxyl amine (0.26 g, 100%). Without further purification, hydroxyl amine was dissolved in anhydrous THF (5 mL) and treated with trimethylsilyl isocyanate (273 mmol, 2.0 mmol). The reaction was judged complete by thin layer chromatography after 1 h and quenched by adding excess aqueous hydrochloric acid (5 mL 10% HCl). The two-phased solution was partitioned between brine and EtOAc. The organic layer was drawn off and washed (1×, brine), dried ($Na_2SO_4$), filtered, and concentrated in vacuo to provide the title compound. Recrystallization from acetone/methanol provided an analytical sample (0.15 g, 49%). m.p. 182.5°–184° C. with decomposition; $^1$H NMR (300 MHz, DMSO-$d_6$); 9.87 (1H, s), 9.46 (1H, s), 7.27–7.43 (5H, m), 7.15 (1H, t, J=7 Hz), 7.03 (2H, t, J=7 Hz), 6.73 (2H, s), 6.25 (1H, m), 6.40 (2H, s), 4.11 (2H, s); MS (M+H)$^+$=302, (M+NH$_4$)$^+$= 319. Analysis calc'd for $C_{15}H_{15}N_3O_4$: C, 59.80 H, 5.02; N, 13.95; Found: C, 59.85; H, 5.08; N, 14.00.

EXAMPLE 2

Preparation of N-Hydroxy-N-[2-((3-phenoxyphenylbenzoyl)amino)ethyl]urea

A solution of m-phenoxybenzoic acid (6.06 g, 28.29 mmol)in anhydrous THF (90 mL) was cooled to 0° C. under a nitrogen atmosphere. To this solution was added a catalytic amount of dimethylformamide (DMF) (3 drops) and oxalyl chloride (4.94 mL, 56.58 mmol) in dichloromethane (20 mL). After complete addition, the cooling bath was removed, the reaction was stirred for 1 h, the volatiles were removed in vacuo, and the residue was dissolved in chloroform (100 mL) and concentrated in vacuo (three cycles) to provide the corresponding acid chloride which was used without further purification.

To a solution of ethanol amine (3.42 mL, 56.58 mmol) and triethylamine (5.92 mL, 47.44 mmol) in dichloromethane (90 mL) was added the acid chloride in dichloromethane (20 mL). The reaction was stirred at ambient temperature for 0.5 h and poured into 10% aqueous HCl. The resulting two-phased solution was extracted (2×, dichloromethane). The combined organic extracts were washed sequentially (1×, saturated NaHCO$_3$; 1×, brine), dried (MgSO$_4$), filtered and concentrated in vacuo to provide the corresponding amide (8.20 g, 113%) as a thick oil which was used without further purification.

Following the procedure for the conversion of Example 1 but using amide prepared above (3.04 g, 14.19 mmol), the desired di-protected N-hydroxylamine (3.85 g, 57%) was obtained after chromatographic purification (250 g silica gel, 20% EtOAc: Hex).

Deprotection of the di-protected N-hydroxylamine (11.94 g, 25.2 mmol) and treatment of the resulting N-hydroxylamine with TMSNCO as described above provided the title compound (3.55 g, 45%) after recrystallization from methanol:EtOAc. m.p. 182.5°–184° C. with decomposition; $^1$H NMR (300 MHz, DMSO-$d_6$); 9.82 (1H, s), 8.52 (1H, t, J=5 Hz),7.61 (1H, dt, J=8,1,1), 7.38– 7.52 (4H, m), 7.18 (2H, m), 7.03 (2H, dq, J=7,1,1,1, Hz), 6.33 (2H, s), 3.37– 3.53 (4H, m); MS (M+H)$^+$=316, (M+NH$_4$)$^+$=333. Analysis calc'd for $C_{16}H_{17}N_3O_4$: C, 60.95 H, 5.43; N, 13.33; Found: C, 60.90; H, 5.45; N, 13.31.

EXAMPLE 3

Preparation of N-Hydroxy-N-[(((3-phenylmethoxyphenyl)amino)carbonyl)methyl] urea The title compound was obtained following the procedures described in Example 1, but employing 3-benzyloxyaniline in lieu of 3-phenoxyaniline. m.p. 177°–178° C. with decomposition; $^1$H NMR (300 MHz, DMSO-$d_6$); 9.82 (1H, s), 8.52 (1H, t, J=5 Hz),7.61 (1H, dt, J=8,8,1,1,1), 7.38–7.52 (4H, m), 7.18 (2H, m), 7.03 (2H, dq, J=7,7,1,1,1, Hz), 6.33 (2H, s), 3.37–3.53 (4H, m); MS (M+H)$^+$=316, (M+NH$_4$)$^+$= 333. Analysis calc'd for $C_{16}H_{17}N_3O_4C$, 60.95 H, 5.43; N, 13.33; Found: C, 60.90; H, 5.45; N, 13.31.

EXAMPLE 4

Preparation of N-Hydroxy-N-[((N-methyl-(3-phenoxyphenyl)amino)carbonyl)methyl]urea Step 1: Preparation of N-Methyl 4-phenoxyaniline A solution of 4-phenoxyaniline (10 g, 54.0 mmol) and ethyl formate (22 mL, 270 mmol) in toluene (200 mL) were heated at reflux for 18 h and the volatiles were removed in vacuo to provide the corresponding formamide derivative. The resulting oil was dissolved in anhydrous THF (115 mL) and added in a dropwise fashion to a suspension of lithium aluminum hydride (2.05 g, 108 mmol) in THF; the addition rate was adjusted to maintain a steady reflux. The reaction was refluxed for 1 h after complete addition of the formamide, cooled to ambient temperature, and quenched by the sequential addition of H$_2$O (2.05 mL), 15% aqueous NaOH (2.05 mL), and H$_2$O (6.15 mL). The resulting slurry was stirred for 1 h and filtered through a celite pad. The filtrate was dried (Na$_2$SO$_4$), filtered and concentrated in vacuo to provide the title aniline as an oil which was employed without further purification. $^1$H NMR (300 MHz, CDCl$_3$); 7.23–7.31 (2H, m), 6.90–7.03 (5H, m), 6.60(2H, d, J=9 Hz),ca. 3.62 (1H, br s), 2.83(3H, s); MS (M+H)$^+$=200, (M+NH$_4$)$^+$=217.

Step 2: Preparation of N-Hydroxy-N-[((N-methyl-(3-phenoxyphenyl)amino)carbonyl)methyl]urea The title compound was obtained following the procedures described in Example 1, but employing the 4-phenoxyaniline, prepared in step 1, above in lieu of 3-phenoxyaniline. m.p. 147°–148° C.; $^1$H NMR (300 MHz, DMSO-$d_6$); 9.02 (1H, s), 7.43 (2H, t, J=7.5 Hz),7.34 (2H, t, J=7.5 Hz), 7.18 (1H, t, J=7 Hz), 7.05 (4H, br t, J=7.5 Hz), 6.27 (2H, s), 3.87 (2H, br s), 3.16 (3H, br s); MS (M+H)$^+$=316, (M+NH$_4$)$^+$=333. Analysis calc'd for $C_{16}H_{17}N_3O_4$: C, 60.95 H, 5.43; N, 13.33; Found: C, 60.62; H, 5.48; N, 13.24.

EXAMPLE 5

Preparation of N-Hydroxy-N-[((N-methyl-(3-phenoxyphenyl)amino)carbonyl)methyl]urea and N-Hydroxy-N'methyl-N-[((N-methyl-(3-phenoxyphenyl)amino)carbonyl)methyl]urea Step 1: Preparation of N-Methyl-3-phenoxyaniline The title compound was obtained following the procedures described in Example 4, step 1, but employing 3-phenoxyaniline in lieu of 4-phenoxyaniline. $^1$H NMR (300 MHz, CDCl$_3$); 7.25–7.37(2H, m), 7.00–7.14 (4H, m), 6.27–6.38(3H, m),ca. 3.73 (1H, br s), 2.80(3H, s); MS (M+H)$^+$= 200, (M+NH$_4$)$^+$ =217.

Step 2; Preparation of N-Hydroxy-N-[((N-methyl-(3-phenoxyphenyl)amino)carbonyl)methyl]urea The title compound was obtained following the procedures described in Example 1, but employing the product of step 1, above. m.p. 109.5°–112° C.; $^1$H NMR (300 MHz, DMSO-$d_6$); 9.23 (1H, s), 7.39–7.47 (3H, m),7.02–7.22 (6H, m), 6.28 (2H, s), 3.92 (2H, br s), 3.18 (3H, br s); MS $(M+H)^+=316$, $(M+NH_4)^+=333$. Analysis calc'd for $C_{16}H_{17}N_3O_4$: C, 60.95 H, 5.43; N, 13.33; Found: C, 60.68; H, 5.44; N, 13.30.

Step 3: Preparation of N-Hydroxy-N'-methyl-N-[((N-methyl-(3-phenoxyphenyl)amino)carbonyl)methyl]urea The title compound was obtained following the procedures described in step 2, above but employing N-methyl isocyanate (Me-NCO) in lieu of TMSNCO to provide the title compound as an amorphous solid. $^1$H NMR (300 MHz, DMSO-d$_6$); 9.18 (1H, s), 7.39–7.47 (3H, m),6.93–7.22 (6H, m), 6.79 (1H, br q, J=5 Hz), 3.93 (2H, br s), 3.18 (3H, br s), 2.58 (3H, d, J=5 Hz); MS $(M+H)^+= 330$, $(M+NH_4)^+=347$. Analysis calc'd for $C_{17}H_{19}N_3O_4(0.50\ H_2O)$: C, 60.34 H, 5.96; N, 12.41; Found: C, 60.85; H, 5.77; N, 12.05.

EXAMPLE 6

Preparation of N-Hydroxy-N-[((N-phenylmethyl-(4-bromophenyl)-amino)carbonyl)methyl]urea Step 1: Preparation of N-Benzyl 4-bromoaniline A solution of BH$_3$THF complex (54.4 mL, 54.4 mmol) was added slowly to a solution of N-benzoyl-4-bromoaniline (5.04 g, 18.3 mmol) in anhydrous THF. The resulting solution was slowly brought to reflux and maintained at reflux for 1.5 h. After cooling to ambient temperature, 1M HCl in methanol (54 mL) was added and the resulting mixture heated at reflux for 1 h. The reaction was cooled, poured into 10% HCl, and extracted (1×, Et$_2$O). The aqueous layer was basified to pH~12 by adding concentrated ammonium hydroxide and extracted (2×, EtOAc). The combined organic extracts were washed (1×, brine), dried (Na$_2$SO$_4$), filtered, and concentrated in vacuo to provide the benzyl bromoaniline as a waxy brown solid. Chromatographic purification (150 g silica gel, 10% EtOAc:Hex) provided the product (2.7 g, 56%) as a light red solid. m.p. 49° C.; $^1$H NMR (300 MHz, CDCl$_3$); 7.25–7.39 (5H, m), 7.23(2H, d, J=9 Hz), 6.50 (2H, d, J=9 Hz), 4.31 (2H, d, J=5 Hz), 4.18 (1H, br s); MS $(M+H)^+=262/264$.

Step 2: Preparation of N-Hydroxy-N-[((N-phenylmethyl)-(4-romophenyl)amino)carbonyl)methyl]urea The title compound was obtained following the procedures described in Example 1, but employing the product from step 1, above in lieu of 3-phenoxyaniline. m.p. softens at 86° C. and melts at 88°–89° C.; $^1$H NMR (300 MHz, DMSO-d$_6$); 9.31 (1H, s), 7.56 (2H, d, J=8 Hz), 7.13–7.32 (7H, m), 6.31 (2H, s), 4.86 (2H, br s), 3.92 (2H, br s); MS $(M+H)^+=378/380$, $(M+NH_4)^+=395/397$. Analysis calc'd for $C_{16}H_{16}N_3O_3Br(0.50\ H_2O)$: C, 49.62 H, 4.42; N, 10.85; Found: C, 49.93; H, 4.42; N, 10.85.

EXAMPLE 7

Preparation of N-Hydroxy-N-[((N-thien-2-ylmethyl-(4-bromophenyl)-amino)carbonyl)methyl]urea The title compound was obtained following the procedures described in Example 1, but employing N-(2-thienyl)methyl-4-bromoaniline (prepared as described in example 6, step 1 above from the corresponding amide of 4-bromoaniline) in lieu of 3-phenoxyaniline. m.p. 94°–98° C.; $^1$H NMR (300 MHz, DMSO-d$_6$); 9.31 (1H, s), 7.61 (2H, d, J=9 Hz), 7.42 (1H, dd, J=5,1 Hz), 7.13 (2H, d, J=9 Hz),6.90 (1H, dd, J=5,3 Hz), 6.83 (1H, br s), 6.31 (2H, s), 4.96 (2H, br s), 3.86 (2H, br s); MS $(M+H)^+=384/386$, $(M+NH_4)^+=401/403$. Analysis calc'd for $C_{14}H_{14}N_3O_3BrS(0.50\ H_2O)$: C, 42.76 H, 3.84; N, 10.68; Found: C, 43.11; H, 3.76; N, 10.25.

EXAMPLE 8

Preparation of N-Hydroxy-N'-methyl-N-[((N-thien-2-ylmethyl-(4-bromophenyl)amino)-carbonyl)methyl]urea The title compound was obtained following the procedures described in Example 7, but employing Me-NCO in lieu of TMS-NCO. m.p. 76°–79.5° C.; $^1$H NMR (300 MHz, DMSO-d$_6$); 9.24 (1H, s), 7.61 (2H, d, J=9 Hz), 7.42 (1H, dd, J=5,1 Hz), 7.13 (2H, d, J=9 Hz),6.90 (1H, dd, J=5,3 Hz), 6.83 (1H, br s), 4.98 (2H, br s), 3.84 (2H, br s), 2.57 (3H, d, J=5 Hz); MS $(M+H)^+= 398/400$, $(M+NH_4)^+=415/417$. Analysis calc'd for $C_{15}H_{16}N_3O_3BrS(0.25\ H_2O)$: C, 44.73; H, 4.13; N, 10.43; Found: C, 45.28; H, 4.34; N, 9.66.

EXAMPLE 9

Preparation of N-Hydroxy-N-[((N-methyl-(3-phenylmethoxyphenyl)-amino)carbonyl)methyl]urea The title compound was obtained following the procedures described in Example 1, but employing N-methyl-3-benzyloxyaniline (prepared from the corresponding aniline as described in example 3) in lieu of 3-phenoxyaniline. m.p. 162°–163° C.; $^1$H NMR (300 MHz, DMSO-d$_6$); 9.22 (1H, s), 7.33–7.50 (6H, m), 6.98–7.05 (2H, m), 6.91 (2H, br d, J=7.5 Hz), 6.28 (2H, s), 5.13 (2H, s), 3.91 (2H, br s), 3.07 (3H, s); MS $(M+H)^+=330$. Analysis calc'd for $C_{17}H_{19}N_3O_4$ (0.25 H$_2$O): C, 61.16; H, 5.89; N, 12.58; Found: C, 61.36; H, 5.86; N, 12.54.

EXAMPLE 10

Preparation of N-Hydroxy-N-[(((4-phenoxyphenyl)amino)carbonyl)-methyl]urea

The title compound was obtained following the procedures described in Example 1, but employing 4-phenoxyaniline in lieu of 3-phenoxyaniline. m.p. 189.5°–190.5° C.; $^1$H NMR (300 MHz, DMSO-d$_6$); 9.72 (1H, s), 9.53 (1H, s),8.52 (1H, t, J=5 Hz),7.64 (2H, d, J=9), 7.36 (2H, dd, J=8, 9 Hz), 7.17 (1H, t, J=9 Hz), 6.94 (4H, d, J=9 Hz), 6.42 (2H, s), 4.17 (2H, s); MS $(M+H)^+= 302$, $(M+NH_4)^+=319$. Analysis calc'd for $C_{15}H_{15}N_3O_4$: C, 59.80; H, 5.02; N, 13.95; Found: C, 59.74; H, 5.01; N, 13.87.

EXAMPLE 11

Preparation of N-Hydroxy-N-[(((trans-4-(4-bromophenyl)but-3-en-2-yl)amino)carbonyl)methyl]urea The title compound was obtained following the procedures described in Example 1, but employing trans-2-amino-4-(4-bromophenyl)but-3-ene in lieu of 4-phenoxyaniline. The starting amine was prepared according to the method of Dellaria (Dellaria, J. F.; Sallin, K. J. *TetrahedronLett.* 1990, 31, 2661) m.p. 171°–172° C.; $^1$H NMR (300 MHz, DMSO-d$_6$); 9.42 (1H, s), 7.76 (1H, d, J=8 Hz), 7.52 (2H, d, J=8 Hz), 7.37 (2H, d, J=8 Hz), 6.42–6.48 (2H, m), 6.31 (1H, dd, J=16, 5.5 Hz), 4.53 (1H, sextet, J=6.5 Hz), 3.97(2H, s), 1.24 (3H, d, J=6.5 Hz); MS $(M+H)^+=342/344$, $(M+NH_4)^+=359/361$. Analysis calc'd for $C_{13}H_{16}N_3O_3Br$: C, 45.63; H, 4.71; N, 12.28; Found: C, 45.89; H, 4.70; N, 11.61.

EXAMPLE 12

Preparation of
N-Hydroxy-N-[(((trans,4-(3-phenoxyphenyl)but-3-en-2-yl)amino)carbonyl)methyl]urea The title compound was obtained following the procedures described in Example 1, but employing trans-2-amino-4-(3-phenoxyphenyl)but-3-ene in lieu of 4-phenoxyaniline. The starting amine was prepared according to the method of Dellaria (Dellaria, J. F.; Sallin, K. J. *Tetrahedron Lett.* 1990, 31, 2661). m.p. 150°–151° C.; $^1$H NMR (300 MHz, DMSO-$d_6$); 9.40 (1H, s), 7.74 (1H, d, J=7.5 Hz), 7.30–7.42 (3H, m), 7.10–7.22 (2H, m), 6.97–7.07 (3H, m), 6.88 (1H, dd, J=8, 2 Hz), 6.47 (1H, d, J=15.5 Hz), 6.43 (2H, s), 6.27 (1H, dd, J=15.5, 6 Hz),4.53 (1H, sextet, J=6.5 Hz) 3.97(2H, s), 1.24 (3H, d, J=6.5 Hz); MS (M+H)$^+$=356, (M+NH$_4$)$^+$=373. Analysis calc'd for $C_{19}H_{21}N_3O_4$: C, 64.21; H, 5.96; N, 11.82; Found: C, 64.29; H, 6.04; N, 11.80.

EXAMPLE 13

Preparation of
N-Hydroxy-N-[(((cis-4-(4-bromophenyl)but-3-en-2-yl)amino)carbonyl)methyl]urea The title compound was obtained following the procedures described in Example 1, but employing cis-2-amino-4-(3-phenoxyphenyl)but-3-ene in lieu of 4-phenoxyaniline. The starting amine was prepared according to the method of Dellaria (Dellaria, J. F.; Sallin, K. J. *Tetrahedron Lett.* 1990, 31, 2661) m.p. 142°–143° C.; $^1$H NMR (300 MHz, DMSO-$d_6$); 9.37 (1H, s), 7.78 (1H, d, J= 7.5), 7.42 (1.25H, AB, J=8.5 Hz), 7.37 (1.25H, AB, J=8.5 Hz), 7.10–7.18 (2H, m), 7.04 (1.5H, d, J=8.0 Hz), 6.87–6.95 (2H, m), 6.41 (2H, s), 6.38 (1H, d, J=12 Hz), 5.59 (1H, dd, J=12, 10 Hz), 4.83 (1H, br sextet, J=6.5 Hz) 3.90(2H, s), 1.15 (3H, d, J=6.5 Hz); MS (M+H)$^+$=356, (M+NH$_4$)$^+$=373. Analysis calc'd for $C_{19}H_{21}N_3O_4$: C, 64.21; H, 5.96; N, 11.82; Found: C, 63.81; H, 5.87; N, 11.61.

EXAMPLE 14

Preparation of
N-Hydroxy-N-[2-(((4-bromophenylacetyl)-N-methyl)-amino)ethyl]urea The title compound was obtained following the procedures described in Example 2, but employing 4-bromophenylacetate in lieu of 3-phenoxybenzoate and N-methylethanolamine in lieu of ethanolamine. m.p. 134°–135° C.; $^1$H NMR (300 MHz, DMSO-$d_6$); 9.48 (0.5H, s), 9.13 (0.5H, s), 7.46 (2H, d, J=8 Hz), 7.16 (2H, d, J=8 Hz), 7.37 (2H, d, J=8 Hz), 6.38 (1H, s), 6.29 (1H, s), 3.68 (2H, d J=13.5 Hz), 3.50 (2H, dd, J=13.5,4.5 Hz), 3.44 (2H, s), 3.0 (1.5H, s), 2.8 (1.5H, s); MS (M+H)$^+$=330/332, (M+NH$_4$)$^+$=347/349. Analysis calc'd for $C_{12}H_{16}N_3O_3Br$: C, 43.65; H, 4.88; N, 12.73; Found: C, 44.02; H, 4.94; N, 12.59.

EXAMPLE 15

Preparation of
N-Hydroxy-N-[(N-methyl-(3-phenoxyphenylbenzoyl)-amino)ethyl]urea

The title compound was obtained following the procedures described in Example 2, but employing N-methylethanolamine in lieu of ethanolamine to provide a viscous oil. $^1$H NMR (300 MHz, DMSO-$d_6$); 9.23 (1H, s), 7.38–7.48 (3H, m), 7.09–7.21 (2H, m), 6.90–7.07 (4H, m), 6.29 (2H, s), 3.60 (3H, br s), 3.45 (1H, br s), 2.93 (1.5H, br s), 2.87 (1.5H, br s); MS (M+H)$^+$=330, (M+NH$_4$)$^+$ =347 Analysis calc'd for $C_{17}H_{19}N_3O_4$ (0.25 H$_2$O): C, 61.16 H, 5.89; N, 12.59; Found: C, 60.77; H, 5.88; N, 12.39.

EXAMPLE 16

Preparation of
N-Hydroxy-N-[2-((3-methoxybenzoyl)amino)ethyl]urea

The title compound was obtained following the procedures described in Example 2, but employing 3-methoxybenzoate in lieu of 3-phenoxybenzoate. m.p. 149°–150° C.: $^1$H NMR (300 MHz, DMSO-$d_6$); 9.33 (1H, s), 8.46 (1H, br t, J=4.5 Hz), 7.33–7.42 (3H, m), 7.07 (1H, dt, J=8, 2.5, 2.5 Hz), 6.33 (2H, s), 3.71 (3H, s), 3.50 (2H, m), 3.45 (2H, m); MS (M+H)$^+$=254, (M+NH$_4$)$^+$ =271; Analysis calc'd for $C_{11}H_{15}N_3O_4$: C, 52.17; H, 5.97; N, 16.59; Found: C, 51.95; H, 5.87; N, 16.18.

EXAMPLE 17

Preparation of
N-Hydroxy-N-[2-((4-methoxybenzoyl)amino)ethyl]urea

The title compound was obtained following the procedures described in Example 2, but employing 4-methoxybenzoate in lieu of 3-phenoxybenzoate. m.p. 136°–138° C.: $^1$H NMR (300 MHz, DMSO-$d_6$); 9.33 (1H, s), 8.34 (1H, br t, J=4.5 Hz), 7.80 (2H, d, J=9.5), 6.98 (2H, d, J=9.5), 6.32 (2H, s), 3.81 (3H, s), 3.48 (2H, m), 3.41 (2H, m); MS (M+H)$^+$=254, (M+NH$_4$)$^+$=271; Analysis calc'd for Analysis calc'd for $C_{11}H_{15}N_3O_4$: C, 52.17; H, 5.97; N, 16.59; Found: C, 51.96; H, 5.98; N, 16.09.

EXAMPLE 18

Preparation of
N-Hydroxy-N-[2-((4-butoxybenzoyl)amino)ethyl]urea

The title compound was obtained following the procedures described in Example 2, but employing 4-butoxybenzoate in lieu of 3-phenoxybenzoate. m.p. 156°–157° C.: $^1$H NMR(300MHz, DMSO-$d_6$); 9.33(1H, s),8.32(1H, br t, J=4.5 Hz), 7.78 (2H, d, J=9.5), 6.98 (2H, d, J=9.5), 6.33 (2H, s), 4.03 (2H, t, J=6 Hz), 3.48 (2H, m), 3.41 (2H, m), 1.71 (2H, pentet, J=8 Hz), 1.45 (2H, sextet, J=8 Hz), 0.94 (3H, t, J=8 Hz); MS (M+H)$^+$=296; Analysis calc'd for $C_{14}H_{21}N_3O_4$: C, 56.94; H, 7.17; N, 13.84; Found: C, 56.59; H, 7.14; N, 13.84.

EXAMPLE 19

Preparation of
N-Hydroxy-N-[((3-butoxybenzoyl)amino)ethyl]urea 3-butoxybenzoate was prepared by adding ethyl 3-hydroxybenzoate (15 g, 90.3 mmol) and N-butyliodide (20.5 mL, 180.5 mmol) in THF (300 mL) to an ambient temperature THF (500 mL) solution of NaH (97%, 3.35 g, 135.4 mmol) under an nitrogen atmosphere. To the resulting soution was added hexamethylphosphoramide (HMPA, 31.5 mL, 180.5 mmol). The reaction was heated at relux for 1 h, cooled to ambient temperature and the volatiles removes under vacuum. The resulting oil was dissolved in ethanol (300 mL) and sodium hydroxide (3.6 g, 180.5 mmol) was added in water (100 mL); the hydrolysis of the ester was complete after 1 h at ambient temperature. The volatiles were removed under vacuum and the resulting slurry acidified to pH=2 with 10% aqueous HCl and extracted (2×, EtOAc). The combined organic extracts were washed (1×, brine), dried ($Na_2SO_4$), filtered, and concentrated in vacuo to provide a light yellow solid. The title compound was obtained following the procedures described in Example 2, but employing the 3-butoxybenzoate in lieu of 3-phenoxybenzoate. m.p. 153.5°–154.5° C.: $^1$H NMR (300 MHz, DMSO-$d_6$); 9.32 (1H, s), 8.43 (1H, br t, J=4.5 Hz), 7.33–7.42 (3H, m), 7.07 (1H, dt, J=8, 2.5, 2.5 Hz), 6.33 (2H, s), 4.01 (2H, t, J=6 Hz), 3.48 (2H, m), 3.43 (2H, m), 1.71 (2H, br pentet, J=8 Hz), 1.45 (2H, br sextet, J=8 Hz), 0.94 (3H, t, J=8 Hz); MS (M+H)$^+$=296, (M+NH$_4$)$^+$=313(weak); Analysis calc'd for $C_{14}H_{21}N_3O_4$: C, 56.94; H, 7.17; N, 13.84; Found: C, 56.88; H, 7.17; N, 14.16.

EXAMPLE 20

Preparation of N-Hydroxy-N-[2-((4-chlorobenzoyl)amino)ethyl]urea

The title compound was obtained following the procedures described in Example 2, but employing 4-chlorobenzoate in lieu of 3-phenoxybenzoate. m.p. 172°–173° C.: $^1$H NMR (300 MHz, DMSO-$d_6$); 9.33 (1H, s), 8.46 (1H, br t, J=4.5 Hz), 7.83 (2H, d, J=7.5), 7.53 (2H, d, J=7.5), 6.32 (2H, s),3.50 (2H, m), 3.43 (2H, m); MS (M+H)$^+$=254, (M+NH$_4$)$^+$ =271; Analysis calc'd for Analysis calc'd for $C_{10}H_{12}N_3O_3Cl(0.20\ H_2O)$: C, 45.97; H, 4.78; N, 16.08; Found: C, 45.99; H, 4.30; N, 16.03.

EXAMPLE 21

Preparation of N-Hydroxy-N-[3-(((3-phenoxybenzoyl)amino)-propyl]urea

The title compound was obtained following the procedures described in Example 2, but employing 3-aminopropanol in lieu of 2-aminoethanol. m.p. 135.5°–138° C.; $^1$H NMR (300 MHz, DMSO-$d_6$); 9.25 (1H, s), 8.50 (1H, t, J=5 Hz), 7.63 (1H, dt, J=8,1,1), 7.38–7.52 (4H, m), 7.18 (2H, m), 7.03 (2H, dq, J=7,1,1,1, Hz), 6.30 (2H, s), 3.37 (2H, t, J=7.5), 3.25 (2H, q, J=7.5), 1.73 (2H, pentet, J=7.5); MS (M+H)$^+$=330, (M+NH$_4$)$^+$=347. Analysis calc'd for $C_{17}H_{19}N_3O_4(0.25\ H_2O)$: C, 61.16; H, 5.89; N, 12.59; Found: C, 61.07; H, 5.79; N, 12.74.

EXAMPLE 22

Preparation of N-Hydroxy-N-[4-((3-phenoxybenzoyl)amino)butyl]urea

The title compound was obtained following the procedures described in Example 2, but employing 4-aminobutanol in lieu of 2-aminoethanol. m.p. 131°– 133° C.; $^1$H NMR (300 MHz, DMSO-$d_6$); 9.20 (1H, s), 8.50 (1H, t, J=5 Hz), 7.63 (1H, d, J=8), 7.38–7.52 (4H, m), 7.18 (2H, br t, J=7.5 Hz), 7.03 (2H, br d, J=7.5 Hz), 6.32 (2H, s), 3.37 (2H, br m), 3.23 (2H, br q, J=6 Hz), 1.50 (4H,br m); MS (M+H)$^+$=344, (M+NH$_4$)$^+$=361 (weak). Analysis calc'd for $C_{18}H_{21}N_3O_4(0.25\ H_2O)$: C, 62.96; H, 6.16; N, 12.24; Found: C, 62.52; H, 6.16; N, 12.08.

EXAMPLE 23

Preparation of N-Hydroxy-N'-methyl-N-[3-((3-phenoxybenzoyl)-amino)propyl]urea The title compound was obtained following the procedures described in Example 26, but employing N-methylisocyanate in lieu of N-trimethylsilyl isocyanate. m.p. 175°–177° C.; $^1$H NMR (300 MHz, DMSO-$d_6$); 9.18 (1H, s), 8.48 (1H, t, J=5 Hz), 7.63 (1H, d, J=8), 7.38–7.52 (4H, m), 7.18 (2H, m), 7.05 (2H, dq, J=7,1,1,1, Hz), 6.83 (1H, q, J=6 Hz), 3.34 (2H, t, J=7.5), 3.25 (2H, q, J=7.5), 2.58 (3H, d, J=6 Hz), 1.73 (2H, pentet, J=7.5); MS (M+H)$^+$=344. Analysis calc'd for $C_{18}H_{21}N_3O_4$: C, 62.96; H, 6.16; N, 12.24; Found: C, 62.52; H, 6.14; N, 12.08.

EXAMPLE 24

Preparation of N-Hydroxy-N'-methyl-N-[2-((3-phenoxybenzoyl)-amino)ethyl]urea The title compound was obtained following the procedures described in Example 2, but employing N-methylisocyanate in lieu of N-trimethylsilyl isocyanate. m.p. 161°–162.5° C.; $^1$H NMR (300 MHz, DMSO-$d_6$); 9.22 (1H, s), 8.48 (1H, t, J=5 Hz), 7.63 (1H, d, J=8), 7.38–7.52 (4H, m), 7.18 (2H, m), 7.05 (2H, dq, J=7,1,1,1, Hz), 6.87 (1H, q, J=6 Hz), 3.37–3.52 (4H, m), 2.58 (3H, d, J=6 Hz); MS (M+H)$^+$=330, (M+NH$_4$)$^+$=347. Analysis calc'd for $C_{17}H_{19}N_3O_4$: C, 62.00; H, 5.81; N, 12.76; Found: C, 62.10; H, 5.86; N, 12.73.

EXAMPLE 25

Preparation of N-Hydroxy-N-[2-((3-(3-trifluoromethylphenoxy)-benzoyl)amino)ethyl]urea The title compound was obtained following the procedures described in Example 2, but employing 3-(3-trifluoromethylphenoxy)benzoate in lieu of 3-phenoxybenzoate. m.p. 126°–128° C.; $^1$H NMR (300 MHz, DMSO-$d_6$); 9.28 (1H, s), 8.52 (1H, t, J=5 Hz), 7.56–7.67 (2H, m), 7.52–7.47 (3H, m), 7.19–7.33 (3H, m), 6.28 (2H, s), 3.47 (2H, m), 3.37 (2H, m), 1.73 (2H, pentet, J=7.5); MS (M+H)$^+$=384, (M+NH$_4$)$^+$=401. Analysis calc'd for $C_{17}H_{16}F_3N_3O_4$: C, 53.27; H, 4.21; N, 10.96; Found: C, 53.10; H, 4.28; N, 10.87.

EXAMPLE 26

Preparation of N-Hydroxy-N-[2-((3-(4-chlorophenoxy)benzoyl)-amino)ethyl]urea The title compound was obtained following the procedures described in Example 2, but employing 3-(4-chlorophenoxy)benzoate in lieu of 3-phenoxybenzoate. m.p. 146°–147° C.; $^1$H NMR (300 MHz, DMSO-$d_6$); 9.31 (1H, s), 8.53 (1H, t, J=5 Hz), 7.63 (1H, br d, J=7.5 Hz), 7.52–7.43 (4H, m), 7.21 (1H, dd, J=7.5, 3 Hz), 7.06 (2H, d, J=9.5 Hz), 6.33 (2H, s), 3.48 (2H, m), 3.42 (2H, m); MS (M+H)$^+$=350, (M+NH$_4$)$^+$=367. Analysis calc'd for $C_{16}H_{16}ClN_3O_4$: C, 54.94; H, 4.61; N, 12.01; Found: C, 54.90; H, 4.58; N, 11.55.

EXAMPLE 27

Preparation of
N-Hydroxy-N'-methyl-N-[2-((3-(4-chlorophenoxy)-
benzoyl)amino)ethyl]urea The title compound was obtained following the procedures described in Example 26, but employing N-methylisocyanate in lieu of N-trimethylsilyl isocyanate. m.p. 157°–158° C.; $^1$H NMR (300 MHz, DMSO-d$_6$); 9.24 (1H, s), 8.53 (1H, t, J=5 Hz), 7.63 (1H, br d, J=7.5 Hz), 7.52–7.43 (4H, m), 7.21 (1H, dd, J=7.5, 3 Hz), 7.06 (2H, d, J=9.5 Hz), 6.87 (1H, q, J=5 Hz), 3.52–3.38 (4H, m), 2.56 (1H, d, J=5 Hz); MS (M+H)$^+$=364, (M+NH$_4$)$^+$=381. Analysis calc'd for C$_{17}$H$_{18}$ClN$_3$O$_4$ (0.25 H$_2$O): C, 55.44; H, 5.06; N, 11.41; Found: C, 55.70; H, 5.06; N, 11.34.

EXAMPLE 28

Preparation of
N-Hydroxy-N-[2-((3-(4-methoxyphenoxy)benzoyl)-
amino)ethyl]urea

The title compound was obtained following the procedures described in Example 2, but employing 3-(4-methoxyphenoxy)benzoate in lieu of 3-phenoxybenzoate. m.p. 160°–162° C.; $^1$H NMR (300 MHz, DMSO-d$_6$); 9.31 (1H, s), 8.50 (1H, t, J=5 Hz), 7.53 (1H, br d, J=7.5 Hz), 7.42 (1H, t, J=7.5 Hz), 7.35 (1H, br s), 7.10–6.96 (5H, m), 6.33 (2H, s), 3.77 (3H, s), 3.48 (2H, m), 3.40 (2H, m); MS (M+H)$^+$= 346. Analysis calc'd for C$_{17}$H$_{19}$N$_3$O$_5$: C, 59.12; H, 5.55; N, 12.17; Found: C, 59.06; H, 5.52; N, 11.98.

EXAMPLE 29

Preparation of
N-Hydroxy-N-[2-((3-(3,4-dichlorophenoxy)benzoyl)-
amino)ethyl]urea The title compound was obtained following the procedures described in Example 2, but employing 3-(3,4-dichlorophenoxy)benzoate in lieu of 3-phenoxybenzoate. m.p. 153°–156° C.; $^1$H NMR (300 MHz, DMSO-d$_6$); 9.33 (1H, s), 8.54 (1H, t, J=5 Hz), 7.68 (1H, br d, J=7 Hz), 7.65 (1H, d, J=9 Hz), 7.53 (1H, d, J=9 Hz), 7.37 (1H, d, J=3), 7.27 (1H, dd, J=9,3 Hz), 7.03 (1H, dd, J=9,3 Hz), 6.33 (2H, s), (3.77 (3H, s), 3.48 (2H, m), 3.42 (2H, m); MS (M+H)$^+$=384. Analysis calc'd for C$_{16}$H$_{15}$Cl$_2$N$_3$O$_4$: C, 50.02; H, 3.93; N, 10.94; Found: C, 50.15; H, 4.02; N, 10.34.

EXAMPLE 30

Preparation of
N-Hydroxy-N-[2-((3-(3,5-dichlorophenoxy)benzoyl)-
amino)ethyl]urea The title compound was obtained following the procedures described in Example 2, but employing 3-(3,5-dichlorophenoxy)benzoate in lieu of 3-phenoxybenzoate. m.p. 164°–166° C.; $^1$H NMR (300 MHz, DMSO-d$_6$); 9.33 (1H, s), 8.56 (1H, t, J=5 Hz), 7.70 (1H, br d, J=7.5 Hz), 7.55 (1H,t, J=7.5 Hz), 7.53 (1H, br s), 7.40 (1H, t, J=1.5), 7.29 (1H, dd, J=7.5,3 Hz), 7.10 (2H, d, J=1.5 Hz), 6.33 (2H, s), (3.77 (3H, s), 3.48 (2H, m), 3.42 (2H, m); MS (M-CHNO)$^+$ =341. Analysis calc'd for C$_{16}$H$_{15}$Cl$_2$N$_3$O$_4$: C, 50.02; H, 3.93; N, 10.94; Found: C, 49.83; H, 3.83; N, 10.82.

EXAMPLE 31

Preparation of
N-Hydroxy-N-[2-((3-(4-tert-butylphenoxy)benzoyl)-
amino)ethyl]urea The title compound was obtained following the procedures described in Example 2, but employing 3-(4-t-butylphenoxy)benzoate in lieu of 3-phenoxybenzoate. m.p. 100°–102° C.; $^1$H NMR (300 MHz, DMSO-d$_6$); 9.31 (1H, s), 8.53 (1H, t, J=5 Hz), 7.59 (1H, br d, J=7.5 Hz), 7.39–7.50 (4H, m), 7.15 (1H, dd, J=7.5, 3 Hz), 6.97 (2H, d, J=9.5 Hz), 6.33 (2H, s), 3.48 (2H, m), 3.42 (2H, m), 1.29 (9H, s); MS (M+H)$^+$=372. Analysis calc'd for C16H$_{16}$ClN$_3$O$_4$: C, 54.94; H, 4.61; N, 12.01; Found: C, 54.90; H, 4.58; N, 11.55.

EXAMPLE 32

Preparation of
(R)-N-Hydroxy-N-[2-((3-phenoxybenzoyl)amino)-
propyl]urea

The title compound was obtained following the procedures described in Example 2, but employing (R)-(-)-2-amino-1-propanol in lieu of ethanolamine. m.p. 153.5°–154° C.; $^1$H NMR (300 MHz, DMSO-d$_6$); 9.31 (1H, s), 8.34 (1H, d, J=8 Hz), 7.61 (1H, br d, J=7.5 Hz), 7.38–7.50 (4H, m), 7.17 (2H, br t, J=6.5), 7.03 (2H, br d, J=7.5 Hz), 6.30 (2H, s), 4.24 (1H, septet, J=6.5Hz), 3.48 (1H, ABX, J=13,8 Hz), 3.42 (1H, ABX, J=13,7 Hz), 1.13 (3H, d, J=6.5Hz); MS (M+H)$^+$=330, (M+NH$_4$)$^+$=347. Analysis calc'd for C$_{17}$H$_{19}$N$_3$O$_H$ (0.25 H$_2$O): C, 61.16; H, 5.89; N, 12.59; Found: C, 61.42; H, 5.81; N, 12.56.

EXAMPLE 33

Preparation of
(d,l)-N-Hydroxy-N-[3-((3-phenoxybenzoyl)amino)-
prop-2-yl]urea

The title compound was obtained following the procedures described in Example 2, but employing 1-amino-2-propanol in lieu of ethanolamine. m.p. 189°– 190° C.; $^1$H NMR (300 MHz, DMSO-d$_6$); 8.80 (1H, s), 8.48 (1H, t, J=5 Hz), 7.59 (1H, br d, J=8 Hz), 7.48 (1H, t, J=8 Hz), 7.38–7.45 (3H, m), 7.14–7.22 (2H, m), 7.04 (2H, br d, J=7.5 Hz), 6.30 (2H, s), 4.27 (1H, sextet, J=6.5Hz), 3.18–3.38 (2H,m), 0.98 (3H, d, J=6.5Hz); MS (M+H)$^+$=329, (M+NH$_4$)$^+$= 347. Analysis calc'd for C$_{17}$H$_{19}$N$_3$O$_4$: C, 62.00; H, 5.81; N, 12.76; Found: C, 61.78; H, 5.85; N, 12.73.

EXAMPLE 34

Preparation of
N-Hydroxy-N-[2-((4-phenylbenzoyl)amino)ethyl]urea

The title compound was obtained following the procedures described in Example 2, but employing 4-phenylbenzoate in lieu of 3-phenoxybenzoate. m.p. 160°–162° C.; $^1$H NMR (300 MHz, DMSO-d$_6$); 9.36 (1H, s), 8.53 (1H, t, J=5 Hz), 7.92 (2H, d, J=9 Hz), 7.72–7.8 (4H, m), 7.49 (2H, br t, J=7.5 Hz), 7.40 (1H, t, J=7.5 Hz), 6.35 (2H, s), 3.42–3.57 (4H, m); MS (M+H)$^+$=300, (M+NH$_4$)$^+$=317. Analysis calc'd for C$_{16}$H$_{17}$N$_3$O$_3$(0.10 H$_2$O): C, 63.82; H, 5.76; N, 13.95; Found: C, 64.26; H, 5.76; N, 13.52.

EXAMPLE 35

Preparation of N-Hydroxy-N-[2-((3-phenylmethyloxybenzoyl)-amino)ethyl]urea

The title compound was obtained following the procedures described in Example 2, but employing 3-benzyloxybenzoate in lieu of 3-phenoxybenzoate. m.p. 183°–185° C.; $^1$H NMR (300 MHz, DMSO-$d_6$); 9.33 (1H, s), 8.46 (1H, t, J=5 Hz), 7.30–7.50 (8H, m), 7.17 (1H, br d, J=8 Hz), 6.33 (2H, s), 5.14 (2H, s), 3.38–3.54 (4H, m); MS (M+H)$^+$=330, (M+NH$_4$)$^+$=347. Analysis calc'd for $C_{17}H_{19}N_3O_4$: C, 62.00; H, 5.81; N, 12.76; Found: C, 62.40; H, 6.37; N, 11.49.

EXAMPLE 36

Preparation of N-Hydroxy-N-[2-((5-phenoxyfuran-2-oyl)amino)-ethyl]urea

Step 1: Preparation of 5-phenoxy-2-furoic acid

A flask was charged with 5-nitro-2-furoic acid (15.02 g, 95.62 mmol), absolute ethanol (100 mL), and concentrated sulfuric acid (1 mL) and refluxed overnight. After cooling the reaction mixture, the volatiles were removed under vacuum, the resulting slurry taken up into ethyl acetate, and washed sequentially (1×, NaHCO$_3$; 1×, brine), dried (MgSO$_4$), filtered and concentrated under vacuum to provide the corresponding ester as a light yellow solid (15.31 g, 87%) which was used without further purification.

A flask was charged with NaH (2.9 g, 96.7 mmol, 80% suspension in oil), and dimethylsulfoxide (DMSO)(200 mL), and flushed with nitrogen. To this solution was added neat phenol (9.1 g, 96.7 mmol) in a portionwise fashion; the reaction was stirred under nitrogen until gas evolution ceased. A solution of 5-nitro- 2-furoic acid (14.92 g, 80.6 mmol) in DMSO (120 mL) was then added to the reaction to give a dark purple solution which was judged to be complete by thin layer chromatography after 0.5 h. The reaction was poured into saturated aqueous NaHCO$_3$ and extracted with ethyl acetate (3×). The combined organic extracts were washed (3×, H$_2$O), dried (MgSO$_4$), filtered and concentrated under vacuum to provide the corresponding phenoxy ester as an orange-brown liquid (21.11 g, 113%) contaminated with phenol which was used without further purification.

The unpurified phenoxy ester (5 g, 18.3 mmol) was dissolved in dioxane and water added until the reaction permanently clouded. Under a constant nitrogen flow, LiOH(H$_2$O) (1.23 g, 29.26 mmol) was added. The resulting mixture was stirred at ambient temperature for 2 h, and poured into water. The resulting solution was extracted with ether and the organic layer drawn off. The aqueous layer was acidified to pH~1 and extracted with ethyl acetate (2×). The combined organic extracts were washed (3×, H$_2$O), dried (MgSO$_4$), filtered and concentrated under vacuum to provide the corresponding phenoxy acid as a white solid. Recrystallization from ether/hexanes provided the pure title compound (3.05 g, 82%). m.p. 131°–132° C.; $^1$H NMR (300 MHz, $D_6$-DMSO); 10.20 (1H, br s), 7.39 (2H, t, J=8 Hz), 7.31 (1H, d, J=3 Hz), 7.23 (1H, t, J=8 Hz), 7.14 (2H, t, J=8 Hz), 5.53 (1H, d, J=3 Hz); MS (M+H)$^+$=205, (M+NH$_4$)$^+$=222.

Step 2: Preparation of N-Hydroxy-N-[2-((5-phenoxyfuran-2-oyl)amino)ethyl]urea

The title compound was obtained following the procedures described in Example 2, but employing 5-phenoxy-2-furanoic acid (prepared in step 1, above) in lieu of 3-phenoxybenzoate. m.p. 160°–163° C.; $^1$H NMR (300 MHz, DMSO-$D_6$); 9.28 (1H, s), 8.22 (1H, t, J=5 Hz), 7.45 (2H, t, J=8 Hz), 7.23 (1H, t, J=8 Hz), 7.16 (1H, d, J=8 Hz), 7.10 (2H, d, J=3 Hz), 6.33 (2H, s), 5.86 (1H, d, J=3 Hz) 3.30–3.49 (4H, m); MS (M+H)$^+$=306, (M+NH$_4$)$^+$=323. Analysis calc'd for $C_{14}H_{15}N_3O_5$(0.10 H$_2$O): C, 54.76; H, 4.99; N, 13.68; Found: C, 54.57; H, 4.94; N, 13.33.

EXAMPLE 37

Preparation of N-Hydroxy-N-[2-(N-methyl-((3-(4-chlorophenoxy)-phenyl)methyl)amino)ethyl]urea Step 1: Preparation of N-Methyl-N-(3-(4-chlorophenoxy)phenylmethyl)-2-aminoethanol A flask was charged with N-methyl ethanolamine (4.88 mL, 60.68 mmol), hydrochloric acid (4.5 mL of 4.5M HCl in dioxane, 20.23 mmol), and absolute ethanol (20 mL). To the resulting solution was added 3-(4-chlorophenoxy)phenylcarboxaldehyde (4.0 mL, 20.23 mmol) in ethanol (20 mL) and in small portions NaCNBH$_3$ (1.27 g, 20.23 mmol). The reaction was stirred at ambient temperature for 1.5 h and the volatiles removed under vacuum. The residue was carefully dissolved in excess 10% aqueous HCl, the pH adjusted to greater than pH 10 with freshly prepared 15% aqueous NaOH, and the resulting suspension was extracted with ethyl acetate (2×). The combined organic extracts were washed (2×, brine), dried (MgSO$_4$), filtered and concentrated under vacuum to provide the unpurified aminoalcohol. Chromatographic purification (silica gel, 500 mL 20% ethyl acetate/ hexanes, 500 mL ethyl acetate, 1 L 10% methanol/ ethyl acetate) provided the corresponding aminoalcohol as a viscous oil (2.99 g, 51%). m.p. 131°–132° C.; $^1$H NMR (300 MHz, $D_6$-DMSO) 7.25–7.32 (3H, m), 6.85–6.97 (4H, m), 3.62 (2H, t, J=6 Hz), 3.53 (2H, s), 2.58 (2H, t, J=6 Hz), 2.52 (1H, br s), 2.23 (3H, s); MS (M+H)$^+$=292.

Step 2: Preparation of N-Hydroxy-N-[2-(N-methyl-((3-(4-chlorophenoxy)phenyl)methyl)amino)ethyl]urea The title compound was obtained following the procedures described in Example 2, but employing the amino ethanol (prepared as described in step 1, above) in lieu of the amide alcohol. m.p. 111°–113° C.; $^1$H NMR (300 MHz, DMSO-$D_6$); 9.23 (1H, s), 7.43 (2H, d, J=9 Hz), 7.33 (1H, t, J=8 Hz), 7.10 (1H, d, J=8 Hz), 7.02 (2H, d, J=9 Hz), 6.98 (1H, br s), 6.90 (1H, dd, J=8,3 Hz), 6.23 (2H, s), 3.49 (2H,s), 2.50 (2H, t, J=7.5 Hz), 2.13 (3H, s); MS (M+H)$^+$= 350. Analysis calc'd for $C_{17}H_{20}N_3O_3Cl$: C, 58.37; H, 5.76; N, 12.01; Found: C, 58.12; H, 5.75; N, 11.88.

EXAMPLE 38

Preparation of N-Hydroxy-N-[2-(N-methyl-((3-(4-methoxyphenoxy)-phenyl)ethyl)amino)ethyl]urea The title compound was obtained following the procedures described in Example 2, but employing N-methyl-N-(3-(4-methoxyphenoxy)phenylmethyl)-2-aminoethanol (prepared as in Example 37, step 1 from 3-(4-methoxyphenoxy)phenylcarboxaldehyde) in lieu of 3-(4-chlorophenoxy)phenylcarboxaldehyde. m.p. 87°–88.5° C.; $^1$H NMR (300

MHz, DMSO-d$_6$); 9.23 (1H, s), 7.27 (1H, t, J=8 Hz), 6.92–7.02 (5H, m), 6.88 (1H, br s), 6.78 (1H, dd, J=8,3 Hz), 6.23 (2H, s), 3.76 (3H, s), 3.41–3.48 (4H, m), 2.47–2.52 (2H, m), 2.13 (3H, s); MS (M+H)$^+$=346. Analysis calc'd for C$_{18}$H$_{23}$N$_3$O$_4$: C, 62.59; H, 6.71; N, 12.17; Found: C, 62.39; H, 6.76; N, 12.13.

EXAMPLE 39

Preparation of N-Hydroxy-N-[2-(N-methyl((3-(3,4-dichlorophenoxy)-phenyl)methyl)amino)ethyl] urea The title compound was obtained following the procedures described in Example 2, but employing N-methyl-N-(3-(3,4-methoxyphenoxy)phenylmethyl)-2-aminoethanol (prepared as in Example 37, step 1 from 3-(3,4-dichlorophenoxy)phenylcarboxaldehyde) in lieu of 3-(4-chlorophenoxy)phenylcarboxaldehyde. m.p. 107°–109° C.; $^1$H NMR (300 MHz, DMSO-d$_6$); 9.23 (1H, s), 7.63 (1H,d, J=9 Hz), 7.37 (1H, t, J=8 Hz), 7.29 (1H, d, J=3 Hz), 7.16 (1H. br d, J=8 Hz), 7.03 (1H, br s), 6.94–7.00 (2H, m), 6.23 (2H, s), 3.50 (2H, s), 3.45 (2H, t, J=6.5 Hz), 2.50 (2H, t, J=6.5 Hz), 2.13 (3H, s); MS (M+H)$^+$=384/386. Analysis calc'd for C$_{17}$H$_{19}$N$_3$O$_3$Cl$_2$: C, 53.14; H, 4.98; N, 10.94; Found: C, 52.93; H, 4.94; N, 10.79.

EXAMPLE 40

Preparation of N-Hydroxy-N-[2-(N-methyl-((3-(3,5-dichlorophenoxy)phenyl)methyl)amino)ethyl]urea The title compound was obtained following the procedures described in Example 2, but employing N-methyl-N-(3-(3,5-methoxyphenoxy)phenylmethyl)-2-aminoethanol (prepared as in step 1, example 37 from 3-(3,5-dichlorophenoxy)phenyl)carboxaldehyde) in lieu of the amidealcohol: m.p. 111°–113° C.; $^1$H NMR (300 MHz, DMSO-d$_6$); 9.23 (1H, s), 7.33–7.42 (2H, m), 7.29 (1H, d, J=7.5 Hz), 6.96–7.08 (3H, m), 6.23 (2H, s), 3.50 (2H, s), 3.47 (2H, t, J=6.5 Hz), 2.52 (2H, t, J=6.5 Hz), 2.13 (3H, s); MS (M+H)$^+$=384/386. Analysis calc'd for C$_{17}$H$_{19}$N$_3$O$_3$Cl$_2$: C, 53.14; H, 4.98; N, 10.94; Found: C, 53.02; H, 4.88; N, 10.75.

EXAMPLE 41

Preparation of N-Hydroxy-N-[2-(((((4-methoxy-3-phenylmethoxy)-phenyl)methyl)N-methyl)amino)ethyl]urea The title compound was obtained following the procedures described in Example 2, but employing N-methyl-N-(3-(benzyloxy)-4-methoxyphenylmethyl)- 2-aminoethanol (prepared as in step 1, example 37 from 3-(benzyloxy)-4-methoxyphenylcarboxaldehyde) in lieu of 3-(4-chlorophenoxy)phenylcarboxaldehyde m.p. 108°–111° C.; $^1$H NMR (300 MHz, DMSO-d$_6$); 9.27 (1H, s), 7.30–7.48 (5H, m), 7.01 (1H, br s), 6.90 (1H, d, J=8, Hz), 6.81 (1H, br d, J=8, Hz), 6.27 (2H, s), 5.05 (2H, s), 3.76 (3H, s), 3.49 (2H, t, J=7.5 Hz), 3.42 (2H, br s), 2.47–2.52 (2H, m), 2.12 (3H, s); MS (M+H)$^+$=360. Analysis calc'd for C$_{19}$H$_{25}$N$_3$O$_4$: C, 63.49; H, 7.01; N, 11.69; Found: C, 63.05; H, 7.05; N, 11.56.

EXAMPLE 42

Preparation of (S)-N-Hydroxy-N-[2-((tert-butoxycarbonyl)amino)-propyl]urea (S)-N-Boc-alaninol (13.5 g, 77 mmol) and triethylamine (43 mL, 308 mmol) were dissolved in dichloromethane (45 mL) and cooled to 0° C. A solution of sulfur trioxide pyridine (36.8 g, 231.1 mmol) in DMSO (45 mL, gentle warming is needed to achieve complete dissolution) was added rapidly to the reaction solution. The cooling bath was removed 15 minutes after addition was completed and the reaction monitored for completion by tlc analysis of quenched aliquots. The reaction was judged to be complete after 30 minutes, poured into brine, and extracted with ethyl acetate (2×). The combined organic layers were washed with 10% aqueous HCl (2×), brine (2×), dried (MgSO$_4$), filtered, and concentrated in vacuo to give an oil which solidified upon vacuum drying to give the corresponding aldehyde (12.95 g, 96%). [The aldehydes are not stable and are best immediately convened to the oxime.]

The aldehyde is dissolved in ethanol (300 mL) and hydroxylamine hydrochloride (10.7 g, 110.5 mmol) and pyridine (6.2 mL, 77 mmol) were added. The reaction was stirred at ambient temperature until judged complete (typically 1–2 hours) by thin layer chromatography. The volatiles were removed in vacuo and the resulting slurry was partitioned between ethyl acetate and 10% aqueous HCl. The aqueous layer was extracted (2×, ethyl acetate) and the combined organic layers washed (2×, saturated aqueous sodium bicarbonate; 2×, brine), dried (MgSO$_4$), filtered, and concentrated in vacuo to give the oxime as an oily solid (12.96 g, 89 % which was carried on without further purification.

The oxime (6.0 g, 31.8 mmol) was dissolved in glacial acetic acid (110 mL) and tetrahydrofuran (25 mL). The sodium cyanoborohydride (2.6 g, 41.4 mmol) was added in a single portion. When gas evolution ceases and all of the sodium cyanoborohydride was dissolved the reaction was complete. The reaction was neutralized with 6N NaOH to pH~7 and then saturated aqueous sodium bicarbonate was added to adjust the pH to 9. The resulting two phased solution was extracted with ethyl acetate (3×). The combined organic layers were washed with brine (2×), dried (MgSO$_4$), filtered, and concentrated in vacuo to give the N-hydroxylamine as an oil (6.2 g, 100%). The unpurified N-hydroxylamine was best converted as soon as possible to the N-hydroxy urea to avoid decomposition.

The N-hydroxylamine (6.2 gm, 31.8 mmol) was dissolved in freshly dried tetrahydrofuran (100 mL) and treated with TMS-isocyanate (5 mL, 38.2 mmol) at ambient temperature. The reaction was typically complete within 1 hour, treated with water (1.15 mL, 64 mmol) and methanol (100 mL), and concentrated in vacuo to provide the unpurified title compound as a solid (7.11 g). Recrystallization from ethyl acetate/methanol provided 2.53 g (34%) of pure product. The mother liquors were chromatographed (200 g silica gel; column packed in dichloromethane and eluted with 5% methanol/dichloromethane) to provide 1.09 g (15%) of additional product. m.p. 156°–160° C.; $^1$H NMR (300 MHz, DMSO-D$_6$); 9.23 (1H, s), 6.64 (1H, br d J=8.0 Hz), 6.27 (2H, s), 3.72 (1H, septet, J=6.5 Hz), 3.35 (1H, ABX, J=13.0,8.0 Hz), 3.22 (1H, ABX, J=13.0,5.5 Hz), 1.38 (9H, s); MS (M+H)$^+$=234; (M+NH$_4$)$^+$=251. Analysis calc'd for C$_9$H$_{19}$N$_3$O$_4$ (0.25 H$_2$O): C, 45.46; H, 8.27; N, 17.67; Found: C, 45.59; H, 7.83; N, 17.24.

EXAMPLE 43

Preparation of (R)-N-Hydroxy-N-[2-((tert-butoxycarbonyl)amino)-propyl]urea

The title compound was prepared according to the procedures described for the preparation of the (S)-isomer in example 42 by employing (R)-N-Boc-alaninol in lieu of (S)-N-Boc-alaninol. m.p. 156°–160° C.; $^1$H NMR (300 MHz, DMSO-D$_6$); 9.23 (1H, s), 6.64 (1H, br d J=8.0 Hz), 6.27 (2H, s), 3.72 (1H, septet, J= 6.5 Hz), 3.35 (1H, ABX, J=13.0,8.0 Hz), 3.22 (1H, ABX, J=13.0,5.5 Hz), 1.38 (9H, s); MS (M+H)$^+$=234; (M+NH$_4$)$^+$=251. Analysis calc'd for C$_9$H$_{19}$N$_3$O$_4$(0.25 H$_2$O): C, 45.46; H, 8.27; N, 17.67; Found: C, 45.59; H, 7.83; N, 17.24.

EXAMPLE 44

Preparation of N-Hydroxy-N-[2-((tert-butoxycarbonyl)amino)-ethyl]urea

The title compound was prepared according to the procedures described for the preparation of the (S)-isomer in example 42 by employing N-Boc-ethanolamine in lieu of (S)-N-Boc-alaninol. m.p. 144°–145.5° C.; $^1$H NMR (300 MHz, DMSO-D$_6$); 9.18 (1H, s), 6.62 (1H, br t, J=5.5 Hz), 6.27 (2H, s), ca. 3.30 (2H, br t, J= 6.5 Hz), 3.03 (2H, br q, J=6.5 Hz), 1.34 (9H, s); MS (M+H)$^+$=220. Analysis calc'd for C$_8$H$_{17}$N$_3$O$_4$: C, 43.83; H, 7.82; N, 19.17; Found: C, 44.09; H, 7.84; N, 19.38.

EXAMPLE 45

Preparation of N-Hydroxy-N-[(((3-(4-chlorophenoxy)phenyl)-prop-2-enyl)amino)carbonyl)methyl]urea The title compound was obtained following the procedures described in Example 1, but employing trans-1-amino-3-((4-chlorophenoxy)phenyl)-prop-2-ene (prepared according to the method of Dellaria (Dellaria, J. F.; Sallin, K. J. *Tetrahedron Lett.* 1990, 31, 2661)) in lieu of 4-phenoxyaniline. m.p. 150°–151° C.; $^1$H NMR (300 MHz, DMSO-d$_6$); 9.40 (1H, s), 7.74 (1H, d, J=7.5 Hz), 7.30– 7.42 (3H, m), 7.10–7.22 (2H, m), 6.97–7.07 (3H, m), 6.88 (1H, dd, J=8, 2 Hz), 6.47 (1H, d, J=15.5 Hz), 6.43 (2H, s), 6.27 (1H, dd, J=15.5, 6 Hz),4.53 (1H, sextet, J=6.5 Hz) 3.97(2H, s), 1.24 (3H, d, J=6.5 Hz); MS (M+H)$^+$=356, (M+NH$_4$)$^+$=373. Analysis calc'd for C$_{19}$H$_{21}$N$_3$O$_4$: C, 64.21; H, 5.96; N, 11.82; Found: C, 64.29; H, 6.04; N, 11.80.

EXAMPLE 46

Preparation of N-Hydroxy-N-[2-((3-(1-methylethoxy)benzoyl)-amino)ethyl]urea

The title compound was obtained following the procedures described in Example 2, but employing 3-(1-methylethoxy)benzoate in lieu of 3-phenoxybenzoate. The 3-(1-methylethoxy)benzoate was prepared as described in Example 19 using isopropyl iodide in lieu of n-butyl iodide. m.p. 174°–175° C.: $^1$H NMR (300 MHz, DMSO-d$_6$); 9.33 (1H, s), 8.43 (1H, br t, J=6.0 Hz), 7.30– 7.39 (3H, m), 7.15 (1H, dt, J=7.0,3.0,3.0), 6.33 (2H, s), 4.66 (1H, septet, J=6.0 Hz), 3.48 (2H, m), 3.43 (2H, m), 1.28 (3H, d, J=5.5 Hz); MS (M+H)$^+$= 282, (M+NH$_4$)$^+$=299; Analysis calc'd for C$_{13}$H$_{19}$N$_3$O$_4$: C, 55,50; H, 6.81; N, 14.94 Found: C, 55.39; H, 6.84 N, 14.86.

EXAMPLE 47

Preparation of N-Hydroxy-N-[2-((3-(2-methyl-prop-2-enyloxy)-benzoyl)amino)ethyl]urea The title compound was obtained following the procedures described in Example 2, but employing 3-(2-methylprop-2-enyloxy)benzoate in lieu of 3-phenoxybenzoate. The 3-(2-methylprop-2-enyloxy)benzoate was prepared as described in Example 19 using isobutenyl bromide in lieu of n-butyl iodide. m.p. 148°–149° C.: $^1$H NMR (300 MHz, DMSO-d$_6$); 9.29 (1H, s), 8.46 (1H, br t, J=5.5 Hz), 7.34–7.43 (3H, m), 7.12 (1H, dt, J=8.5,2.0,2.0), 6.33 (2H, s), 5.08 (1H, br s), 4.97 (1H, br s),4.52 (2H, br s), 3.50 (2H, m), 3.44 (2H, m), 1.79 (3H, s); MS (M+H)$^+$=294, (M+NH$_4$)$^+$= 311; Analysis calc'd for C$_{14}$H$_{19}$N$_3$O$_4$: C, 57.33; H, 6.53; N, 14.33 Found: C, 57.34; H, 6.54 N, 14.27.

EXAMPLE 48

Preparation of N-Hydroxy-N-[2-((naphth-2-ylsulfonyl)amino)-ethyl]urea

The title compound was obtained following the procedures described in Example 2, but employing 2-napthylsulfonyl chloride in lieu of 3-phenoxybenzoyl chloride. m.p. 174° C. with decomposition: $^1$H NMR (300 MHz, DMSO-d$_6$); 9.33 (1H, s), 8.44 (1H, br s), 8.13–8.2 (2H, m), 8.06 (1H, br d, J=8.0 Hz), 7.83 (1H, dd, J=9,2 Hz), 7.63–7.78 (3H, m), 6.31 (2H, s), 3.37 (2H, m), 2.92 (2H, br t, J=7.5 Hz); MS (M+H)$^+$=310, (M+NH$_4$)$^+$=327; Analysis calc'd for C$_{13}$H$_{15}$N$_3$O$_4$S: C, 50.48; H, 4.89; N, 13.58 Found: C, 50.37; H, 4.90 N, 13.05.

EXAMPLE 49

Preparation of N-Hydroxy-N-[2-(((1-(4-chlorophenylmethyl)pyrrol-2-yl)carbonyl)-amino)ethyl]urea The title compound was obtained following the procedures described in Example 2, but employing N-(4-chlorophenylmethyl)-2-carboxypyrrole (prepared in standard fashion from 2-carboxypyrrole) in lieu of 3-phenoxybenzoyl chloride. m.p. 158°–160° C.; $^1$H NMR (300 MHz, DMSO-d$_6$); 9.31 (1H, s), 8.03 (1H, t, J=6.0 Hz), 7.36 (2H, d, J=9.0 Hz), 7.13 (2H, d, J=9.0 Hz), 7.06 (1H, t, J=2 Hz), 6.78 (1H, dd, J=4.0,2.0 Hz), 6.33 (2H, s), 6.08 (1H, dd, J=4.0,3.0 Hz), 5.56 (2H, s), 3.43 (2H, m), 3.33 (2H, m); MS (M+H)$^+$=337, (M+NH$_4$)$^+$= 354. Analysis calc'd for C$_{15}$H$_{17}$N$_4$O$_3$Cl: C, 53.50; H, 5.09; N, 16.64; Found: C, 53.44; H, 5.07; N, 16.61.

EXAMPLE 50

Preparation of N-Hydroxy-N-[2-(((3-(4-chlorophenoxy)-benzoyl)-N-methyl)amino)propyl]urea The title compound was obtained following the procedures described in Example 2, but employing d,l-N-methyl-alaninol in lieu of ethanol amine. $^1$H NMR (300 MHz, DMSO-d$_6$, an ~2:1 mixture of rotational isomers); 9.14 and 9.12 (1H, s), 7.47 (2H, d, J=9.0 Hz), 7.38–7.49 (1H, m), 6.95–7.2 (3H, m), 7.07 (1H, d, J= 9.0 Hz), 6.27 and 6.22 (2H, s), 4.83 and 3.96 (1H, br q, J=6.5 Hz), 3.52 and 3.70 (1H, br dd, J=13.5,8.5 Hz), 3.29 (2H, m), 1.05 and 1.13 (3H, br d, J=6.5 Hz); MS (M+H)$^+$=378, (M+NH$_4$)$^+$=395. Analysis calc'd for C18H$_{20}$ClN$_3$O$_t$ (0–5 H$_2$O): C, 55.89; H, 5.47; N, 10.86; Found: C, 556.23; H, 5.59; N, 10.36.

EXAMPLE 51

Preparation of N-Hydroxy-N-[2-((2-phenoxybenzoyl)amino)ethyl]urea

The title compound was obtained following the procedures described in Scheme III. To an ice-cooled solution of 2-phenoxybenzoate (5 g, 23.3 mmol) in dichloromethane (80 mL) was added oxalyl chloride (5.92 g, 46.7 mmol) in dichloromethane (15 mL) in a dropwise fashion over 10 minutes. After addition was complete the cooling bath was removed and the reaction was stirred until no further bubbling was observed (0.5–1.0 h). The volatiles were removed under vacuum and the resulting liquid was dissolved in dichloromethane (90 mL) and concentrated under vacuum (2 cycles) to insure complete removal of excess oxalyl chloride. To a solution of 2-phenoxybenzoyl chloride (245 rag, 1.05 mmol) in CH$_2$Cl$_2$ (5 mL) was added the hydroxyurea, (prepared as described in example 44) (231 mg, 1.05 mmol) followed by the dropwise addition of triethylamine (117 mg, 1.16 mmol) and a crystal of 4-dimethylaminopyridine. The reaction was then stirred for 0.5 h and concentrated. The resulting residue was taken up in trifluoroacetic acid (2 mL) and stirred for 0.50 h. This solution was then concentrated and the resulting residue was dissolved in CH$_2$Cl$_2$ (5 mL); to this solution was added triethylamine (0.293 mL, 2.10 mmol) and aqueous saturated NaHCO$_3$ (10 mL). After stirring for 0.5 h the aqueous phase was drawn off and extracted (2×, EtOAc). The combined organic extracts were washed sequentially (1×, saturated NaHCO$_3$; 1×, brine), dried (MgSO$_4$), filtered and concentrated in vacuo to provide the title compound as a powdery solid which was recrystallized (EtOAc/MeOH) to yield analytically pure title compound (235 mg, 68%). m.p. 182.5°–185° C.; $^1$H NMR (300 MHz, DMSO-d$_6$); 9.33 (1H, s), 8.24 (1H, br t, J=5 Hz), 7.72 (1H, dd, J=8,2 Hz), 7.36–7.49 (3H, m), 7.21 (1H, dt, J=2,8,8 Hz), 7.16 (1H, tt, J=1,1,8,8 Hz), 7.03 (1H, dq, J=8,1,1,1, Hz), 6.88 (1H, dd, J=8,1 Hz), 6.32 (2H, br s), 3.31–3.45 (4H, m); MS (M+H)$^+$=316. Analysis calc'd for C$_{16}$H$_{17}$N$_3$O$_4$: C, 60.95; H, 5.43; N, 13.33; Found: C, 61.28; H, 5.51; N, 13.34.

EXAMPLE 52

Preparation of N-Hydroxy-N-[2-((4-phenoxybenzoyl)amino)ethyl]urea

The title compound was obtained following the procedures described in Example 51, but employing 4-phenoxybenzoate in lieu of 2-phenoxybenzoate. m.p. 185°–186° C.; $^1$H NMR (300 MHz, DMSO-d$_6$); 9.33 (1H, s), 8.43 (1H, br t, J=5.5 Hz), 7.75 (2H, d, J=9 Hz), 7.43 (2H, dd, J=9,8 Hz), 7.21 (1H, t, J=8 Hz), 7.08 (1H, dq, J=8,1,1,1 Hz), 7.03 (2H, d, J=8 Hz), 6.32 (2H, br s), 3.39– 3.53 (4H, m); MS (M+H)$^+$=316. Analysis calc'd for C$_{16}$H$_{17}$N$_3$O$_4$: C, 60.95; H, 5.43; N, 13.33; Found: C, 60.49; H, 5.46; N, 13.17.

EXAMPLE 53

Preparation of N-Hydroxy-N-[2-(3-((4-bromophenoxy)benzoyl)-amino)ethyl]urea

The title compound was obtained following the procedures described in Example 51, but employing 3-(4-bromophenoxy)benzoate in lieu of 2-phenoxybenzoate. m.p. 186°–187° C.; $^1$H NMR (300 MHz, DMSO-d$_6$); 9.33 (1H, s), 8.46 (1H, br t, J=5.5 Hz), 7.87 (2H, d, J=9 Hz), 7.60 (2H, d, J=9 Hz), 7.07 (2H, d, J=9 Hz), 7.04 (2H, d, J=9 Hz), 6.32 (2H, br s), 3.39–3.53 (4H, m); MS (M+H)$^+$=394/396; (M+NH$_4$)$^+$=411/413. Analysis calc'd for C$_{16}$H$_{16}$N$_3$O$_4$Br(0.5 H$_2$O): C, 47.66; H, 4.25; N, 10.42; Found: C, 47.76; H, 4.02; N, 10.28.

EXAMPLE 54

Preparation of N-Hydroxy-N-[2-(3-((4-fluorophenoxy)benzoyl)-amino)ethyl]urea The title compound was obtained following the procedures described in Example 51, but employing 3-(4-fluorophenoxy)benzoate in lieu of 2-phenoxybenzoate. m.p. 179°–181° C.; $^1$H NMR (300 MHz, DMSO-d$_6$); 9.31 (1H, s), 8.52 (1 H, br t, J=5.5 Hz), 7.59 (1H, br d, J=8 Hz), 7.47 (1H, t, J=8 Hz), 7.42 (1H, dd, J=2,1 Hz), 7.26 (2H, t, J=9 Hz), 7.08–7.15 (1H, m), 7.10 (2H, dd, J=9,4.5 Hz), 6.32 (2H, br s), 3.39–3.53 (4H, m); MS (M+H)$^+$=334; (M+NH$_4$)$^+$=351. Analysis calc'd for C$_{16}$H$_{16}$N$_3$O$_4$F: C, 57.66; H, 4.84; N, 12.61; Found: C, 57.39; H, 4.79; N, 12.45.

EXAMPLE 55

Preparation of N-Hydroxy-N-[2-((3-(pyrid-2-yloxy)benzoyl)-amino)ethyl]urea

The title compound was obtained following the procedures described in Example 51, but employing 3-(2-pyridinyloxy)benzoate in lieu of 2-phenoxybenzoate. m.p. 159°–160° C.; $^1$H NMR (300 MHz, DMSO-d$_6$); 9.31 (1H, s), 8.53 (1H, br t, J=5.5 Hz), 8.17 (1H, dd, J=4.5,2 Hz), 7.88 (1H, ddd, J= 8.5,6.5,2 Hz), 7.68 (1H, br d, J=8.5 Hz), 7.56 (1H, t, J=2 Hz), 7.50 (1H, t, J= 8.5 Hz), 7.29 (1H, dd, J=8,2 Hz), 7.16 (1H, dd, J=7,4 Hz), 7.08 (1H, d, J=8 Hz), 6.32 (2H, br s), 3.39–3.53 (4H, m); MS (M+H)$^+$=317. Analysis calc'd for C$_{15}$H$_{16}$N$_4$O$_4$: C, 56.96; H, 5.10; N, 17.71; Found: C, 56.61; H, 5.06; N, 17.32.

EXAMPLE 56

Preparation of N-Hydroxy-N-[2-((3-phenoxyphenylacetyl)-amino)ethyl]urea

The title compound was obtained following the procedures described in Example 51, but employing (3-phenoxyphenyl)acetate in lieu of 2-phenoxybenzoate. m.p. 150°–152° C.; $^1$H NMR (300 MHz, DMSO-d$_6$); 9.27 (1H, s), 8.03 (1H, br t, J=5.5 Hz), 7.39 (2H, t, J=8 Hz), 7.30 (1H, t, J=8 Hz), 7.14 (1H, tt, J=7.5,0.5 Hz), 6.98–7.03 (3H,m), 6.92 (1H, t, J=2 Hz), 6.85 (1H, br d, J=8 Hz), 6.32 (2H, br s), 3.39 (2H, s), 3.30–3.38 (2H, m), 3.17–3.25 (2H, m), MS (M+H)$^+$=330; (M+NH$_4$)$^+$=347. Analysis calc'd for C$_{17}$H$_{19}$N$_3$O$_4$: C, 62.00; H, 5.80; N, 12.76; Found: C, 61.74; H, 5.80; N, 12.66.

EXAMPLE 57

Preparation of N-Hydroxy-N-[2-((4-n-hexyloxybenzoyl)-amino)ethyl]urea

The title compound was obtained following the procedures described in Example 51, but employing 4-hexyloxybenzoate in lieu of 2-phenoxybenzoate. m.p. 148°–151° C.;

¹H NMR (300 MHz, DMSO-d$_6$); 9.34 (1H, s), 8.33 (1H, br t, J=5.5 Hz), 7.78 (2H, d, J=8.5 Hz), 6.97 (2H, d, J=8.5 Hz), 6.32 (2H, br s), 4.00 (2H, t, J=6.5 Hz), 3.37–3.52 (4H, m), 1.72 (2H, pentet, J=6.5 Hz), 1.25– 1.48 (6H, m), 0.87 (3H, br t, J=6.5 Hz); MS (M+H)$^+$=324. Analysis calc'd for C$_{16}$H$_{25}$N$_3$O$_4$: C, 59.43; H, 7.79; N, 12.99; Found: C, 59.28; H, 7.74; N, 12.53.

EXAMPLE 58

Preparation of N-Hydroxy-N-[2-((5-(4-chlorophenoxy)furan-2-oyl)-amino)ethyl]urea The title compound was obtained following the procedures described in Example 2, but employing 5-(4-chlorophenoxy)-2-furanoic acid (prepared as in example 36, step 1 by using 4-chlorophenol in lieu of phenol) in lieu of 3-phenoxybenzoate. 64: m.p. 173°–175° C.; ¹H NMR (300 MHz, DMSO-d$_6$); 9.28 (1H, s), 8.23 (1H, t, J=5 Hz), 7.50 (2H, d, J=9 Hz), 7.21 (2H, d, J=9 Hz), 7.12 (1H, d, J=3 Hz), 7.10 (2H, d, J=3 Hz), 6.36 (2H, s), 5.92 (1H, d, J=3 Hz), 3.30–3.49 (4H, m); MS (M+H)$^+$=340/342. Analysis calc'd for C$_{14}$H$_{14}$N$_3$O$_5$Cl: C, 49.50; H, 4.15; N, 12.37; Found: C, 50.48; H, 4.29; N, 12.33.

EXAMPLE 59

Preparation of N-Hydroxy-N-[2-((4-(4-chlorothiophenoxy)thien-3-oyl)amino)ethyl]urea The title compound was obtained following the procedures described in Example 2, but employing 4-(4-chlorothiophenoxy)-3-thiophenecarboxylic acid in lieu of 3-phenoxybenzoate. m.p. 157°–158° C.; ¹H NMR (300 MHz, DMSO-d$_6$); 9.33 (1H, s), 8.23 (1H, t, J=5 Hz), 8.12 (1H, d, J=3 Hz), 7.46 (2H, AB, J=9 Hz), 7.39 (2H, AB, J=9 Hz), 7.01 (1H, d, J=3 Hz), 6.36 (2H, s), 3.30–3.49 (4H, m); MS (M+H)$^+$=340/342. Analysis calc'd for C$_{14}$H$_{14}$N$_3$O$_3$ClS$_2$: C, 45.22; H, 3.79; N, 11.30; Found: C, 45.23; H, 3.80; N, 11.01.

EXAMPLE 60

Preparation of (S)-N-Hydroxy-N-[2-((5-(4-fluorophenoxy)-fur-2-oyl)amino)propyl]urea The title compound was obtained following the procedures described in Example 51, but employing 5-(4-fluorophenoxy)-2-furanoic acid (prepared as in example 36, step 1 by using 4-chlorophenol in lieu of phenol) in lieu of 2-phenoxybenzoate and by employing the N-hydroxy urea from example 42 in lieu of the resultant N-hydroxy urea from example 44. m.p. 125°–127° C.; ¹H NMR (300 MHz, DMSO-d$_6$); 9.32 (1H, s), 8.08 (1H, d, J=9 Hz), 7.20–7.33 (4H, m), 7.08 (1H, d, J=4 Hz), 6.31 (2H, s), 5.79 (1H, d, J=4 Hz), 4.20 (1H, septet, J=7 Hz), 3.47 (2H, ABX, J=14.5, 7 Hz), 3.38 (2H, ABX, J=14.5, 7 Hz), 1.12 (3H, d, J=7 Hz); MS (M+H)$^+$=338; (M+NH$_4$)$^+$=355. Analysis calc'd for C$_{15}$H$_{16}$N$_3$O$_5$F: C, 53.41; H, 4.78; N, 12.46; Found: C, 53.02; H, 4.66; N, 12.27.

EXAMPLE 61

Preparation of N-Hydroxy-N-[2-((5-(4-fluorophenoxy)fur-2-oyl)-amino)ethyl]urea The title compound was obtained following the procedures described in Example 51, but employing 5-(4-fluorophenoxy)-2-furanoic acid (prepared as in example 36, step 1 by using 4-fluorophenol in lieu of phenol) in lieu of 3-phenoxybenzoate. m.p. 176°–178° C.; ¹H NMR (300 MHz, DMSO-d$_6$); 9.29 (1H, s), 8.22 (1H, t, J=5 Hz), 7.20–7.32 (4H, m), 7.09 (2H, d, J=3 Hz), 6.36 (2H, s), 5.92 (1H, d, J=3 Hz), 3.30–3.49 (4H, m); MS (M+H)$^+$=324; (M+NH$_4$)$^+$= 341. Analysis calc'd for C$_{14}$H$_{14}$N$_3$O$_5$F C, 52.02; H, 4.36; N, 13.00; Found: C, 51.60; H, 4.36; N, 12.734.

EXAMPLE 62

Preparation of N-Hydroxy-N-[2-((3-(4-fluorophenylsulfonyl)-benzoyl)amino)ethyl]urea The title compound was obtained following the procedures described in Example 51, but employing 4-(4-chlorophenylsulfonyl)benzoate in lieu of 3-phenoxybenzoate. m.p. 183°–186° C.; ¹H NMR (300 MHz, DMSO-d$_6$); 9.31 (1H, s), 8.22 (1H, t, J=5 Hz), 8.07 (2H, d, J=9.0Hz), 8.01 (4H, d, J=9.0Hz), 7.72 (2H, d, J=9.0Hz), 6.33 (2H, s), 3.38–3.55 (4H, m); MS (M+H)$^+$=399. Analysis calc'd for C$_{16}$H$_{16}$ClN3O5S: C, 48.31; H, 4.05; N, 10.56; Found: C, 48.64; H, 4.64; N, 9.13.

EXAMPLE 63

Preparation of N-Hydroxy-N-[2-((benzo[b]furan-2-oyl)amino)-ethyl]urea

The title compound was obtained following the procedures described in Example 51, but employing benzo[b]furan-2-carboxylic acid in lieu of 3-phenoxybenzoate. m.p. 181°–182° C.; ¹H NMR (300 MHz, DMSO-d$_6$); 9.33 (1H, s), 8.65 (1H, t, J=5 Hz), 7.78 (1H, d, J=7.0 Hz), 7.65 (1H, d, J=7.0 Hz), 7.52 (1H, s), 7.47 (1H, t, J=7.0 Hz), 7.33 (1H, t, J=7.0 Hz), 6.37 (2H, s), 3.42–3.55 (4H, m); MS (M+H)$^+$ =264. Analysis calc'd for C$_{12}$H$_{13}$N$_3$O$_4$: C, 54.75; H, 4.98; N, 15.96; Found: C, 54.69; H, 5.01; N, 15.88.

EXAMPLE 64

Preparation of N-Hydroxy-N-[2-((4-chlorobenzo[b]thien-2-oyl)-amino)ethyl]urea The title compound was obtained following the procedures described in Example 51, but employing benzo[b]thiophene-2-carboxylic acid in lieu of 3-phenoxybenzoate. m.p. 181°–184° C. with decomposition; ¹H NMR (300 MHz, DMSO-d$_6$); 9.34 (1H, s), 8.88 (1H, t, J=5 Hz), 8.20 (1H, s), 8.03 (1H, d, J=8.0 Hz), 7.54 (1H, d, J=8.0 Hz), 7.47 (1H, t, J=8.0 Hz), 6.37 (2H, s), 3.42–3.55 (4H, m); MS (M+H)$^+$=264. Analysis calc'd for C$_{12}$H$_{12}$ClN$_3$OS: C, 45.94; H, 3.86; N, 13.39; Found: C, 45.78; H, 3.62; N, 12.96.

EXAMPLE 65

Preparation of N-Hydroxy-N-[2-((3-benzoylbenzoyl)amino)ethyl]urea

The title compound was obtained following the procedures described in Example 51, but employing 3-benzoylbenzoic acid in lieu of 3-phenoxybenzoate. m.p. 168°–170° C.; ¹H NMR (300 MHz, DMSO-d$_6$); 9.32 (1H, s), 8.70 (1H, t, J=5 Hz), 8.20 (1H, br s), 8.12 (1H, d, J=8.0), 7.88 (1H, d, J=8.0), 7.55–78 (6H, m), 6.35 (2H, s), 3.42–3.55 (4H, m); MS (M+H)$^+$=328, (M+NH$_4$)$^+$= 350. Analysis calc'd for $C_{17}H_{17}N_3O_4$: C, 62.38 H, 5.23; N, 12.84; Found: C, 62.01; H, 5.26; N, 12.60.

EXAMPLE 66

Preparation of
N-Hydroxy-N-[2-((4-(1-phenylethyloxy)benzoyl)-amino)ethyl]urea

The reaction flask was charged with ethyl 4-hydroxybenzoate (10 g, 60 mmol), 1-bromoethylbenzene (11.5 g, 60 mmol), and $K_2CO_3$ (12.4 g, 90 mmol) in dry methylethylketone and the resulting mixture was refluxed for 44 h. After cooling, the reaction mixture was partitioned between ethyl acetate and water. The aqueous layer was extracted with ethyl acetate. The combined organic extracts were dried ($MgSO_4$), filtered and concentrated in vacuo to provide the corresponding phenyl ethyl ester.

The ester (17.49 g, 60 mmol) was dissolved in ethanol (250 mL) and a 1M solution of LiOH (240 mL, 240 mmol) was added. After stirring at ambient temperature for 20 h, the reaction was acidified with 2M aqueous HCl to give a precipitate which was collected by vacuum filtration. The solid was recrystallized from cold (−20° C.) ether to provide the corresponding acid (4.21 g, 29%).

The title compound was obtained following the procedures described in Example 2, but employing 4-(1-phenylethyloxy)benzoic acid in lieu of 3-phenoxybenzoate. m.p. 164°–166° C.; $^1$H NMR (300 MHz, DMSO-$d_6$); 9.31 (1H, s), 8.26 (1H, br t, J=5.5 Hz), 7.66–7.70 (2H, m), 7.22–7.44 (5H, m), 6.92–6.96 (2H, m), 6.30 (2H, br s), 5.59 (1H, q J+6.5 Hz), 3.31–3.50 (4H, m), 1.56 (3H, d, J=6.5 Hz); MS (M+H)$^+$=344. Analysis calc'd for $C_{18}H_{21}N_3O_4$: C, 62.96; H, 6.16; N, 12.24; Found: C, 62.56; H,6.20; N, 12.12.

EXAMPLE 67

Preparation of
N-Hydroxy-N-[2-((3-(1-phenylethyloxy)benzoyl)-amino)ethyl]urea

The title compound was obtained following the procedures described in Example 66, but employing ethyl 3-hydroxybenzoate in lieu of ethyl 4-hydroxybenzoate. m.p. 164°–165° C.; $^1$H NMR (300 MHz, DMSO-$d_6$); 9.32 (1H, s), 8.40 (1H, br t, J=5.5 Hz), 7.21–7.45 (8H, m), 7.01–7.07 (1H, m), 6.32 (2H, br s), 5.56 (1H, q J=6.5 Hz), 3.30–3.52 (4H, m), 1.56 (3H, d, J=6.5 Hz); MS (M+H)$^+$=344; (M+NH$_4$)$^+$=361. Analysis calc'd for $C_{18}H_{21}N_3O_4$: C, 62.96; H, 6.16; N, 12.24; Found: C, 62.52; H, 6.16; N, 12.27.

EXAMPLE 68

Preparation of
N-Hydroxy-N-[2-(((4-(1-phenylethoxy)phenyl)-propion-2-yl)amino)ethyl]urea Methyl 4-hydroxyphenylacetate (15 g, 90.3 mmol) was dissolved in dry DMSO (100 mL) and potassium t-butoxide (10.7 g, 90.3 mmol) was added portionwise. The resulting solution was stirred for 0.5 h at ambient temperature and 1-bromoethylbenzene (12.7 g, 90.3 mmol)was added in a dropwise fashion. The reaction was stirred at ambient temperature for 18 h and partitioned between aqueous ammonium chloride and ether/hexanes (3:1, v:v). The aqueous layer was extracted with the same solvent system (2×) and the organic layers combined, dried ($MgSO_4$), filtered, and concentrated under vacuum. The purified alkylation adduct (16.21 g, 66%)was obtained by FAC (600 g silica gel, 1:9 ether/pentanes).

The alkylation adduct (15 g, 55.55 mmol) was added to a preformed solution of LDA (61 mmol) in dry THF (500 mL) at −78° C. The resulting solution was stirred at −78° C. for 0.5 h and methyl iodide was added to the reaction mixture. The reaction was permitted to warm slowly to 0° C. and quenched by adding excess saturated aqueous ammonium chloride. The two-phased solution was extracted (2×, ethyl acetate). The combined organic layers were washed (1×, 10% aqueous HCl; 1×, saturated aqueous NaHCO$_3$; 1×, brine), dried (MgSO$_4$), filtered and concentrated in vacuo to provide the unpurified alkylation adduct (15.8 g,~100%) which was carried on without further purification.

Hydrolysis was carried out as described in example 66 to provide the corresponding acid which was convened to the title compound as described in example 2. m.p. 163°–168° C.; $^1$H NMR (300 MHz, DMSO-$d_6$); 9.23 (1H, s), 7.82–7.88 (1H, m), 7.20–7.41 (2H, m), 7.07–7.12 (2H, m), 6.78–6.82 (2H, m), 6.38 (2H, br s), 5.44 (1H, q, J=6.5 Hz), 3.03–3.48 (5H, m), 1.52 (3H, d, J=6.5 Hz), 1.22 (3H, d, J=7.0 Hz); MS (M+H)$^+$=372. Analysis calc'd for $C_{20}H_{25}N_3O_4$ (0.25 H$_2$O): C, 63.90; H, 6.83; N, 11.18; Found: C, 63.73; H, 6.72; N, 11.11.

EXAMPLE 69

Preparation of
N-Hydroxy-N-[2-(((3-(1-phenylethoxy)phenyl)-propion-2-yl)amino)ethyl]urea The title compound is obtained following the procedures described in Example 69, but employing ethyl 3-hydroxyphenylacetic acid in lieu of methyl 4-hydroxyphenylacetic acid.

EXAMPLE 70

Preparation of
N-Hydroxy-N-[2-(((2-(1-phenylethoxy)phenyl)-propion-2-yl)amino)ethyl]urea The title compound is obtained following the procedures described in Example 69, but employing ethyl 2-hydroxyphenylacetic acid in lieu of methyl 4-hydroxyphenylacetic acid.

EXAMPLE 71

Preparation of
N-Hydroxy-N-[2-((3-phenoxyphenoxyacetyl)-amino)ethyl]urea t-Butyl (3-phenoxy)phenoxyacetate was prepared following the alkylation procedure as described in example 66 using 3-phenoxyphenol and acetone in lieu of ethyl 4-hydroxybenzoate and methylethylketone.

The t-butyl ester was removed by treatment of the phenoxyacetate (5 g, 16.7 mmol) with equal volumes (67 mL) of TFA and dichloromethane and ambient temperature for three hours. The volatiles were removed in vacuo. The resulting oil was taken up in toluene and concentrated (2 cycles), then taken up in dichloromethane and concentrated (1×) to remove excess trifluoroacetic acid to give the corresponding acid as a dark oil which was carried on without further purification.

The title compound was prepared as in example 2 employing 3-phenoxyphenoxyacetic acid prepared as described in example 72 in lieu of 3-phenoxybenzoic acid. m.p. 153°–155° C.; $^1$H NMR (300 MHz, DMSO-d$_6$); 9.30 (1H, s), 8.08 (1H, t, J=6.0 Hz), 7.26–7.45 (3H, m), 7.12–7.19 (2H, m), 7.00–7.06 (2H, m), 6.71–6.77 (1H, m), 6.57–5.62 (2H, m), 6.32 (2H, br s), 4.45 (2H, s), 3.25–3.43 (4H, m); MS (M+H)$^+$=346; (M+NH$_4$)$^+$=363. Analysis calc'd for C$_{17}$H$_{19}$N$_3$O$_5$: C, 59.12; H, 5.54; N, 12.17; Found: C, 58.79; H, 5.50; N, 12.60.

EXAMPLE 72

Preparation of N-Hydroxy-N-[2-((4-phenoxyphenoxyacetyl)-amino)ethyl]urea

The title compound is obtained following the procedures described in Example 72, but employing 4-phenoxyphenol in lieu of 3-phenoxyphenol.

EXAMPLE 73

Preparation of N-Hydroxy-N-[2-((2-phenoxyphenoxyacetyl)-amino)ethyl]urea

The title compound is obtained following the procedures described in Example 72, but employing 2-phenoxyphenol in lieu of 3-phenoxyphenol.

EXAMPLE 74

Preparation of N-Hydroxy-N'-methyl-N-[2-((quinolin-2-oyl)-amino)ethyl]urea

The title compound was obtained following the procedures described in Example 2, but employing 2-quinolinecarboxylic acid in lieu of 3-phenoxybenzoate and MeNCO in lieu of TMSNCO. m.p. 158°–159° C.; $^1$H NMR (300 MHz, DMSO-d$_6$); 9.35 (1H, s), 8.93 (1H, m), 8.57 (1H, d, J=8.5 Hz), 8.06–8.19 (3H m), 7.85–7.91 (1H, m), 7.70–75 (1H, m), 6.98 (1H, q, J=5.0 Hz), 3.52–3.59 (4H, m), 2.57 (3H, d, J=5.0 Hz); MS (M+H)$^+$=289. Analysis calc'd for C$_{14}$H$_{16}$N$_4$O$_3$: C, 58.32 H, 5.59; N, 19.43; Found: C, 58.34; H, 5.60; N, 19.47.

EXAMPLE 75

Preparation of N-Hydroxy-N-[2-((quinolin-2-oyl)amino)ethyl]urea

The title compound was obtained following the procedures described in Example 2, but employing TMSNCO in lieu of MeNCO. m.p. 189°–190° C.; $^1$H NMR (300 MHz, DMSO-d$_6$); 9.42 (1H, s), 8.96 (1H, m), 8.58 (1H, d, J=8.5 Hz), 8.07–8.19 (3H, m), 7.84–7.91 (1H, m), 7.70–75 (1H, m), 6.39 (2H, s), 3.54–3.59 (4H, m); MS (M+H)$^+$=275. Analysis calc'd for C$_{13}$H$_{14}$N$_4$O$_3$: C, 56.93 H, 5.15; N, 20.43; Found: C, 56.99; H, 5.19; N, 20.24.

EXAMPLE 76

Preparation of N-Hydroxy-N-[2-(((3-(6-methoxynaphth-2-yl)-2-methyl-prop-2-enyl)carbonyl)amino)ethyl] urea To an ice-cooled, magnetically stirred solution of the 6-methoxy-2-napthylnitrile (10.0 g, 54.6 mmol) in dry THF (100 mL) was added dropwise 60 mL of 1M DIBAL in methylene chloride under nitrogen. After 16 h at ambient temperature, the reaction was quenched with methanol (dropwise addition). The resulting suspension was treated with aqueous citric acid and extracted with EtOAc (3×200 mL). The combined organic extracts were dried(MgSO$_4$), filtered, and concentrated to give the corresponding aldehyde (used directly in the next step).

To a magnetically stirred solution of the aldehyde in dry THF (150 mL) was added (carbethoxyethylidene)triphenylphosphorane(18.1 g, 49.9 mmol) in several portions over 2 h. After 16 h, the reaction was concentrated and hexane was added to precipitate the triphenylphosphine oxide, which was removed by vacuum filtration and washed with hexane. The filtrate was chromatographed (100 g silica gel, EtOAc-hexane (20:80)) to give the desired (E)-α,β-unsaturated ester (10.0 g, 68%).

To a magnetically stirred solution of the ester (6.26 g, 23.2 mmol) in THF (60 mL) and isopropanol (60 mL) was added dropwise 25 mL of 1M aqueous LiOH. After 1 h, the reaction was acidified with aqueous citric acid and extracted with EtOAc (4×100 mL). The combined organic extracts were dried(MgSO4), filtered, and concentrated to provide the corresponding acid (4.64 g, 82%).

The title compound was obtained following the procedures described in Example 2, but employing acid prepared above in lieu of 3-phenoxybenzoic acid. m.p. 174°–176° C.; $^1$H NMR (300 MHz, DMSO-d$_6$); 9.18 (1H, s), 8.02 (1H, t, J= 5.5 Hz), 7.85 (3H, m), 7.50 (1H, dd, J=8.5,1.5), 7.35 (2H, m), 7.18 (1H, dd, J=9,2.5), 6.53 (2H, s), 3.89 (3H, s), 3.27–3.49 (4H, m), 2.10 (3H, d, J=1.5 Hz); MS (M+H)$^+$= 344. Analysis calc'd for C$_{18}$H$_{21}$N$_3$O$_4$: C, 62.96 H, 6.16; N, 12.24; Found: C, 62.80; H, 6.02; N, 12.00.

EXAMPLE 77

Preparation of N-Hydroxy-N-[2-((3-phenylpropionyl)amino)ethyl]urea

The title compound was obtained following the procedures described in Example 2, but employing dihydrocinnamate in lieu of 3-phenoxybenzoic acid. m.p. 165°–167° C.; $^1$H NMR (300 MHz, DMSO-d$_6$); 7.75 (1H, t, J=5.5 Hz), 7.05–7.20 (5H, m), 6.97 (2H, m), 6.43 (2H, s), 3.36 (2H, t, J=7.0 Hz), 3.10 (2H, q, J=6.5 Hz), 2.71 (2H, dd, J=8.0,7.5 Hz), 2.26 (2H, dd, J=8.0,7.5 Hz); MS (M+H)$^+$=252. Analysis calc'd for C$_{12}$H$_{17}$N$_3$O$_3$: C, 57.36 H, 6.82; N, 16.72; Found: C, 57.22; H, 6.71; N, 16.52.

EXAMPLE 78

Preparation of N-Hydroxy-N-[2-((3-(4-n-butoxyphenyl)prop-2-enoyl)amino)ethyl]urea Following the procedure of Meyer (Campaigne, E.; Meyer, W. W. *J. Org. Chem.* 1962, 27, 2835) 4-butoxybenzaldehyde was converted to methyl 4-butoxycinnamate Hydrolysis of the ester to the corresponding acid 1, was completed following the procedure as described in example 77. The title compound was obtained following the procedures described in Example 2, but employing acid prepared above in lieu of 3-phenoxybenzoic acid. m.p. 127°–129° C.; $^1$H NMR (300 MHz, DMSO-$d_6$); 9.31 (1H, s), 8.02 (1H, t, J=5.5 Hz), 7.48 (2H, d, J=8.5 Hz), 7.36 (1H, d, J=16.0), 6.96 (2H, d, J=8.5 Hz), 6.52 (1H, d, J=16.0), 4.74 (2H, br s), 3.99 (2H, t, J=6.5), 3.45 (2H, t, J=6.0 Hz), 3.24 (2H, q, J=6.0 Hz), 1.70 (2H, m), 1.43 (2H, m), 0.93 (3H, t, J=7.5 Hz); MS (M+H)$^+$=322. Analysis calc'd for $C_{16}H_{23}N_3O_4$: C, 59.80 H, 7.21; N, 13.08; Found: C, 59.65; H, 7.05; N, 12.90.

EXAMPLE 79

Preparation of N-Hydroxy-N-[2-((3-(3-n-butoxyphenyl)prop-2-enoyl)amino)ethyl]urea The title compound is obtained following the procedures described in Example 79, but employing 3-butoxybenzaldehyde in lieu of 4-butoxybenzaldehyde.

EXAMPLE 80

Preparation of N-Hydroxy-N-[2-((3-(2-n-butoxyphenyl)prop-2-enoyl)amino)ethyl]urea The title compound is obtained following the procedures described in Example 79, but employing 2-butoxybenzaldehyde in lieu of 4-butoxybenzaldehyde.

EXAMPLE 81

Preparation of N-Hydroxy-N-[2-((2-(6-methoxynaphth-2-yl)-propionyl)amino)ethyl] urea The title compound was obtained following the procedures described in Example 2, but employing naproxen in lieu of 3-phenoxybenzoate. m.p. 161.5°– 162.5° C.; $^1$H NMR (300 MHz, DMSO-$d_6$); 9.27 (1H, s), 7.92 (1H, t, J=5.5 Hz), 7.19 (2H, AB, J=9.0 Hz), 7.06 (2H, AB, J=9.0 Hz), 6.31 (2H, s), 3.86 (3H, s), 3.70 (1H, q, J=7.0 Hz), 3.10–3.38 (4H, m), 1.90 (3H, d, J=7.0 Hz); MS (M+H)$^+$=332; (M=NH$_4$)$^+$= 349. Analysis calc'd for $C_{17}H_{21}N_3O_4$ (0.25 H$_2$O): C, 60.79 H, 6.45; N, 12.51; Found: C, 60.78; H, 6.34; N, 12.45.

EXAMPLE 82

Preparation of N-Hydroxy-N-[2-((2-(4-(2-methylpropyl)phenyl)-propionyl)amino)ethyl]urea The title compound was obtained following the procedures described in Example 2, but employing ibuprofen in lieu of 3-phenoxybenzoate. m.p. 150.5°– 152.5° C.; $^1$H NMR (300 MHz, DMSO-$d_6$); 9.27 (1H, s), 7.99 (1H, t, J=5.5 Hz), 7.78 (1H, d, J=9.0 Hz), 7.75 (1H, d, J=9.0 Hz), 7.70 (1H, s), 7.42 (1H dd, J=9.0,2.0 Hz), 7.27 (1H, d, J=2.0 Hz), 7.13 (1H, dd, J=9.0,2.0 Hz), 6.31 (2H, s), 3.52 (1H, q, J=7.0 Hz), 3.07–3.38 (4H, m), 2.39 (2H, d, J=7.0 Hz), 1.79 (1H, septet, J=7.0 Hz), 1.30 (3H, d, J=7.0 Hz), 0.84 (6H, d, J=7.0 Hz); MS (M+H)$^+$=308. Analysis calc'd for $C_{16}H_{25}N_3O_3$: C, 62.52 H, 8.20; N, 13.67; Found: C, 62.69; H, 8.31; N, 13.58.

EXAMPLE 83

Preparation of N-Hydroxy-N-[2-((2-(2,6-dichlorophenylamino)-phenylacetyl)amino)ethyl] urea The title compound was obtained following the procedures described in Example 2, but employing diclofinac in lieu of 3-phenoxybenzoate. A lactam was the product from the attempted acid chloride formation. The normal mitsunobu intermediate was prepared by heating the lactam in the presence of ethanolamine. m.p. 187°–189° C.; $^1$H NMR (300 MHz, DMSO-$d_6$); 9.31 (1H, s), 8.37 (1H, t, J= 5.5 Hz), 8.32 (1H, s), 7.52 (2H, d, J=8.0 Hz), 7.18 (1H, rid, J=8.0,1.5 Hz), 7.15 (1H, t, J=8.0 Hz), 7.03 (1H, dd, J=8.0,1.5 Hz), 6.83 (1H, dd, J=8.0,1.5 Hz), 6.31 (2H, s), 6.28 (1H, dd, J=8.0,1.5 Hz), 3.57 (2H, s), 3.40 (2H, m), 3.25 (2H, m); MS (M+H)$^+$=397/399/401. Analysis calc'd for $C_{17}H_{18}N_4O_3Cl_2$: C, 51.40 H, 4.57; N, 14.10; Found: C, 51.07; H, 4.45; N, 13.98.

EXAMPLE 84

Preparation of N-Hydroxy-N-[2-((2-phenylthiazol-4-oyl)amino)-ethyl]urea

The title compound was obtained following the procedures described in Example 2, but employing 2-phenylthiazol-4-carboxylic acid in lieu of 3-phenoxybenzoate. m.p. 188°–192° C. with decomposition; $^1$H NMR (300 MHz, DMSO-$d_6$); 9.48 (1H, s), 8.55 (1H, t, J=5 Hz), 8.04–8.07 (2H, m), 7.53–7.58 (4H, m), 6.35 (2H, s), 3.45–3.55 (4H, m); MS (M+H)$^+$=307, (M+NH$_4$)$^+$= 324. Analysis calc'd for $C_{13}H_{14}N_4O_3S$ (0.75 H$_2$O): C, 49.07; H, 4.45; N, 17.18; Found: C, 48.82; H, 4.88; N, 17.52.

EXAMPLE 85

Preparation of (d,l)-N-Hydroxy-N-[3-((tert-butyoxycarbonyl)-amino)prop-2-yl]urea A one liter roundbottom flask was charged with dichloromethane (450 mL) and di-t-butyldicarbonate (11.04 g, 0.146 mol). A dichloromethane (100 mL) solution of 1-amino-2-propanol (29 g, 0.154 mol) was added dropwise. The resulting mixture was stirred one h at room temperature and partitioned between 10% aqueous HCl and dichloromethane. The aqueous layer was extracted (2×) with dichloromethane. The combined organic extracts were washed (1×, sat'd NaHCO$_3$; 1×, brine), dried (MgSO$_4$), filtered and concentrated in vacuo to give a light yellow liquid (26.5 g, 103%). The resulting N-Boc-1-amino-2-propanol was carried on without further purification.

A one liter roundbottom flask was charged with N-Boc-1-amino-2-propanol (26.42 g, 0.0151 mol), triphenylphosphine (41.4 g, 0.158 mol), and N,O-bisphenyloxycarbonylhydroxylamine (43.2 g, 0.158 mol), and dry THF (550 mL). The solution was cooled to 0° C., and diethylazodicarboxylate (24.9 mL, 0.158 mol) was added in THF (50 mL). The reaction was stirred one hour after removing the cooling bath, and concentrated under vacuum. Chromatographic purification is enhanced by adding dichloromethane (200 mL) and concentrating in vacuo twice to remove THF before column chromatography (400 g silica gel, 15% EtOAc/Hex) to provide N,O-bisphenyloxycarbonyl-t-butyloxycarbonylamino-2-propylhydroxylamine (54.4 g, 80%).

A resealable tube was charged with a solution of the N,O-diphenyloxycarbonylpropylhydroxylamine (22 g, 0.051 mol, prepared above) in the minimum volume of ether (10 mL). The solution was cooled to −23° C. and liquid ammonia (100 mL) was condensed into the resealable tube. The tube was sealed, the cooling bath removed, and the reaction stirred overnight (~17 h). After cooling the tube, the seal was removed and the ammonia evaporated to give a brown residue which was purified by chromatography (400 g silica gel, 40% EtOAc/$CH_2Cl_2$ (2.5 L) then 5% MeOH/$CH_2Cl_2$ (2 L)) to provide a white solid which was triturated with ether to provide the title compound (6.54 g, 55%). m.p. 158°–159° C.; $^1$H NMR (300 MHz, DMSO-$d_6$); 8.33 (1H, s), 5.13 (2H, br s), 5.0 (1H, br m), 4.33 (ddd, J=14.5, 12, 9 Hz; MS (M+H)$^+$=234, (M+NH$_4$)$^+$= 251. Analysis calc'd for $C_{13}H_{14}N_4O_3S$ (0.75 $H_2O$): C, 46.86; H, 8.21; N, 18.01; Found: C, 46.86; H, 8.54; N, 18.13.

EXAMPLE 86

Preparation of N-Hydroxy-N-[3-((5-(4-fluorophenoxy)furan-2-oyl)-amino)prop-2-yl]urea The title compound was obtained following the procedures described in Example 51, but employing 2-N-Hydroxy-1-t-butyloxycarbonylamino-propylurea (prepared as described in example 85) in lieu of (S)-N-Hydroxy-2-t-butyloxycarbonylamino-propylurea. M.p. 180–181° C.; $^1$H NMR (300 MHz, DMSO-$d_6$); 8.78 (1H, s), 8.14 (1H, t, J=7.5,7.5 Hz), 7.20–7.33 (4H, m), 7.08 (1H, d, J=4 Hz), 6.34 (2H, s), 5.79 (1H, d, J=4 Hz), 4.20 (1H, br sextet, J= 7.5 Hz), 3.32 (2H, dt, J=14.5, 7, 7 Hz), 3.14 (2H, ddd, J=14.5, 6, 9 Hz), 0.97 (3H, d, J=7 Hz); MS (M+H)$^+$=338. Analysis calc'd for $C_{15}H_{16}N_3O_5F$: C, 53.41; H, 4.78; N, 12.46; Found: C, 53.43; H, 4.55; N, 12.47.

EXAMPLE 87

Preparation of N-Hydroxy-N-2-((2-(1-phenylethyloxy)benzoyl)-amino)ethyl]urea The title compound was prepared following the method of Example 66 but employing ethyl 2-hydroxybenzoate in lieu of ethyl 4-hydroxybenzoate.

EXAMPLE 88

Preparation of N-Hydroxy-N-[4-((5-(4-fluorophenoxy)furan-2-oyl)-amino)but-2yl]urea The title compound was obtained following the procedures described in Example 2, but employing 5-(4-fluorophenoxy)-2-furanoic acid in lieu of 3-phenoxybenzoic acid and 1-aminobutan-3-ol in lieu of ethanol amine. m.p. 161°– 163° C.; $^1$H NMR (300 MHz, DMSO-$d_6$); 8.90 (1H, s), 8.14 (1H, t, J=7.5,7.5 Hz), 7.20–7.33 (4H, m), 7.08 (1H, d, J=4 Hz), 6.30 (2H, s), 5.79 (1H, d, J=4 Hz), 4.13 (1H, br sextet, J=7.5 Hz), 3.27 (2H, br m), 3.10 (2H, br m), 1.72 (1H, sextet, J=7.5 Hz), 1.53 (1H, sextet, J=7.5 Hz), 1.01 (3H, d, J=7.5 Hz); MS (M+H)$^+$=352, (M+NH$_4$)$^+$=251. Analysis calc'd for $C_{16}H_{18}N_3O_5F$: C, 54.70; H, 5.16 N, 11.46; Found: C, 54.14; H, 5.24; N, 11.46.

The substituted amide-linked N-hydroxyureacompounds of Examples 89– 128 as shown in Table 3 are prepared by the method used for Example 2 substituting m-phenoxybenzoic acid with the requisite substituted benzoic acid derivative which can be prepared according to the alkylation procedure outlined in example 23.

TABLE 3

Substituted Hydroxybenzoate Amide-linked N-Hydroxyureas

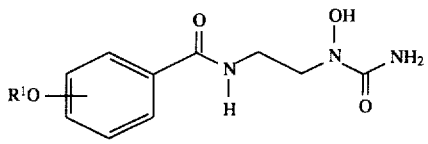

| Example | R$_1$ |
|---|---|
| 89 | —(CH$_2$)$_2$CH$_3$ |
| 90 | —(CH$_2$)$_3$CH$_3$ |
| 91 | —(CH$_2$)$_4$CH$_3$ |
| 92 | —(CH$_2$)$_5$CH$_3$ |
| 93 | —CH$_2$CH(CH$_3$)$_2$ |
| 94 | —(CH$_2$)$_2$CH(CH$_3$)$_2$ |
| 95 | —(CH$_2$)$_3$CH(CH$_3$)$_2$ |
| 96 | —(CH$_2$)$_4$CH(CH$_3$)$_2$ |
| 97 | —CH$_2$CH=CH$_2$ |
| 98 | -trans-CH$_2$CH=CHCH$_3$ |
| 99 | -trans-CH$_2$C(CH$_3$)=CHCH$_3$ |
| 100 | —CH$_2$CH=C(CH$_3$)CH$_3$ |
| 101 | —CH$_2$CH$_2$N(CH$_3$)$_2$ |
| 102 | —CH$_2$CH$_2$N(CH$_2$CH$_3$)$_2$ |
| 103 | —(CH$_2$)$_2$CH$_2$N(CH$_3$)$_2$ |
| 104 | —(CH$_2$)$_2$CH$_2$N(CH$_2$CH$_3$)$_2$ |
| 105 | —CH$_2$-2-pyridyl |
| 106 | —CH$_2$-3-pyridyl |
| 107 | —CH$_2$-4-pyridyl |
| 108 | —CH$_2$-2-furyl |
| 109 | —CH$_2$-3-furyl |
| 110 | —CH$_2$-2-thienyl |
| 111 | —CH$_2$-3-thienyl |
| 112 | —CH$_2$-2-benzo[b]thienyl |
| 113 | —CH$_2$-2-benzo[b]furyl |
| 114 | —CH$_2$-2-thiazoyl |
| 115 | —CH$_2$-2-imidazoyl |
| 116 | —CH(CH$_3$)-2-pyrimidyl |
| 117 | —CH(CH$_3$)-2-pyridyl |
| 118 | —CH(CH$_3$)-3-pyridyl |
| 119 | —CH(CH$_3$)-4-pyridyl |
| 120 | —CH(CH$_3$)$_2$-2-furyl |
| 121 | —CH(CH$_3$)-3-furyl |
| 122 | —CH(CH$_3$)-2-thienyl |
| 123 | —CH(CH$_3$)-3-thienyl |
| 124 | —CH(CH$_3$)-2-benzo[b]thienyl |
| 125 | —CH(CH$_3$)$_2$-2-benzo[b]furyl |
| 126 | —CH(CH$_3$)-2-thiazoyl |
| 127 | —CH(CH$_3$)-2-imidazoyl |
| 128 | —CH(CH$_3$)-2-pyrimidyl |

The substituted benzoate amide-linked N-hydroxyurea compounds of Examples 129–153 shown in Table 4 were prepared following the procedures described in example 51 by employing the appropriate aryl acid and substituted N-hydroxy-N-[ 2-((tert-butoxycarbonyl)amino)ethyl]urea (examples 42, 43, 44). The starting 3-aryloxy- and 3-thioaryloxy benzoic acids were either commercially available or were prepared by an Ullman coupling (see Fanta, F. E. Chem. Rev. 1946, 38, 139) between the appropriate phenol/thiophenol and aryl halide. The 5-thioaryloxy and 5-aryloxy 2-furoic acid derivatives were prepared as described in example 36 for the preparation of 5-phenoxy-2-furoic acid from commercially available precursors.

TABLE 4

Substituted Benzoate Amide-linked N-Hydroxyureas

Ar¹—X—Ar²—N(H)—C(R¹)(R²)—N(OH)—C(O)—NH₂

| Ex. | Ar¹ | X | Ar² | R¹ | R² | mp |
|---|---|---|---|---|---|---|
| 129 | Phenyl | O | 1,3-benzoyl | (S)-Me | H | 132–134 |
| 130 | 4-Fluorophenyl | O | 1,3-benzoyl | (S)-Me | H | 115–117 |
| 131 | 4-Fluorophenyl | O | 4-MeO-1,3-benzoyl | H | H | 148–149 |
| 132 | 4-methylphenyl | O | 2,5-furanoyl | H | Me | 169–171 |
| 133 | 4-Fluorophenyl | S | 2,5-furanoyl | H | H | 158–160 |
| 134 | 4-chlorophenyl | O | 1,3-benzoyl | H | Me | 186–189 |
| 135 | 4-Fluorophenyl | O | 4-Br-2,5-furanoyl | H | H | 194–197 decomp |
| 136 | 4-Fluorophenyl | S | 2,5-furanoyl | (R)-Me | H | 115–116 |
| 137 | 4-Fluorophenyl | O | 4-Br-2,5-furanoyl | (R)-Me | H | 153–156 |
| 138 | 4-Fluorophenyl | S | 2,5-furanoyl | H | Me | 172–175 |
| 139 | 4-Fluorophenyl | S | 2,5-furanoyl | (R)-Me | H | 161–164 |
| 140 | 4-Fluorophenyl | O | 2,5-furanoyl | (R)-i-Pr | H | 150–152 |
| 141 | Phenyl | S | 2,5-thiophenoyl | H | Me | 174–180 decomp |
| 142 | 4-Fluorophenyl | O | 2,5-furanoyl | H | (R)-Me | 182–183 |
| 143 | 4-Fluorophenyl | O | 2,5-furanoyl | H | (S)-Me | 177–178 |
| 144 | n-Butyl | O | 1,3-benzoyl | H | Me | 194–195 |
| 145 | 2,4-Difluorophenyl | O | 2,5-furanoyl | H | Me | 183–184 |
| 146 | Phenyl | O | 2,5-furanoyl | H | Me | 153–155 |
| 147 | 4-Methylphenyl | O | 2,5-furanoyl | H | Me | 182–184 |
| 148 | 4-Fluorophenyl | O | 2,5-thiophenoyl | H | Me | 193–194 |
| 149 | Napth-2-yl | O | 2,5-furanoyl | H | Me | 193–196 |
| 150 | 3,4-Difluorophenyl | O | 2,5-furanoyl | H | Me | 201–202 |
| 151 | 4-Cyanophenyl | O | 2,5-furanoyl | H | Me | 164–170 |
| 152 | 3-pyridyl | O | 2,5-furanoyl | H | Me | decomp |
| 153 | 4-Chlorophenyl | O | 1,3-benzoyl | (S)-Me | H | 155–156 |

EXAMPLE 154

Preparation of
N-Hydroxy-N-2-[(3-(4-bromophenyl)propenoyl)-amino]ethyl urea

Following the procedure outlined in example 51 but employing 4-bromocinammoyl chloride in lieu of 2-phenoxybenzoyl chloride provided the title compound as a colorless solid after chromatographic purification. m.p. 143°–145° C.; ¹H NMR (300 MHz, D₆-DMSO) 9.30 (1H, s), 8.16 (1H, t, J=5.5,5.5 Hz), 7.61 (2H, d, J=8.5 Hz), 7.51 (2H, d, J=8.5 Hz), 7.39 (1H, d, J=16 Hz), 6.70 (1H, d, J=16 Hz), 6.25 (2H, s), 3.43 (2H, m), 3.36 (2H, m). Analysis calc'd for C12H$_{14}$N$_3$O$_3$Br: C, 43.92; H, 4.30; N, 12.80; Found: C, 43.70; H, 4.35; N, 12.60.

EXAMPLE 155

Preparation of
N-Hydroxy-N-2-((3-phenylpropenoyl)amino]ethyl urea

Following the procedure outlined in example 51 but employing cinammoyl chloride in lieu of 2-phenoxybenzoyl chloride provided the title compound as a colorless solid after chromatographic purification. m.p. 160°–162° C.; ¹H NMR (300 MHz, D$_6$-DMSO) 9.32 (1H, s), 8.14 (1H, t, J=5.5,5.5 Hz), 7.56 (2H, dd, J=8.5,1 Hz), 7.35–7.46 (4H, m), 6.63 (1H, d, J=16 Hz), 6.32 (2H, s), 3.43 (2H, br t, J=6.5 Hz), 3.36 (2H, br t, J=6.5 Hz). Analysis calc'd for C$_{12}$H$_{15}$N$_3$O$_3$: C, 57.82; H, 6.07; N, 16.86; Found: C, 57.60; H, 5.91; N, 16.79.

EXAMPLE 156

Preparation of
(R)-N-Hydroxy-N-2-[(3-(4-bromophenyl)propenoyl)-amino]propyl urea Following the procedure outlined in example 78052 but employing (R)-N-hydroxy-N-[ 2-((tert-butoxycarbonyl)amino)propyl]urea in lieu of N-hydroxy-N-[ 2-((tert-butoxycarbonyl) amino)ethyl]urea provided the title compound as a colorless solid after recrystallization from methanol. m.p. 192°–193.5° C.; ¹H NMR (300 MHz, D$_6$-DMSO) 9.30 (1H, s), 8.08 (1H, d, J=9 Hz), 7.61 (2H, d, J=8.5 Hz), 7.51 (2H, d, J=8.5 Hz), 7.39 (1H, d, J=16 Hz), 6.63 (1H, d, J=16 Hz), 6.28 (2H, s), 4.16 (1H, septet, J=7.5 Hz), 3.36 (2H, d, J=7.5 Hz), 1.09 (3H, d, J=7.5 Hz); MS (M+NH$_4$)$^+$=359. Analysis calc'd for C$_{13}$H$_{16}$N$_3$O$_3$Br: C, 45.63; H, 4.71; N, 12.28; Found: C, 45.33; H, 4.69; N, 12.05.

EXAMPLE 157

Preparation of
(d,l)-N-Hydroxy-N-3-[(3-(4-bromophenyl)-propenoyl)amino]prop- 2-yl urea Following the procedure outlined in example 78052 but employing N-hydroxy-N-[ 3-((tert-butyoxycarbonyl)amino- )prop-2-yl]urea in lieu of N-hydroxy-N-[ 2-((tert-butoxycarbonyl) amino)ethyl]urea provided the title compound as colorless solid after recrystallization from methanol. m.p. 199°–200.5° C.; $^1$H NMR (300 MHz, D$_6$-DMSO) 8.88 (1H, s), 8.08 (1H, d, J=9 Hz), 8.17 (1H, t, J=6 Hz), 7.61 (2H, d, J=8.5 Hz), 7.53 (2H, d, J=8.5 Hz), 7.41 (1H, d, J=16 Hz), 6.69 (1H, d, J=16 Hz), 6.30 (2H, s), 4.18 (1H, sextet, J=7.5 Hz), 3.25 (2H, t, J=7.5 Hz), 0.98 (3H, d, J=7.5 Hz); MS (M+H)$^+$=342, (M+NH$_4$)$^+$=359. Analysis calc'd for C$_{13}$H$_{16}$N$_3$O$_3$Br(0.2 H$_2$O): C, 45.15; H, 4.78; N, 12.15; Found: C, 44.89,; H, 4.78; N, 12.15.

EXAMPLE 158

Preparation of N-Hydroxy-N-2-((3-(4-bromophenyl)propanoyl)-amino]ethyl urea

Following the procedure outlined in example 51 but employing 3-(4-bromophenyl)propionyl chloride (prepared by reduction of 4-bromocinnamic acid over 5% Pt/C in ethyl acetate at 4 atm of hydrogen and subsequent conversion to the acid chloride with oxalyl chloride) in lieu of 2-phenoxybenzoyl chloride provided the title compound as a colorless solid after recrystallization from methanol. m.p. 177.5°–179° C.; $^1$H NMR (300 MHz, D$_6$-DMSO) 9.27 (1H, s), 7.87 (1H, t, J=5.5,5.5 Hz), 7.46 (2H, d, J=8.5 Hz), 7.26 (2H, d, J=8.5 Hz), 6.30 (2H, s), 3.43 (2H, br t, J=7.5 Hz), 3.20 (2H, br q, J=7.5 Hz), 2.77 (2H, t, J=7.5 Hz), 2.35 (2H, t, J=7.5 Hz); MS (M+H)$^+$=330/332. Analysis calc'd for C12H$_{16}$N$_3$O$_3$Br(0.1 H$_2$O): C, 43.42; H, 4.92; N, 12.66; Found: C, 43.07; H, 4.64; N, 12.54.

EXAMPLE 159

Preparation of N-Hydroxy-N-2-[(3-(3-(4-chlorophenoxy)phenyl)-propynoyl)amino]ethyl urea Ethyl 3-(3-(4-chlorphenoxy)phenyl)propynoate was prepared by adding anhydrous powdered K$_2$CO$_3$ (4.14 g, 30 mmol) portionwise to a suspension of 3-( 4-chlorophenoxy)benzaldehyde (2.33 g, 10 mmol) and ethyl 2-iodo-2-(triphenylphosphonium)acetate iodide (8.43 g, 14 mmol) in dry methanol (60 mL). The reaction was stirred overnight at ambient temperature, diluted with a 1:1 solution of ethyl acetate and hexanes, and filtered. The filtrate was concentrated and chromatographed on silica gel (100 g) using 10% ethyl acetate/hexanes and then 20% ethyl acetate/hexanes as the eluant. The alkynoic ester was convened to the mixed anhydride by first hydrolyzing the ester (301 mg, 1 mmol) by exposure to an aqueous solution of LiOH (1.1 mL, 1M solution) in absolute ethanol (5 mL) at ambient temperature. The reaction was judged complete after 45 minutes and the volatiles were removed under reduced pressure. The residue was vacuum dried, suspended in dichloromethane (8 mL), and treated with isobutyl chlorformate (0.14 g, 1 mmol) under an argon atmosphere. After 30 minutes N-hydroxy-N-[2-((tert-butoxycarbonyl) amino)ethyl]urea (0.22 g, 1 mmol) and triethylamine (0.126 g, 1.25 mmol) were added and the resulting mixture was stirred for 1 h at ambient temperature and concentrated under vacuum. The residue was dissolved in dichloromethane(8 mL), glacial acetic acid (1 mL), and boron trifluoride etherate (0.25 mL). After 30 minutes the reaction was carefully neutralized with excess saturated aqueous sodium bicarbonate and extracted with ethyl acetate. The title compound was obtained as a colorless solid after chromatographic purification over silica gel using ethyl acetate as the eluant. m.p. 140°–142° C.; $^1$H NMR (300 MHz, D$_6$-DMSO) 9.28 (1H, s), 8.01 (1H, t, J=5.5,5.5 Hz), 7.00–7.5 (4H, m), 7.46 (2H, d, J=8.5 Hz), 7.10 (2H, d, J=8.5 Hz), 6.30 (2H, s), 3.2–3.4 (4H, m); MS (M+H)$^+$=374. Analysis calc'd for C$_{18}$H$_{16}$N$_3$O$_4$Cl: C, 57.84; H, 4.31; N, 11.24; Found: C, 57.60; H, 4.25; N, 11.10.

EXAMPLE 160

Preparation of N-Hydroxy-N-2-[N"-benzyloxycarbonyl-((3-phenoxyphenyl) methyl)amino]ethyl urea Step 1: Preparation of N-2-((3-phenoxyphenyl)methyl)-2-aminoethanol.

The title compound was prepared following the procedure described in example 37, step 1, but employing 2-aminoethanol in lieu of N-methyl ethanolamine and employing 3-phenoxybenzaldehyde in lieu of 3-(4-chlorophenoxy)benzaldehyde.

Step 2; Preparation of N-benzyloxycarbonyl-N-((3-phenoxyphenyl)methyl)-2-aminoethanol.

The resulting compound (2.78 g, 11.4 mmol) from step 1 and tritheylamine (2.4 mL, 17.2 mmol) were dissolved in dichloromethane (30 mL). To the solution was added carbobenzyloxychloride (1.9 mL, 12.6 mmol) in dichloromethane (15 mL). After 0.5 h the reaction was partitioned between 10% aqueous HCl and s dichloromethane. The layers were separated and the aqueous layer was extracted with dichloromethane. The combined organic layers were washed (1×, saturated sodium bicarbonate; 1×, brine), dried over MgSO$_4$, and concentrated under vacuum to provide the title compound (3.99 g, 93%) as a golden oil. The Cbz-protected aminoalcohol was of sufficient purity to carry on without further purification.

Step 3: Preparation of N-Hydroxy-N-2-[N",benzyloxycarbonyl-((3-phenoxyphenyl)methyl)amino] ethyl urea The title compound was obtained following the procedures described in Example 2, but employing N-benzyloxycarbonyl-N-((3-phenoxyphenyl)methyl)-2-aminoethanol (prepared as described above) in lieu of the amide alcohol. m.p. 91.5°–93° C.; $^1$H NMR (300 MHz, D$_6$-DMSO; a 1:1 mixture of rotamers were observed for certain protons in the HNMR) 9.28 and 9.33 (1H, s), 6.83–7.42 (9H, m), 6.33 (2H, s),5.05 and 5.12 (2H, br s), 3.30–3.51 (4H, m). Analysis calc'd for C$_{24}$H$_{25}$N$_3$O$_5$: C, 66.20; H, 5.79; N, 9.65; Found: C, 66.16; H, 5.86; N, 9.89.

EXAMPLE 161

Preparation of N-Hydroxy-N-2-[(3-phenoxyphenyl)methyl)amino]ethyl urea

The title compound was obtained by exposing N-Hydroxy-N-2-[N"-benzyloxycarbonyl-(( 3-phenoxyphenyl) methyl)amino]ethyl urea (1.26 g, 2.89 mmol) to 10% Pd/C (1.26 g) in absolute ehtanol (12 mL) and dioxane/HCL (10 mL, 4.8M HCl) under 1 atm of hydrogen. The reaction was judged to be complete after 0.5 h. After purging with nitrogen, the reaction was filtered through celite and the filter cake washed (3×, 15 mL 1:1 absolute ethanol:4.8M dioxane HCl). The combined filtrates were concentrated under vacuum and the resulting residue partitioned between ethyl acetate and 10% aqueous sodium hydroxide. The combined organic layers were washed (3×, brine), dried over NaSO$_4$, and concentrated under vacuum to provide a light brown waxy solid. Recrystallization from ethyl acetate and hexanes provided the title compound (160 mg, 18%) as a colorless solid m.p. 105°–107° C.; $^1$H NMR (300 MHz, D$_6$-DMSO; a 1:1 mixture of rotamers were observed for certain protons in the HNMR) ca. 9.3 (1H, br s), 7.38 (2H, dd, J=9,7 Hz), 7.32 (1H, d, J=7 Hz), 7.13 (1H, q, J=7 Hz), 6.97– 7.05 (3H, m), 6.86 (1H, dd, J=7,2 Hz), 6.28 (2H, s), 3.40 (2H, t, J=6.5 Hz), 3.32 (2H, br s), 2.67 (2H, t, J=6.5 Hz); MS (M+H)$^+$=302. Analysis calc'd for C$_{16}$H$_{19}$N$_3$O$_3$: C, 63.77; H, 6.35; N, 13.94; Found: C, 63.51; H, 6.60; N, 13.99.

EXAMPLE 162

Preparation of
N-Hydroxy-N-2-[(3-(3-(4-chlorophenoxy)phenyl)-transpropenoyl)amino] ethyl urea Step 1: Preparation of 3-((4-chlorophenoxy)phenyl)propenoate.

To a solution of 3-(4-chlorophenoxy)benzaldehyde (23.3 g, 0.10 mol) in dry pyridine (100 mL) was added malonic acid (52.0 g, 0.50 mol) and morpholine (1.5 mL). The resulting solution was heated at 60° C. for 8 h, then stirred at ambient temperature for 48 h. The reaction was poured into cold 1% aqueous HCl solution and stirred vigorously for 1.5 h. The resulting colorless solid was collected by filtration and washed with water. After drying, the solid was recrystallized from 95% ethanol to provide the acid (23.1 g, 84%) after drying under vacuum.

Step 2: Preparation of N-Hydroxy-N-2-[(3-(3-(4-chlorophenoxy)phenyl) propenoyl)amino]ethyl urea The title compound was prepared by following the procedures in example 51 but employing 3-((4-chlorophenoxy)phenyl) propenoate in lieu of 2-phenoxybenzoate. m.p. 160°–162° C.; $^1$H NMR (300 MHz, D$_6$-DMSO) 9.31 (1H, s), 8.09 (1H, t, J=6 Hz), 7.35–7.47 (5H, m), 7.22 (1H, br s), 7.02–7.09 (4H, m), 6.58 (1H, d, J=15.5 Hz), 6.53 (2H, s), 3.53 (2H, t, J=6.5 Hz), ca. 3.32 (2H, m); MS (M+H)$^+$=302. Analysis calc'd for C$_{18}$H$_{18}$N$_3$O$_4$Cl: C, 57.53; H, 4.83; N, 11.18; Found: C, 57.33; H, 4.60; N, 11.01.

EXAMPLE 163

Preparation of
N-Hydroxy-N-2-[(3-(3-butyloxyphenyl)-trans-propenoyl)amino] ethyl urea The title compound was prepared by following the procedures in example 51 but employing 3-(3-butyloxyphenyl)propenoate in lieu of 2-phenoxybenzoate. The starting acid, 3-(3-butyloxyphenyl)propenoate, was prepared from 3-hydroxybenzaldehyde by conversion to 3-butyloxybenzaldehyde by the procedure described in example 19. The 3-butyloxybenzaldehyde was converted to the corresponding propenoate following the method described in step 1 of Example 162. The title compound was obtained as a colorless solid after chromatographic purification over silica gel using ethyl acetate as the eluant. m.p. 159°–160° C.; $^1$H NMR (300 MHz, D$_6$-DMSO) 9.32 (1H, s), 8.10 (1H, t, J=6 Hz), 7.49 (1H, d, J=15.5 Hz), 7.31 (1H, t, J=8 Hz), 7.10–7.14 (2H, m), 6.93 (1H, dt, J=9,1,1 Hz), 6.63 (1H, d, J=15.5 Hz), 6.33 (2H, s), 3.99 (2H, t, J=6.5 Hz), 3.43 (2H, m), ca. 3.36 (2H, m), 1.71 (2H, pentet, J=7 Hz), 1.44 (2H, sextet, J=7 Hz), 0.93 (3H, t, J=7 Hz); MS (M+H)$^+$=322, (M+NH$_4$)$^+$= 339. Analysis calc'd for C$_{16}$H$_{23}$N$_3$O$_4$: C, 59.80; H, 7.21; N, 13.08; Found: C, 59.70; H, 7.10; N, 13.00.

EXAMPLE 164

Preparation of
N-Hydroxy-N-2-[(3-(4-chlorophenoxy)phenyl),3-methyl-trans-propenoyl)amino] ethyl urea Step 1. Preparation of 3-(4-chlorophenoxy)phenyl)-3-methyl-trans-propenoate.

3-(4-chlorophenoxy)benzaldehyde was convened to the corresponding acetophenone derivative (addition of methylmagnesium bromide then oxidation to the ketone with Jones reagent). The ketone (2.46 g, 10.0 mmol) was treated with bis(2,2,2-trifluoroethyl)(methoxycarbonylmethyl) phosphonate (3.56 g, 11.2 mmol), lithium bromide (1.13 g, 13.0 mmol), and triethylamine (1.8 mL. 13.0 mmol) in dry THF (Synth. Commun. 1990, 20(6), 869) to provide the methyl ester of the title compound as a mixture of isomers. The pure trans-isomer was obtained by chromatography over silica gel (100 g) using 5% ethyl acetate:hexanes and then 10% ethyl acetate:hexanes as the eluant. Conversion of the methyl ester (687 mg, 2.27 mmol) to the corresponding acid was achieved by hydroysis in ethanolic (20 mL) aqueous lithium hydroxide (4 mL of a 1M aqueous solution).

Step 1. Preparation of N-Hydroxy-N-2-[(3-(4-chlorophenoxy)phenyl)- 3-methyl-trans-propenoyl)amino] ethyl urea.

The title compound was prepared by following the procedures in example 51 but employing 3-(4-chlorophenoxy)phenyl)-3-methyl-trans-propenoate in lieu of 2-phenoxybenzoate. The title compound was obtained as a yellow oil after chromatographic purification over silica gel using ethyl acetate as the eluant. $^1$H NMR (300 MHz, D$_6$-DMSO) 9.31 (1H, s), 8.03 (1H, t, J=6 Hz), 7.40–7.47 (3H, m), 7.31 (1H, br d, J=5.5 Hz), 7.18 (1H, t, J= 1,5 Hz), 7.00–7.05 (3H, m), 6.32 (2H, s), 6.21 (1H, d, J=1.5 Hz), 3.27–3.43 (4H, m), 2.45 (3H, d, J=1.5 Hz); MS (M+H)$^+$=390, (M+H)$^+$=407. Analysis calc'd for C$_{19}$H$_{20}$N$_3$O$_4$Cl: C, 58.54; H, 5.17; N, 10.78; Found: C, 58.30; H, 5.10; N, 10.05.

EXAMPLE 165

Preparation of
N-Hydroxy-N-2-[(3-(4-bromophenyl)-2-methyl-trans-propenoyl)amino] ethyl urea Step 1. Preparation of 3-(4-bromophenyl)-2-methyl-trans-propenoate.

To a magnetically stirred solution of 4-bromobenzaldehyde (10.2 g, 55.1 mmol) in dry THF (125 mL) was added (carboethoxyethylidene)triphenylphosphorane (21.0 g, 57.9 mmol) in small portions. The reaction was stirred for 18 h at ambient temperature under a nitrogen atmosphere. The reaction was concentrated under vacuum and triturated with hexanes; the precipitated triphenylphosphine oxide was removed by filtration. The filtrate was concentrated under vacuum and the resulting slurry purified by chromatography over silica gel (100 g) using 10% ethyl acetate:hexanes as the eluant to provide the ethyl ester of the desired trans-propenoate (17.6 g, 86%). Hydrolysis of the ester (17.6 g, 47.6 mmol) was achieved by exposure to aqueous lithium hydroxide (200 mL of a 1M solution, 200 mmol) in 95% ethanol (200 mL) for 5 hours. The reaction solution was filtered and the filtrate acidified to pH<2 with aqueous 6N HCl to precipitate the acid as a white solid. The acid was collected by filtration, washed with water, and vacuum dried to provide the title compound (11.5 g, 99%).

Step 2. Preparation of N-Hydroxy-N-2-[(3-(4-chlorophenoxy)phenyl)-3-methyl-trans-propenoyl)amino] ethyl urea.

The title compound was prepared by following the procedures in example 51 but employing 3-(4-bromophenyl)-2-methyl-trans-propenoate in lieu of 2-phenoxybenzoate. The title compound was obtained as a colorless solid after chromatograaphic purification and recrystallization from ethyl acetate/hexanes. mp 172.5–174° C.; $^1$H NMR (300 MHz, D$_6$-DMSO) 9.31 (1H, s), 8.03 (1H, t, J=6 Hz), 7.60 (2H, d, J=8 Hz), 7.34 (2H, d, J=8 Hz), 7.16 (1H,br s), 6.32 (2H, s), 3.3–3.50 (4H, m), 1.98 (3H, d, J=1.5 Hz); MS (M+H)$^+$=342, (M+NH$_4$)$^+$=359. Analysis calc'd for C$_{13}$H$_{16}$N$_3$O$_3$Br: C, 45.63 H, 4.71; N, 12.28; Found: C, 45.40; H, 4.55; N, 12.12.

EXAMPLE 166

Preparation of
N-Hydroxy-N-2-[(3-(4-chlorophenoxy)phenyl)-2-methyl-trans-propenoyl)amino] ethyl urea The title compound was prepared by following the procedures in Example 165 but employing 3-(4-chlorophenoxy)phenyl)-3-methyl-trans-propenoate in lieu of 3-(4-bromophenyl)- 2-methyl-trans-propenoate. The title compound was obtained as a yellow solid after chromatographic purification over silica gel using 50% ethyl acetate:hexanes as the eluant. $^1$H NMR (300 MHz, D$_6$-DMSO) 9.30 (1H, s), 8.01 (1H, t, J=5.5 Hz), 7.44 (2H, d, J=9 Hz), 7.43 (1H, m), 7.18 (1H, d, J=8 Hz), 7.05 (2H, d, J=9 Hz), 7.00 (2H, m), 6.54 (1H, m), 5.40 (2H, s), 3.55 (2H, m), 3.27–3.34 (2H, m), 1.95 (3H, d, J=1.0 Hz). Analysis calc'd for C$_{12}$H$_{20}$N$_3$O$_4$Cl: C, 47.14; H, 6.59; N, 13.74; Found: C, 46.90; H, 6.40; N, 13.52.

EXAMPLE 167

Preparation of
N-Hydroxy-N-2-[(2-(3-(4-ethyloxyphenoxy)phenyl)-trans-cyclopropyl)carbonyl amino]ethyl urea The title compound was prepared by following the procedures in example 2 but employing 2-(3-(4-ethyloxyphenoxy)phenyl)-trans-cyclopropyl)carboxylic acid (prepared by oxidation of the corresponding aldehyde prepared as described in Brooks, D. W.; Rodriques, K. E. U.S. Pat. No. 5,037,853) in lieu of 3-phenoxybenzoate. The title compound was obtained as a colorless solid after recrystallization from ethyl acetate and methanol. mp 173–175° C. (with decomposition); $^1$H NMR (300 MHz, D$_6$-DMSO) 9.27 (1H, s), 8.14 (1H, t, J=7 Hz), 7.22 (1H, t, J=8 Hz), 6.95 (4H, m), 6.82 (1H, d, J=8 Hz), 6.72 (1H, s), 6.67 (1H, dd, J=8,1.5 Hz), 6.31 (1H, br s), 4.00 (2H, q, J=8 Hz), 3.32–3.40 (2H, m), 3.20–3.30 (2H, m), 2.17–2.50 (1H, m), 1.83 (1H, dt, J=8.5, 5,5 Hz), 1.32 (3H,t, J=7.5 Hz), 1.12– 1.2 (1H, m); MS (M+H)$^+$=400. Analysis calc'd for C$_{21}$H$_{25}$N$_3$O$_5$(0.25 H$_2$O): C, 62.44; H, 6.36; N, 10.40; Found: C, 62.52; H, 6.39; N, 10.36.

EXAMPLE 168

Preparation of
N-Hydroxy-N-[N"-(3-phenoxybenzoyl)-aminomethyl]urea

Step 1: Preparation of N-(3-phenoxybenzoyl)aminomethanol

A flask was charged with 3-phenoxybenzoylamide (2.07 g, 9.8 mmol)(prepared from the corresponding acid chloride and concentrated ammonia), potassium carbonate (1.3 mL, 4% aqueous solution, 3.8 mmol), and aqueous formaldehyde (1.1 mL, 37% aqueous solution, 13.6 mmol). The resulting suspension was heated to reflux to give a two-phased solution. Addition of more aqueous formaldehyde (3 mL, 37 mmol) gave a homogeneous solution which was heated at reflux for 4 h. The reaction solution was cooled and partitioned between brine and ethyl acetate. The aqueous layer was dram off and extracted with ethyl acetate (2×). The combined organic layers were washed (2×, brine), dried (Na$_2$SO$_4$), and concentrated under vacuum to provide 2.47 gms of a viscous oil which solidified after vacuum drying. Recrystallization from cold ethyl acetate:hexanes provided the title compound as a colorless solid (1.38 g, 58%), mp 112.5–113° C.

Step 2. Preparation of N-Hydroxy-N-[N"-(3-phenoxybenzoyl)aminomethyl]urea.

To an ice-cooled solution of N-((3-phenoxy)benzoyl)aminomethanol (0.50 g, 2.06 mmol), N,O-diphenoxycarbonylhydroxylamine (0.62 g, 2.26 mmol), and triphenylphosphine (0.59 g, 2.26 mmol) in dry THF (5 mL) was added diethylazodicarboxylate (356 µL, 2.26 mmol) in dry (THF). After the addition was complete the cooling bath was removed and the reaction stirred at ambient temperature for 1 h. The volatiles were removed under vacuum and the resulting slurry was dissoved in 15 mL of dichloromethane and concentrated under vacuum (2 cycles) and purified by chromatography (silica gel, 20% ethyl acetate/hexanes, column packed with hexanes) to provide the corresponding mitsunobu product as an oil. (0.64 g, 62%). The mitsunobu product (0.60 g, 1.2 mmol) was exposed to concentrated ammonoim hydroxide (3 mL) in dioxane (1 mL) and methanol (1 mL) for 4 h and concentrated under vacuum. The resulting slurry was purified by chromatography (silica gel, packed in dichlormethane, eluted with 5% methanol:chloroform) to provide the title compound and minor contaminants. Recrystallization from ethyl actate:methanol provided the pure title compound as a colorless solid. m.p. 151°–154° C. (softening at ~120° C.); $^1$H NMR (300 MHz, D$_6$-DMSO; the HNMR was a mixture of two rotamers which were evident in some of the absorptions) 9.37 (1H, s), 9.04 and 8.87 (1H, t, J=6 Hz), 7.65–7.70 (1H, m), 7.39–7.53 (4H, m), 7.15–7.21 (2H, m), 7.03 (2H, dq, J=8.5,1,1,1 Hz), 6.67 and 6.38 (2H, s), 5.03 and 4.91 (2H, d, J=6 Hz); MS (M+H)$^+$= 302, (M+NH$_4$)$^+$=319. Analysis calc'd for C$_{15}$H$_{15}$N$_3$O$_4$(0.30 H$_2$O): C, 58.75; H, 5.13; N, 13.70; Found: C, 58.52; H, 4.89; N, 14.40.

EXAMPLE 169

Preparation of
(S)-N-Hydroxy-N-[2-((2-(3-phenoxyphenyloxy)-acetyl)amino)propyl]urea Step 1: Preparation of 2-(3-phenoxyphenyloxy)acetate.

To a flask charged with reagent grade acetone (400 mL) was added 3-phenoxyphenol (10.0 g, 52.6 mmol), potassium carbonate (7.6 g, 55 mmol), and ethyl bromoacetate (6.1 mL, 53.7 mmol). The resulting mixture was stirred at ambient temperature for 20 h, concentrated under vacuum to ~50 mL, and partitioned between ethyl acetate and water. After separating the two layers the aqueous solution was extracted with ethyl acetate (2×). The combined organic layers were washed (2×, brine), dried (MgSO$_4$), and concentrated under vacuum to provide the ethyl ester of the title compound (14.35 g, 100%). The ester was hydrolyzed without further purification by exposure to excess aqueous lithium hydroxide (200 mL, 1M LiOH), in ethanol (200 mL) for 4 h at ambient temperature. The reaction solution was acidified with excess aqueous 2N HCL, and extracted with ethyl acetate (2×). The combined organic layers were concentrated under vacuum and the resulting gummy liquid azeotroped with toluene (2×) to remove water. The resulting viscous green oil was recrystallized from ether:pentane at −20° C. to provide the title acid as a coilorless solid.

Step 2: Preparation of (S)-N-Hydroxy-N-[2-((2-(3-phenoxyphenyloxy)acetyl)amino)ethyl]urea.

The title compound was prepared as described in example 51 but employing 2-(3-phenoxyphenyloxy)acetate and (S)-N-hydroxy-N-[2-((tert-butoxycarbonyl)amino)propyl] urea in lieu of 2-phenoxybezoic acid and N-hydroxy-N-[2-((tert-butoxycarbonyl) amino)ethyl]urea. Chromatographic purification (silica gel, 4% methanol/ether/hexanes) and recrystallization from ether/methanol at −20° C. provided the title compound as a colorless solid (0.31 g, 25%). m.p. 137°–138° C.; $^1$H NMR (300 MHz, D$_6$-DMSO) 9.32 (1H, s), 7.98 (1H, d, J=8 Hz), 7.40 (2H, dd, J=9,8 Hz), 7.28 (1H, t, J=8.5 Hz), 7.14 (1H, t, J=8.5 Hz), 7.03 (2H, d, J=9 Hz), 6.73 (1H, dd, J=9,2 Hz), 6.57–6.63 (2H, m), 6.30 (2H, s), 4.42 (2H, s), 4.12 (1H, septet, J=6.5 Hz), 3.25–3.48 (4H, m), 1.04 (3H, d, J=6.5 Hz); MS (M+H)$^+$=360. Analysis calc'd for C$_{18}$H$_{21}$N$_3$OS: C, 60.16; H, 5.89; N, 11.69; Found: C, 60.02; H, 5.97; N, 11.42.

EXAMPLE 170

Preparation of
N-Hydroxy-N-[2-((2-(3-phenoxyphenyloxy)-propionyl)amino)ethyl] urea Step 1: Preparation of 2-(3-phenoxyphenyloxy)propionate The title compound was prepared as described in Example 169 but employing methyl 2-bromopropionate in lieu of ethyl bromoacetate to provide the title compound as a colorless solid (mp 70°–73.5° C.).

Step 2: Preparation of N-Hydroxy-N-[2-((2-(3-phenoxyphenyloxy)propionyl)amino)ethyl]urea.

The title compound was prepared as described in example 51 but employing 2-(3-phenoxyphenyloxy)propionate in lieu of 2-phenoxybezoic acid. Chromatographic purification (silica gel, 4% methanol/dichloromethane) and recrystallization from ether/ethyl acetate at −20° C. provided the title compound as a colorless solid (0.61 g, 22%). m.p. 112°–113° C.; $^1$H NMR (300 MHz, D$_6$-DMSO) 9.27 (1H, s), 8.07 (1H, d, J=8 Hz), 7.39 (2H, dd, J=9,8 Hz), 7.28 (1H, t, J=8.5 Hz), 7.14 (1H, t, J=8.5 Hz), 7.02 (2H, d, J=9 Hz), 6.68 (1H, dd, J=9,2 Hz), 6.53–6.60 (2H, m), 6.31 (2H, s), 4.66 (1H, q, J=6.5 Hz), 3.18–3.48 (4H, m), 1.39 (3H, d, J=6.5 Hz); MS (M+H)$^+$=360, (M+NH$_4$)$^+$=388. Analysis calc'd for C$_{18}$H$_{21}$N$_3$O$_5$: C, 60.16; H, 5.89; N, 11.69; Found: C, 60.06; H, 5.88; N, 11.68.

EXAMPLE 171

Preparation of
(d,l)-N-Hydroxy-N-[3-(2-(3-(4-chlorophenoxy)-phenyl)acetylamino)prop- 2-yl]urea Step 1: Preparation of (3-(4-chlorophenoxy)phenyl)methylcyanide To an ice-cooled flask charged with dichloromethane (50 mL) and 3-(4-chlorophenoxy)benzyl alcohol (2.97 g, 12.7 mmol) was added phosphorous tribromide (15 mL, 1M solution in dichloromethane, 15 mmlo). The resulting solution was stirred at ambient temperature for 17 h and crushed ice added, and the two-phased mixture was extracted with ether (3×, 100 mL) The combined organic layers were washed (2×, brine), dried (MgSO$_4$), and concentrated under vacuum to provide the unpurified benzyl bromide which was carried on without further purification. The benzyl bromide and sodium cyanide (1.0 g, 20.4 mmol) were dissolved in DMSO and stirred at ambient temperature for 1 h. The reaction mixture was partitioned between brine and ethyl acetate and the aqueous layer was extracted again (2×, ethyl acetate). The combined organic layers were dried (MgSO$_4$) and concentrated under vacuum. The resulting oil was purified by chromatography (silica gel, 20% ethyl acetate/hexanes) to give the pure cyano derivative (1.12 g, 36%).

Step 2: Preparation of 2-(3-(4-chlorophenoxy)phenyl)acetate

The cyanide (2.0 g, 8.21 mmol) prepared in step 1 was hydrolyzed to the corresponding acid according to the procedure of Adams (Org. Synth., Coll Vol. I., Gilman, H.; Blatt, A. H.: eds.; John Wiley & Sons; New York, 1976; p 436) by refluxing with water, sulfuric acid, and acetic acid. Recrystallization of the unpurified acid from ether provided the title compound as light tan crystals (1.05 g, 49%).

Step 3: Preparation of (d,l)-N-Hydroxy-N-[3-(2-(3-(4-chlorophenoxy)phenyl)acetylamino)prop- 2-yl]urea The title compound was prepared as described in example 51 but employing 2-(3-(4-chlorophenoxy)phenyl)acetate and (d,l)-N-Hydroxy-N-[3-((tert-butyoxycarbonyl) amino)prop-2-yl]urea in lieu of 2-phenoxybezoic acid and N-hydroxy-N-[ 2-((tert-butoxycarbonyl) amino)ethyl]urea. Recrystallization from ethyl acetate/hexanes provided the title compound as a colorless solid (0.12 g, 35%). m.p. 161°–162.5° C.; $^1$H NMR (300 MHz, D$_6$-DMSO) 9.32 (1H, s), 8.03 (1H, d, J=8 Hz), 7.43 (2H, dt, J=9,1.5 Hz), 7.23 (1H, t, J=8.5 Hz), 7.00–7.09 (3H, m), 6.94 (1H, br s), 6.89 (1H, dd, J=9,2 Hz), 6.29 (2H, s), 4.12 (1H, septet, J=6.5 Hz), 3.42 (2H, s), 3.00–3.18 (2H, m), 0.90 (3H, d, J=6.5 Hz); MS (M+H)$^+$=378/380. Analysis calc'd for C$_{18}$H$_{20}$N$_3$O$_4$Cl(0.5 H$_2$O): C, 55.96; H, 5.14; N, 10.70; Found: C, 55.89; H, 5.47; N, 10.86.

EXAMPLE 172

Preparation of
N-Hydroxy-N-[3-((3-(3-(4-chlorophenoxy)phenyl)-propionyl)amino)prop- 2-yl]urea Following the procedure outlined in example 51 but employing 3-(3-(4-chlorophenoxy)phenyl)propionyl chloride (prepared by reduction of 3-(3-(4-chlorophenoxy)phenyl)propenoic acid over 5% Pt/C in ethyl acetate at 4 atm of hydrogen and subsequent conversion to the acid chloride with oxalyl chloride) and (d,l)-N-Hydroxy-N-[3-((ten-butyoxycarbonyl)amino)prop-2-yl]urea in lieu of 2-phenoxybenzoyl chloride and N-hydroxy-N-[2-((tert-butoxycarbonyl) amino)ethyl]urea provided the title compound as a colorless solid after recrystallization from methanol. m.p. 161°–163° C.; $^1$H NMR (300 MHz, D$_6$-DMSO) 8.79 (1H, s), 7.88 (1H, t, J=5.5,5.5 Hz), 7.43 (2H, d, J=8.5 Hz), 7.29 (1H, d, J=8.5 Hz), 7.02 (2H, d, J=8.5 Hz), 6.88 (1H, br s), 6.84 (1H, d,d, J=8.5,2 Hz), 6.28 (2H, s), 4.08 (1H, septet, J=7 Hz), 3.03–3.10 (2H, m), 2.80 (2H, t, J=7.5 Hz), 2.38 (2H, t, J=7.5 Hz), 0.89 (3H, d, J=7 Hz),; MS (M+H)$^+$ =392. Analysis calc'd for C$_{19}$H$_{22}$N$_3$O$_4$Cl(0.75 H$_2$O): C, 57.58; H, 5.72; N, 10.00; Found: C, 57.43; H, 5.46; N, 10.22.

EXAMPLE 173

Preparation of N-Hydroxy-N-5-[(3-phenoxybenzoyl)amino]-pent-3-yn-2-yl urea

Step 1: Preparation of (3-phenoxybenzoyl)amino-2-propyne.

To a dichloromethane (25 mL) solution of amino-2-propyne (0.96 g, 17.43 mmol) and triethylamine (3.33 mL, 23.7 mmol) at 0° C. was added 3-phenoxybenzoyl chloride (3.68 g, 15.8 mmol) in dichloromethane (25 mL) in a dropwise fashion. The reaction was stirred for 1 h after removing the cooling bath and partitioned between dichloromethane and 10% aqueous HCl. The layers were separated and the aqueous layer was extracted with dichloromethane (2×). The combined organic layers were washed (1×, saturated sodium bicarbonate; 1×, brine), dried (MgSO$_4$), and concentrated under vacuum to give a golden oil. Recrystallization with ehter ethyl acetate provided the title compound as a colorless solid (2.95 g, 74%).

Step 2: Preparation of 5-(3-phenoxybenzoyl)amino-3-propyn-2-ol

A solution of (3-phenoxy benzoyl)amino-2-propyne (2.54 g, 10.1 mmol) in dry THF (30 mL) was cooled to −78° C. and n-butyl lithium (8.9 mL, 2.5M solution in hexanes, 22.4 mmol) added via syringe. Acetaldehyde was added via syringe in a single portion to the red reaction solution. After stirring for 10 min at −78° C., the reaction was quenched by adding excess saturated ammonium chloride and partitioned between water and ethyl acetate. The aqueous layer was extracted a second time and the combined organic layers were washed (1×, saturated sodium bicarbonate; 1×, brine), dried (MgSO$_4$), and concentrated under vacuum to provide a light yellow oil. Purification by chromatography (silica gel, 30% ethyl acetate/hexanes) to provide the title compound as a colorless oil (1.05 g, 35%).

Step 3: Preparation of N-Hydroxy-N-5-[(3-phenoxybenzoyl)amino]-pent-3,yn-2-yl urea.

The title compound was prepared as described for the conversion of N-Boc- 1-amino-2-propanol to (d,l)-N-Hydroxy-N-[3-((tert-butyoxycarbonyl)amino)prop- 2-yl]urea using 5-(3-phenoxybenzoyl)amino-3-propyn-2-ol in lieu of N-Boc-1-amino- 2-propanol. The purified product was obtained after chromatography (silica gel, 3% methanol/dichloromethane) as a colorless foam. m.p. 63°–85° C. (shrinking and melting observed over the entire range); $^1$H NMR (300 MHz, D$_6$-DMSO) 9.23 (1H, s),8.67 (1H, t, J=6 Hz), 7.20–7.32 (4H, m), 7.16 (1H, d, J=4.5 Hz), 6.47 (2H, s), 5.82 (1H, d, J=4.5 Hz), 4.91 (1H, br q, J=7 Hz), 3.98 (2H, dd, J=6,1.5 Hz), 1.24 (3H, d, J=7 Hz); MS (M+H)$^+$= 362, (M+NH$_4$)$^+$=379.

The substituted amide-linked N-hydroxyurea compounds of Examples 174– 253 as shown in Table 45 are prepared by the method used for Example 2 substituting m-phenoxybenzoic acid with the requisite substituted mercaptobenzoic acid derivative which can be prepared by alkylation of the corresponding mercaptobenzoate according to the procedure described in example 23 for the alkylation of 3-hydroxybenzoate.

TABLE 5

Novel Substituted Mercaptobenzoate Amide-linked N-Hydroxyureas

| Example | n | R$_1$ |
|---|---|---|
| 174 | 0 | —(CH$_2$)$_2$CH$_3$ |
| 175 | 2 | —(CH$_2$)$_2$CH$_3$ |
| 176 | 0 | —(CH$_2$)$_3$CH$_3$ |
| 177 | 2 | —(CH$_2$)$_3$CH$_3$ |
| 178 | 0 | —(CH$_2$)$_4$CH$_3$ |
| 179 | 2 | —(CH$_2$)$_4$CH$_3$ |
| 180 | 0 | —(CH$_2$)$_5$CH$_3$ |
| 181 | 2 | —(CH$_2$)$_5$CH$_3$ |
| 182 | 0 | —CH$_2$CH(CH$_3$)$_2$ |
| 183 | 2 | —CH$_2$CH(CH$_3$)$_2$ |
| 184 | 0 | —(CH$_2$)$_2$CH(CH$_3$)$_2$ |
| 185 | 2 | —(CH$_2$)$_2$CH(CH$_3$)$_2$ |
| 186 | 0 | —(CH$_2$)$_3$CH(CH$_3$)$_2$ |
| 187 | 2 | —(CH$_2$)$_3$CH(CH$_3$)$_2$ |
| 188 | 0 | —(CH$_2$)$_4$CH(CH$_3$)$_2$ |
| 189 | 2 | —(CH$_2$)$_4$CH(CH$_3$)$_2$ |
| 190 | 0 | —CH$_2$CH=CH$_2$ |
| 191 | 2 | —CH$_2$CH=CH$_2$ |
| 192 | 0 | -trans-CH$_2$CH=CHCH$_3$ |
| 193 | 2 | -trans-CH$_2$CH=CHCH$_3$ |
| 194 | 0 | -trans-CH$_2$C(CH$_3$)=CHCH$_3$ |
| 195 | 2 | -trans-CH$_2$C(CH$_3$)=CHCH$_3$ |
| 196 | 0 | —CH$_2$CH=C(CH$_3$)CH$_3$ |
| 197 | 2 | —CH$_2$CH=C(CH$_3$)CH$_3$ |
| 198 | 0 | —CH$_2$CH$_2$N(CH$_3$)$_2$ |
| 199 | 2 | —CH$_2$CH$_2$N(CH$_3$)$_2$ |
| 200 | 0 | —CH$_2$CH$_2$N(CH$_2$CH$_3$)$_2$ |
| 201 | 2 | —CH$_2$CH$_2$N(CH$_2$CH$_3$)$_2$ |
| 202 | 0 | —(CH$_2$)$_2$CH$_2$N(CH$_3$)$_2$ |
| 203 | 2 | —(CH$_2$)$_2$CH$_2$N(CH$_3$)$_2$ |
| 204 | 0 | —(CH$_2$)$_2$CH$_2$N(CH$_2$CH$_3$)$_2$ |
| 205 | 2 | —(CH$_2$)$_2$CH$_2$N(CH$_2$CH$_3$)$_2$ |
| 206 | 0 | —CH$_2$-2-pyridyl |
| 207 | 2 | —CH$_2$-2-pyridyl |
| 208 | 0 | —CH$_2$-3-pyridyl |
| 209 | 2 | —CH$_2$-3-pyridyl |
| 210 | 0 | —CH$_2$-4-pyridyl |
| 211 | 2 | —CH$_2$-4-pyridyl |
| 212 | 0 | —CH$_2$-2-furyl |
| 213 | 2 | —CH$_2$-2-furyl |
| 214 | 0 | —CH$_2$-3-furyl |
| 215 | 2 | —CH$_2$-3-furyl |
| 216 | 0 | —CH$_2$-2-thienyl |
| 217 | 2 | —CH$_2$-2-thienyl |
| 218 | 0 | —CH$_2$-3-thienyl |
| 219 | 2 | —CH$_2$-3-thienyl |
| 220 | 0 | —CH$_2$-2-benzo[b]thienyl |
| 221 | 2 | —CH$_2$-2-benzo[b]thienyl |
| 222 | 0 | —CH$_2$-2-benzo[b]furyl |
| 223 | 2 | —CH$_2$-2-benzo[b]furyl |
| 224 | 0 | —CH$_2$-2-thiazoyl |
| 225 | 2 | —CH$_2$-2-thiazoyl |
| 226 | 0 | —CH$_2$-2-imidazoyl |
| 227 | 2 | —CH$_2$-2-imidazoyl |
| 228 | 0 | —CH(CH$_3$)-2-pyrimidyl |
| 229 | 2 | —CH(CH$_3$)-2-pyrimidyl |
| 230 | 0 | —CH(CH$_3$)-2-pyridyl |
| 231 | 2 | —CH(CH$_3$)-2-pyridyl |
| 232 | 0 | —CH(CH$_3$)-3-pyridyl |
| 233 | 2 | —CH(CH$_3$)-3-pyridyl |
| 234 | 0 | —CH(CH$_3$)-4-pyridyl |
| 235 | 2 | —CH(CH$_3$)-4-pyridyl |

TABLE 5-continued

Novel Substituted Mercaptobenzoate Amide-linked N-Hydroxyureas $R^1SO_n$—[benzene ring]—C(=O)—N(H)—CH$_2$CH$_2$—N(OH)—C(=O)—NH$_2$

| Example | n | R$_1$ |
|---|---|---|
| 236 | 0 | —CH(CH$_3$)$_2$-2-furyl |
| 237 | 2 | —CH(CH$_3$)$_2$-2-furyl |
| 238 | 0 | —CH(CH$_3$)-3-furyl |
| 239 | 2 | —CH(CH$_3$)-3-furyl |
| 240 | 0 | —CH(CH$_3$)-2-thienyl |
| 241 | 2 | —CH(CH$_3$)-2-thienyl |
| 242 | 0 | —CH(CH$_3$)-3-thienyl |
| 243 | 2 | —CH(CH$_3$)-3-thienyl |
| 244 | 0 | —CH(CH$_3$)-2-benzo[b]thienyl |
| 245 | 2 | —CH(CH$_3$)-2-benzo[b]thienyl |
| 246 | 0 | —CH(CH$_3$)$_2$-2-benzo[b]furyl |
| 247 | 2 | —CH(CH$_3$)$_2$-2-benzo[b]furyl |
| 248 | 0 | —CH(CH$_3$)-2-thiazoyl |
| 249 | 2 | —CH(CH$_3$)-2-thiazoyl |
| 250 | 0 | —CH(CH$_3$)-2-imidazoyl |
| 251 | 2 | —CH(CH$_3$)-2-imidazoyl |
| 252 | 0 | —CH(CH$_3$)-2-pyrimidyl |
| 253 | 2 | —CH(CH$_3$)-2-pyrimidyl |

The substituted amide-linked N-hydroxyurea compounds of Examples 254– 293 as shown in Table 6 are prepared by the method used for Example 2 substituting m-phenoxybenzoic acid with the requisite substituted aminobenzoic acid derivative which can be prepared by routine alkylative methodology for anilines.

TABLE 6

Substituted Aminobenzoate Amide-linked N-Hydroxyureas

R$^1$(H$_3$C)N—[benzene ring]—C(=O)—N(H)—CH$_2$CH$_2$—N(OH)—C(=O)—NH$_2$

| Example | R1 |
|---|---|
| 254 | —(CH$_2$)$_2$CH$_3$ |
| 255 | —(CH$_2$)$_3$CH$_3$ |
| 256 | —(CH$_2$)$_4$CH$_3$ |
| 257 | —(CH$_2$)$_5$CH$_3$ |
| 258 | —CH$_2$CH(CH$_3$)$_2$ |
| 259 | —(CH$_2$)$_2$CH(CH$_3$)$_2$ |
| 260 | —(CH$_2$)$_3$CH(CH$_3$)$_2$ |
| 261 | —(CH$_2$)$_4$CH(CH$_3$)$_2$ |
| 262 | —CH$_2$CH=CH$_2$ |
| 263 | -trans-CH$_2$CH=CHCH$_3$ |
| 264 | -trans-CH$_2$C(CH$_3$)=CHCH$_3$ |
| 265 | —CH$_2$CH=C(CH$_3$)CH$_3$ |
| 266 | —CH$_2$CH$_2$N(CH$_3$)$_2$ |
| 267 | —CH$_2$CH$_2$N(CH$_2$CH$_3$)$_2$ |
| 268 | —(CH$_2$)$_2$CH$_2$N(CH$_3$)$_2$ |
| 269 | —(CH$_2$)$_2$CH$_2$N(CH$_2$CH$_3$)$_2$ |
| 270 | —CH$_2$-2-pyridyl |
| 271 | —CH$_2$-3-pyridyl |
| 272 | —CH$_2$-4-pyridyl |
| 273 | —CH$_2$-2-furyl |
| 274 | —CH$_2$-3-furyl |
| 275 | —CH$_2$-2-thienyl |
| 276 | —CH$_2$-3-thienyl |
| 277 | —CH$_2$-2-benzo[b]thienyl |
| 278 | —CH$_2$-2-benzo[b]furyl |

TABLE 6-continued

Substituted Aminobenzoate Amide-linked N-Hydroxyureas

R$^1$(H$_3$C)N—[benzene ring]—C(=O)—N(H)—CH$_2$CH$_2$—N(OH)—C(=O)—NH$_2$

| Example | R1 |
|---|---|
| 279 | —CH$_2$-2-thiazoyl |
| 280 | —CH$_2$-2-imidazoyl |
| 281 | —CH(CH$_3$)-2-pyrimidyl |
| 282 | —CH(CH$_3$)-2-pyridyl |
| 283 | —CH(CH$_3$)-3-pyridyl |
| 284 | —CH(CH$_3$)-4-pyridyl |
| 285 | —CH(CH$_3$)$_2$-2-furyl |
| 286 | —CH(CH$_3$)-3-furyl |
| 287 | —CH(CH$_3$)-2-thienyl |
| 288 | —CH(CH$_3$)-3-thienyl |
| 289 | —CH(CH$_3$)-2-benzo[b]thienyl |
| 290 | —CH(CH$_3$)$_2$-2-benzo[b]furyl |
| 291 | —CH(CH$_3$)-2-thiazoyl |
| 292 | —CH(CH$_3$)-2-imidazoyl |
| 293 | —CH(CH$_3$)-2-pyrimidyl |

The substituted amide-linked N-hydroxyurea compounds of Examples 294– 373 shown in Table 7 are prepared by the method used for Example 2 substituting m-phenoxybenzoic acid with the requisite substituted furanoic acid derivative which can be prepared according to the substitution procedure outlined in example 40.

TABLE 7

Substituted Hydroxybenzoate Amide-linked N-Hydroxyureas

R$^1$O—[furan/thiophene ring X]—C(=O)—N(H)—CH$_2$CH$_2$—N(OH)—C(=O)—NH$_2$

| Example | X | R$_1$ |
|---|---|---|
| 294 | O | —(CH$_2$)$_2$CH$_3$ |
| 294 | S | —(CH$_2$)$_2$CH$_3$ |
| 296 | O | —(CH$_2$)$_3$CH$_3$ |
| 297 | S | —(CH$_2$)$_3$CH$_3$ |
| 298 | O | —(CH$_2$)$_4$CH$_3$ |
| 299 | S | —(CH$_2$)$_4$CH$_3$ |
| 300 | O | —(CH$_2$)$_5$CH$_3$ |
| 301 | S | —(CH$_2$)$_5$CH$_3$ |
| 302 | O | —CH$_2$CH(CH$_3$)$_2$ |
| 303 | S | —CH$_2$CH(CH$_3$)$_2$ |
| 304 | O | —(CH$_2$)$_2$CH(CH$_3$)$_2$ |
| 305 | S | —(CH$_2$)$_2$CH(CH$_3$)$_2$ |
| 306 | O | —(CH$_2$)$_3$CH(CH$_3$)$_2$ |
| 307 | S | —(CH$_2$)$_3$CH(CH$_3$)$_2$ |
| 308 | O | —(CH$_2$)$_4$CH(CH$_3$)$_2$ |
| 309 | S | —(CH$_2$)$_4$CH(CH$_3$)$_2$ |
| 310 | O | —CH$_2$CH=CH$_2$ |
| 311 | S | —CH$_2$CH=CH$_2$ |
| 312 | O | -trans-CH$_2$CH=CHCH$_3$ |
| 313 | S | -trans-CH$_2$CH=CHCH$_3$ |
| 314 | O | -trans-CH$_2$C(CH$_3$)=CHCH$_3$ |
| 315 | S | -trans-CH$_2$C(CH$_3$)=CHCH$_3$ |
| 316 | O | —CH$_2$CH=C(CH$_3$)CH$_3$ |
| 317 | S | —CH$_2$CH=C(CH$_3$)CH$_3$ |
| 318 | O | —CH$_2$CH$_2$N(CH$_3$)$_2$ |
| 319 | S | —CH$_2$CH$_2$N(CH$_3$)$_2$ |
| 320 | O | —CH$_2$CH$_2$N(CH$_2$CH$_3$)$_2$ |
| 321 | S | —CH$_2$CH$_2$N(CH$_2$CH$_3$)$_2$ |

TABLE 7-continued

Substituted Hydroxybenzoate Amide-linked N-Hydroxyureas

| Example | X | R₁ |
|---|---|---|
| 322 | O | —(CH₂)₂CH₂N(CH₃)₂ |
| 323 | S | —(CH₂)₂CH₂N(CH₃)₂ |
| 324 | O | —(CH₂)₂CH₂N(CH₂CH₃)₂ |
| 325 | S | —(CH₂)₂CH₂N(CH₂CH₃)₂ |
| 326 | O | —CH₂-2-pyridyl |
| 327 | S | —CH₂-2-pyridyl |
| 328 | O | —CH₂-3-pyridyl |
| 329 | S | —CH₂-3-pyridyl |
| 330 | O | —CH₂-4-pyridyl |
| 331 | S | —CH₂-4-pyridyl |
| 332 | O | —CH₂-2-furyl |
| 333 | S | —CH₂-2-furyl |
| 334 | O | —CH₂-3-furyl |
| 335 | S | —CH₂-3-furyl |
| 336 | O | —CH₂-2-thienyl |
| 337 | S | —CH₂-2-thienyl |
| 338 | O | —CH₂-3-thienyl |
| 339 | S | —CH₂-3-thienyl |
| 340 | O | —CH₂-2-benzo[b]thienyl |
| 341 | S | —CH₂-2-benzo[b]thienyl |
| 342 | O | —CH₂-2-benzo[b]furyl |
| 343 | S | —CH₂-2-benzo[b]furyl |
| 344 | O | —CH₂-2-thiazoyl |
| 345 | S | —CH₂-2-thiazoyl |
| 346 | O | —CH₂-2-imidazoyl |
| 347 | S | —CH₂-2-imidazoyl |
| 348 | O | —CH(CH₃)-2-pyrimidyl |
| 349 | S | —CH(CH₃)-2-pyrimidyl |
| 350 | O | —CH(CH₃)-2-pyridyl |
| 351 | S | —CH(CH₃)-2-pyridyl |
| 351 | O | —CH(CH₃)-3-pyridyl |
| 353 | S | —CH(CH₃)-3-pyridyl |
| 354 | O | —CH(CH₃)-4-pyridyl |
| 355 | S | —CH(CH₃)-4-pyridyl |
| 356 | O | —CH(CH₃)₂-2-furyl |
| 357 | S | —CH(CH₃)₂-2-furyl |
| 358 | O | —CH(CH₃)-3-furyl |
| 359 | S | —CH(CH₃)-3-furyl |
| 360 | O | —CH(CH₃)-2-thienyl |
| 361 | S | —CH(CH₃)-2-thienyl |
| 362 | O | —CH(CH₃)-3-thienyl |
| 363 | S | —CH(CH₃)-3-thienyl |
| 364 | O | —CH(CH₃)-2-benzo[b]thienyl |
| 365 | S | —CH(CH₃)-2-benzo[b]thienyl |
| 366 | O | —CH(CH₃)₂-2-benzo[b]furyl |
| 367 | S | —CH(CH₃)₂-2-benzo[b]furyl |
| 368 | O | —CH(CH₃)-2-thiazoyl |
| 369 | S | —CH(CH₃)-2-thiazoyl |
| 370 | O | —CH(CH₃)-2-imidazoyl |
| 371 | S | —CH(CH₃)-2-imidazoyl |
| 372 | O | —CH(CH₃)-2-pyrimidyl |
| 373 | S | —CH(CH₃)-2-pyrimidyl |

The substituted amide-linked N-hydroxyurea compounds of Examples 374– 384 as shown in Table 8 are prepared by the method used for Example 57 substituting m-phenoxybenzoic acid with the requisite substituted benzoic acid derivative and by employing the procedure from example 57 while employing the products from examples 48, 49, or by synthesis of other analogues derived from natural and unnatural amino acids following the procedures in example 48.

TABLE 8

Substituted Phenoxybenzoate Amide-linked N-Hydroxyureas

| Example | R₄ |
|---|---|
| 374 | (S)-Me |
| 375 | (R)-Me |
| 376 | (S)-Et |
| 377 | (R)-Et |
| 378 | (R)-n-Pr |
| 379 | (R)-i-Pr |
| 380 | (R)-i-Bu |
| 381 | (R)-n-Bu |
| 382 | (R)-CH₂Ph |
| 383 | (R)-CH₂OH |
| 384 | (R)-(CH₂)₄NH₂ |

The substituted amide-linked N-hydroxyurea compounds of Examples 385– 428 shown in Table 9 are prepared by the method used for Example 1 substituting m-phenoxyaniline with the requisite substituted ortho-, meta-, or para-hydroxyaniline derivative which can be prepared according to the alkylation procedure outlined in example 23 utilizing N-Boc-hydroxyanilines in lieu of hydroxybenzoate.

TABLE 9

Substituted Hydroxyaniline Amide-linked N-Hydroxyureas

| Example | R₁ |
|---|---|
| 385 | —CH₂CH₃ |
| 386 | —(CH₂)₂CH₃ |
| 387 | —(CH₂)₃CH₃ |
| 388 | —(CH₂)₄CH₃ |
| 389 | —(CH₂)₅CH₃ |
| 390 | —CH₂CH(CH₃)₂ |
| 391 | —(CH₂)₂CH(CH₃)₂ |
| 392 | —(CH₂)₃CH(CH₃)₂ |
| 393 | —(CH₂)₄CH(CH₃)₂ |
| 394 | —CH₂CH═CH₂ |
| 395 | -trans-CH₂CH═CHCH₃ |
| 396 | -trans-CH₂C(CH₃)═CHCH₃ |
| 397 | —CH₂CH═C(CH₃)CH₃ |
| 398 | —CH₂CH₂N(CH₃)₂ |
| 399 | —CH₂CH₂N(CH₂CH₃)₂ |
| 400 | —(CH₂)₂CH₂N(CH₃)₂ |
| 401 | —(CH₂)₂CH₂N(CH₂CH₃)₂ |
| 402 | —CH₂-2-pyridyl |
| 403 | —CH₂-3-pyridyl |
| 404 | —CH₂-4-pyridyl |
| 405 | —CH₂-2-furyl |
| 406 | —CH₂-3-furyl |
| 407 | —CH₂-2-thienyl |
| 408 | —CH₂-3-thienyl |
| 409 | —CH₂-2-benzo[b]thienyl |
| 410 | —CH₂-2-benzo[b]furyl |
| 411 | —CH₂-2-thiazoyl |
| 412 | —CH₂-2-imidazoyl |
| 413 | —CH(CH₃)-2-pyrimidyl |
| 414 | —CH(CH₃)-2-pyridyl |
| 415 | —CH(CH₃)-3-pyridyl |
| 416 | —CH(CH₃)-4-pyridyl |

TABLE 9-continued

Substituted Hydroxyaniline Amide-linked N-Hydroxyureas

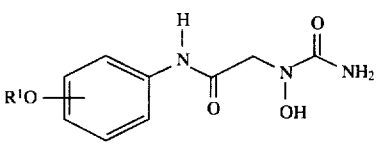

| Example | R₁ |
|---|---|
| 417 | —CH(CH₃)₂-2-furyl |
| 418 | —CH(CH₃)-3-furyl |
| 419 | —CH(CH₃)-2-thienyl |
| 420 | —CH(CH₃)-3-thienyl |
| 421 | —CH(CH₃)-2-benzo[b]thienyl |
| 422 | —CH(CH₃)₂-2-benzo[b]furyl |
| 423 | —CH(CH₃)-2-thiazoyl |
| 424 | —CH(CH₃)-2-imidazoyl |
| 425 | —CH(CH₃)-2-pyrimidyl |
| 426 | -2-pyridyl |
| 427 | -3-pyridyl |
| 428 | -4-pyridyl |

The substituted amide-linked N-hydroxyurea compounds of Examples 429– 508 as shown in Table 10 are prepared by the method used for Example 1 substituting m-phenoxyaniline with the requisite substituted ortho-, meta-, or para-mercaptoaniline derivative which can be prepared by alkylation of the corresponding mercaptoaniline according to the procedure described in example 23 for the alkylation of 3-hydroxybenzoate but employing N-Boc-mercaptoaniline in lieu of 3-hydroxybenzoate.

TABLE 10

Substituted Mercaptoaniline Amide-linked N-Hydroxyureas

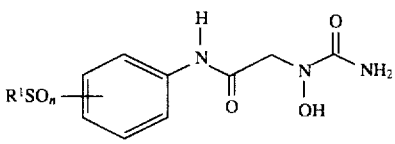

| Example | n | R₁ |
|---|---|---|
| 429 | 0 | —(CH₂)₂CH₃ |
| 430 | 2 | —(CH₂)₂CH₃ |
| 431 | 0 | —(CH₂)₃CH₃ |
| 432 | 2 | —(CH₂)₃CH₃ |
| 433 | 0 | —(CH₂)₄CH₃ |
| 434 | 2 | —(CH₂)₄CH₃ |
| 435 | 0 | —(CH₂)₅CH₃ |
| 436 | 2 | —(CH₂)₅CH₃ |
| 437 | 0 | —CH₂CH(CH₃)₂ |
| 438 | 2 | —CH₂CH(CH₃)₂ |
| 439 | 0 | —(CH₂)₂CH(CH₃)₂ |
| 440 | 2 | —(CH₂)₂CH(CH₃)₂ |
| 441 | 0 | —(CH₂)₃CH(CH₃)₂ |
| 442 | 2 | —(CH₂)₃CH(CH₃)₂ |
| 443 | 0 | —(CH₂)₄CH(CH₃)₂ |
| 444 | 2 | —(CH₂)₄CH(CH₃)₂ |
| 445 | 0 | —CH₂CH=CH₂ |
| 446 | 2 | —CH₂CH=CH₂ |
| 447 | 0 | -trans-CH₂CH=CHCH₃ |
| 448 | 2 | -trans-CH₂CH=CHCH₃ |
| 449 | 0 | -trans-CH₂C(CH₃)=CHCH₃ |
| 450 | 2 | -trans-CH₂C(CH₃)=CHCH₃ |
| 451 | 0 | —CH₂CH=C(CH₃)CH₃ |
| 452 | 2 | —CH₂CH=C(CH₃)CH₃ |
| 453 | 0 | —CH₂CH₂N(CH₃)₂ |
| 454 | 2 | —CH₂CH₂N(CH₃)₂ |

TABLE 10-continued

Substituted Mercaptoaniline Amide-linked N-Hydroxyureas

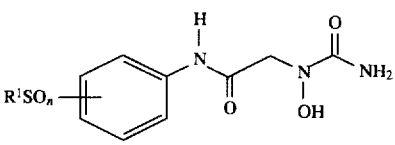

| Example | n | R₁ |
|---|---|---|
| 455 | 0 | —CH₂CH₂N(CH₂CH₃)₂ |
| 456 | 2 | —CH₂CH₂N(CH₂CH₃)₂ |
| 457 | 0 | —(CH₂)₂CH₂N(CH₃)₂ |
| 458 | 2 | —(CH₂)₂CH₂N(CH₃)₂ |
| 459 | 0 | —(CH₂)₂CH₂N(CH₂CH₃)₂ |
| 460 | 2 | —(CH₂)₂CH₂N(CH₂CH₃)₂ |
| 461 | 0 | —CH₂-2-pyridyl |
| 462 | 2 | —CH₂-2-pyridyl |
| 463 | 0 | —CH₂-3-pyridyl |
| 464 | 2 | —CH₂-3-pyridyl |
| 465 | 0 | —CH₂-4-pyridyl |
| 466 | 2 | —CH₂-4-pyridyl |
| 467 | 0 | —CH₂-2-furyl |
| 468 | 2 | —CH₂-2-furyl |
| 469 | 0 | —CH₂-3-furyl |
| 470 | 2 | —CH₂-3-furyl |
| 471 | 0 | —CH₂-2-thienyl |
| 472 | 2 | —CH₂-2-thienyl |
| 473 | 0 | —CH₂-3-thienyl |
| 474 | 2 | —CH₂-3-thienyl |
| 475 | 0 | —CH₂-2-benzo[b]thienyl |
| 476 | 2 | —CH₂-2-benzo[b]thienyl |
| 477 | 0 | —CH₂-2-benzo[b]furyl |
| 478 | 2 | —CH₂-2-benzo[b]furyl |
| 479 | 0 | —CH₂-2-thiazoyl |
| 480 | 2 | —CH₂-2-thiazoyl |
| 481 | 0 | —CH₂-2-imidazoyl |
| 482 | 2 | —CH₂-2-imidazoyl |
| 483 | 0 | —CH(CH₃)-2-pyrimidyl |
| 484 | 2 | —CH(CH₃)-2-pyrimidyl |
| 485 | 0 | —CH(CH₃)-2-pyridyl |
| 486 | 2 | —CH(CH₃)-2-pyridyl |
| 487 | 0 | —CH(CH₃)-3-pyridyl |
| 488 | 2 | —CH(CH₃)-3-pyridyl |
| 489 | 0 | —CH(CH₃)-4-pyridyl |
| 490 | 2 | —CH(CH₃)-4-pyridyl |
| 491 | 0 | —CH(CH₃)₂-2-furyl |
| 492 | 2 | —CH(CH₃)₂-2-furyl |
| 493 | 0 | —CH(CH₃)-3-furyl |
| 494 | 2 | —CH(CH₃)-3-furyl |
| 495 | 0 | —CH(CH₃)-2-thienyl |
| 496 | 2 | —CH(CH₃)-2-thienyl |
| 497 | 0 | —CH(CH₃)-3-thienyl |
| 498 | 2 | —CH(CH₃)-3-thienyl |
| 499 | 0 | —CH(CH₃)-2-benzo[b]thienyl |
| 500 | 2 | —CH(CH₃)-2-benzo[b]thienyl |
| 501 | 0 | —CH(CH₃)₂-2-benzo[b]furyl |
| 502 | 2 | —CH(CH₃)₂-2-benzo[b]furyl |
| 503 | 0 | —CH(CH₃)-2-thiazoyl |
| 504 | 2 | —CH(CH₃)-2-thiazoyl |
| 505 | 0 | —CH(CH₃)-2-imidazoyl |
| 506 | 2 | —CH(CH₃)-2-imidazoyl |
| 507 | 0 | —CH(CH₃)-2-pyrimidyl |
| 508 | 2 | —CH(CH₃)-2-pyrimidyl |

The substituted amide-linked N-hydroxyureas compounds of Examples 509–548 as shown in Table 11 are prepared by the method used for Example 1 substituting m-phenoxyaniline with the requisite substituted ortho-, meta-, or para-aminoaniline derivative which can be prepared by routine alkylative methodology for anilines.

TABLE 11

Substituted Aminobenzoate Amide-linked N-Hydroxyureas

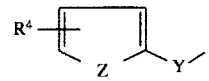

| Example | R1 |
|---|---|
| 509 | —(CH₂)₂CH₃ |
| 510 | —(CH₂)₃CH₃ |
| 511 | —(CH₂)₄CH₃ |
| 512 | —(CH₂)₅CH₃ |
| 513 | —CH₂CH(CH₃)₂ |
| 514 | —(CH₂)₂CH(CH₃)₂ |
| 515 | —(CH₂)₃CH(CH₃)₂ |
| 516 | —(CH₂)₄CH(CH₃)₂ |
| 517 | —CH₂CH=CH₂ |
| 518 | -trans-CH₂CH=CHCH₃ |
| 519 | -trans-CH₂C(CH₃)=CHCH₃ |
| 520 | —CH₂CH=C(CH₃)CH₃ |
| 521 | —CH₂CH₂N(CH₃)₂ |
| 522 | —CH₂CH₂N(CH₂CH₃)₂ |
| 523 | —(CH₂)₂CH₂N(CH₃)₂ |
| 524 | —(CH₂)₂CH₂N(CH₂CH₃)₂ |
| 525 | —CH₂-2-pyridyl |
| 526 | —CH₂-3-pyridyl |
| 527 | —CH₂-4-pyridyl |
| 528 | —CH₂-2-furyl |
| 529 | —CH₂-3-furyl |
| 530 | —CH₂-2-thienyl |
| 531 | —CH₂-3-thienyl |
| 532 | —CH₂-2-benzo[b]thienyl |
| 533 | —CH₂-2-benzo[b]furyl |
| 534 | —CH₂-2-thiazoyl |
| 535 | —CH₂-2-imidazoyl |
| 536 | —CH(CH₃)-2-pyrimidyl |
| 537 | —CH(CH₃)-2-pyridyl |
| 538 | —CH(CH₃)-3-pyridyl |
| 539 | —CH(CH₃)-4-pyridyl |
| 540 | —CH(CH₃)₂-2-furyl |
| 541 | —CH(CH₃)-3-furyl |
| 542 | —CH(CH₃)-2-thienyl |
| 543 | —CH(CH₃)-3-thienyl |
| 544 | —CH(CH₃)-2-benzo[b]thienyl |
| 545 | —CH(CH₃)₂-2-benzo[b]furyl |
| 546 | —CH(CH₃)-2-thiazoyl |
| 547 | —CH(CH₃)-2-imidazoyl |
| 548 | —CH(CH₃)-2-pyrimidyl |

The examples presented above are provided to enable one skilled in the art to practice the present invention and should not be read as limiting the scope of the invention which is defined by the appended claims.

We claim:

1. A compound having the structure

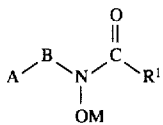

or a pharmaceutically acceptable salt thereof wherein $R^1$ is $NR^2R^3$ where $R^2$ and $R^3$ are independently selected from hydrogen and alkyl of from one to six carbon atoms;

A is

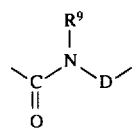

wherein $R^4$ is selected from
(a) phenoxy, optionally substituted with one, two, or three halogen atoms, alkyl of from one to six carbon atoms, haloalkyl of from one to six carbon atoms, phenylalkoxy in which the alkoxy portion is of from one to six carbon atoms, and
(b) thiophenoxy, optionally substituted with one, two, or three halogen atoms, alkyl of from one to six carbon atoms, haloalkyl of from one to six carbon atoms;

Y is a valence bond or is selected from
alkylene of from one to six carbon atoms,
alkenylene of from two to six carbon atoms, and
oxyalkylene of from one to six carbon atoms;

Z is oxygen or sulfur;

B is

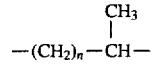

wherein $R^9$ is selected from
hydrogen,
alkyl of from one to six carbon atoms, and
D is straight or branched chain alkylene of from one to six carbon atoms; and M is hydrogen or a pharmaceutically acceptable cation.

2. A compound as defined by claim 1 wherein D is $(-CH_2-)_n$ or $$-(CH_2)_n-\overset{CH_3}{\underset{|}{CH}}-$$

wherein n is 1, 2, or 3.

3. A compound as defined by claim 1 selected from the group consisting of
N-hydroxy-N-[2-((5-(4-methylphenoxy)furan-2-oyl)amino)ethyl]urea;
N-hydroxy-N-[2-((5-(4-chlorophenoxy)fur-2-oyl)amino)ethyl]urea;
(R)-N-hydroxy-N-[2-((5-(4-chlorophenoxy)fur-2-oyl)amino)propyl]urea;
(S)-N-hydroxy-N-[2-((5-(4-chlorophenoxy)fur-2-oyl)amino)propyl]urea;
(R)-N-hydroxy-N-[3-((5-(4-fluorophenoxy)furan-2-oyl)amino)prop-2-yl]urea;
(S)-N-hydroxy-N-[3-((5-(4-fluorophenoxy)furan-2-oyl)amino)prop-2 yl]urea;
(R)-N-hydroxy-N-[3-((5-(4-fluorothiophenoxy)furan-2-0yl)amino)prop-2-yl]urea;
(S)-N-hydroxy-N-[3-((5-(4-fluorothiophenoxy)furan-2-oyl)amino)prop-2-yl]urea;
N-Hydroxy-N-[2-((5-(4-chlorophenoxy)fur-2-oyl)amino)ethyl]urea; and
N-Hydroxy-N-[3-((5-(4-fluorophenoxy)furan-2-oyl)amino)prop-2-yl]urea;
(R,S)-N-hydroxy-N-[3-((5-(4-fluorophenoxy)furan-2-oyl)amino)prop-2-yl]urea;

or a pharmaceutically acceptable salt thereof.

4. A pharmaceutical composition for inhibiting the biosynthesis of leukotrienes comprising a therapeutically effective amount of a compound as defined by claim 1 in combination with a pharmaceutically acceptable carrier.

5. A method of inhibiting the biosynthesis of leukotrienes comprising administering to a mammal in need of such treatment a therapeutically effective amount of a compound as defined by claim 1.

6. A compound as defined by claim 1 wherein Z is oxygen.

7. A compound as defined by claim 1 wherein Z is sulfur.

* * * * *

UNITED STATES PATENT AND TRADEMARK OFFICE
CERTIFICATE OF CORRECTION

PATENT NO. : 5,514,702
DATED : May 7, 1996
INVENTOR(S) : Dellaria, et. al.

It is certified that error appears in the above-indentified patent and that said Letters Patent is hereby corrected as shown below:

Column 66, line 56-57, change "Oyl" to --oyl--.

Signed and Sealed this

Tenth Day of December, 1996

Attest:

BRUCE LEHMAN

Attesting Officer  Commissioner of Patents and Trademarks